(12) United States Patent
Zhi

(10) Patent No.: US 10,076,504 B2
(45) Date of Patent: Sep. 18, 2018

(54) GLUCAGON ANTAGONISTS

(71) Applicant: Ligand Pharmaceuticals, Inc., San Diego, CA (US)

(72) Inventor: Lin Zhi, San Diego, CA (US)

(*) Notice: Subject to any disclaimer, the term of this patent is extended or adjusted under 35 U.S.C. 154(b) by 0 days.

(21) Appl. No.: 15/317,390

(22) PCT Filed: Jun. 11, 2015

(86) PCT No.: PCT/US2015/035400
§ 371 (c)(1),
(2) Date: Dec. 8, 2016

(87) PCT Pub. No.: WO2015/191900
PCT Pub. Date: Dec. 17, 2015

(65) Prior Publication Data
US 2017/0216229 A1    Aug. 3, 2017

Related U.S. Application Data

(60) Provisional application No. 62/011,547, filed on Jun. 12, 2014, provisional application No. 62/073,916, filed on Oct. 31, 2014, provisional application No. 62/078,926, filed on Nov. 12, 2014.

(51) Int. Cl.
*A61K 31/167* (2006.01)
*A61K 31/423* (2006.01)

(52) U.S. Cl.
CPC .......... *A61K 31/167* (2013.01); *A61K 31/423* (2013.01)

(58) Field of Classification Search
None
See application file for complete search history.

(56) References Cited

U.S. PATENT DOCUMENTS

| | | | |
|---|---|---|---|
| 3,524,846 A | 8/1970 | Moffatt et al. | |
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,157,027 A | 10/1992 | Biller et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,132,420 A | 10/2000 | Dionne et al. | |
| 6,245,357 B1 | 6/2001 | Edgren et al. | |
| 6,270,787 B1 | 8/2001 | Ayer | |
| 6,283,953 B1 | 9/2001 | Ayer et al. | |
| 6,287,295 B1 | 9/2001 | Chen et al. | |
| 6,333,050 B2 | 12/2001 | Wong et al. | |
| 6,342,249 B1 | 1/2002 | Wong et al. | |
| 6,365,185 B1 | 4/2002 | Ritschel et al. | |
| 6,368,626 B1 | 4/2002 | Bhatt et al. | |
| 6,375,975 B1 | 4/2002 | Modi | |

(Continued)

FOREIGN PATENT DOCUMENTS

| | | |
|---|---|---|
| CA | 2678265 | 10/2015 |
| CA | 2770298 | 6/2017 |

(Continued)

OTHER PUBLICATIONS

U.S. Appl. No. 12/526,458, filed Aug. 7, 2009, Metabasis Therapeutics, Inc.
Alexander, P., et al., "Preparation of 9-(2-Phosphonomethoxyethyl) Adenine Esters as Potential Prodrugs," Col/ect. Czech. Chem. Commun. (in prior U.S. Appl. No. 12/526,45859),1853-1869, Nakladatelstvi Ceskoslovenski Akademie Ved. (1994).
Alza Corporation, "L-Oros™ Technology—Advancing New Therapies Through ALZA's Liquid Drug Formation," Delivery Times, vol. II, Issue II, 2002, 12 pages.
American Heart Association, "Metabolic Syndrome" <http://www.americanheart.org/presenter.jhtml?identifier=4756>, Accessed Mar. 31, 2009.
Ash and Ash, Eds., Handbook of Pharmaceutical Additives, 3rd ed, Gower Publishing Company, 2007, 3 pages.

(Continued)

*Primary Examiner* — Karl J Puttlitz
(74) *Attorney, Agent, or Firm* — Sterne, Kessler, Goldstein & Fox PLLC

(57) ABSTRACT

Provided herein are compounds, including enantiomerically pure forms thereof, and pharmaceutically acceptable salts or co-crystals and prodrugs thereof which have glucagon receptor antagonist or inverse agonist activity. Further, provided herein are pharmaceutical compositions comprising the same as well as methods of treating, preventing, delaying the time to onset or reducing the risk for the development or progression of a disease or condition for which one or more glucagon receptor antagonist is indicated, including Type I and II diabetes, insulin resistance and hyperglycemia. Moreover, provided herein are methods of making or manufacturing compounds disclosed herein, including enantiomerically pure forms thereof, and pharmaceutically acceptable salts or co-crystals and prodrugs thereof.

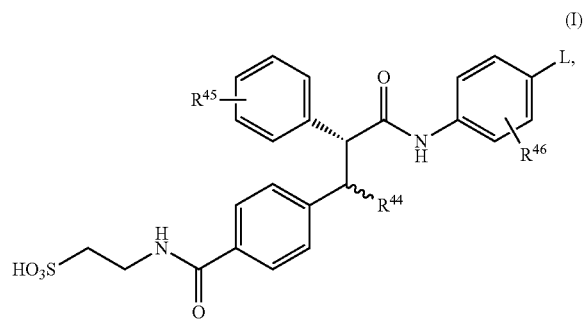

15 Claims, 10 Drawing Sheets

(56) References Cited

U.S. PATENT DOCUMENTS

| | | | |
|---|---|---|---|
| 6,375,978 | B1 | 4/2002 | Kleiner et al. |
| 6,503,949 | B1 | 1/2003 | Lau et al. |
| 6,875,760 | B2 | 4/2005 | Lau et al. |
| 6,881,746 | B2 | 4/2005 | Lau et al. |
| 7,301,036 | B2 | 11/2007 | Parmee et al. |
| 8,519,145 | B2 | 8/2013 | Kang et al. |
| 8,710,236 | B2 | 4/2014 | Gomez-Galeno et al. |
| 8,907,103 | B2 | 12/2014 | Gomez-Galeno et al. |
| 9,169,201 | B2 | 10/2015 | Gomez-Galeno et al. |
| 9,701,626 | B2 | 7/2017 | Gomez-Galeno et al. |
| 9,783,494 | B2 | 10/2017 | Gomez-Galeno et al. |
| 2003/0212119 | A1 | 11/2003 | Lau et al. |
| 2003/0236292 | A1 | 12/2003 | Kodra et al. |
| 2004/0014789 | A1 | 1/2004 | Lau et al. |
| 2004/0152750 | A1 | 8/2004 | Kodra et al. |
| 2005/0288329 | A1 | 12/2005 | Yao et al. |
| 2006/0084681 | A1 | 4/2006 | Parmee et al. |
| 2006/0116366 | A1 | 6/2006 | Parmee et al. |
| 2007/0015757 | A1 | 1/2007 | Madsen et al. |
| 2007/0054902 | A1 | 3/2007 | Fukui et al. |
| 2007/0088071 | A1 | 4/2007 | Kim et al. |
| 2007/0105930 | A1 | 5/2007 | Parmee et al. |
| 2007/0203186 | A1 | 8/2007 | Beeson et al. |
| 2007/0249688 | A1 | 10/2007 | Conner et al. |
| 2008/0085926 | A1 | 4/2008 | Stelmach et al. |
| 2008/0108620 | A1 | 5/2008 | Brockunier et al. |
| 2008/0125468 | A1 | 5/2008 | Chappell et al. |
| 2013/0030029 | A1* | 1/2013 | Gomez-Galeno ..... C07C 309/15 514/375 |
| 2015/0087680 | A1 | 3/2015 | Gomez-Galeno et al. |
| 2016/0009639 | A1 | 1/2016 | Gomez-Galeno et al. |

FOREIGN PATENT DOCUMENTS

| | | |
|---|---|---|
| CN | 1774433 A | 5/2006 |
| CN | 1784226 A | 6/2006 |
| CN | 101610995 | 12/2009 |
| CN | 102292316 | 7/2015 |
| CN | 104803891 A | 7/2015 |
| CN | 105566265 A | 5/2016 |
| CN | 106687118 A | 5/2017 |
| DK | 2799428 | 2/2017 |
| EP | 0 284 240 B2 | 6/1993 |
| EP | 0 632 048 A1 | 1/1995 |
| EP | 2 129 654 A1 | 12/2009 |
| EP | 2 326 618 A1 | 10/2014 |
| EP | 2 786 985 A1 | 10/2014 |
| EP | 2 799 428 | 11/2016 |
| EP | 3 153 501 | 4/2017 |
| EP | 3 154 956 | 4/2017 |
| HK | 1203481 A | 10/2015 |
| IN | 10423-DLNP-2015 | 6/2016 |
| IN | 273645 | 6/2016 |
| JP | 63-32538 | 2/1988 |
| JP | 63-231452 A2 | 9/1988 |
| JP | 09-241284 A | 9/1997 |
| JP | 11-97740 A | 4/1999 |
| JP | 2004-501897 | 1/2004 |
| JP | 2005-511683 | 4/2005 |
| JP | 2010-511604 | 4/2010 |
| JP | 2010-518124 A | 5/2010 |
| JP | 2013-177426 | 9/2013 |
| JP | 5322951 | 10/2013 |
| JP | 5684126 | 1/2015 |
| JP | 2015-129133 | 7/2015 |
| JP | 2016-041702 | 3/2016 |
| JP | 2017-101039 | 6/2017 |
| JP | 2017-51900 | 7/2017 |
| KR | 10-2008-0050348 | 6/2008 |
| KR | 10-2009-0110895 A | 10/2009 |
| KR | 10-2015-0008922 | 1/2015 |
| KR | 10-1538810 | 7/2015 |
| KR | 10-1599089 | 2/2016 |
| KR | 10-2016-0052792 | 5/2016 |
| KR | 10-1634515 | 6/2016 |
| KR | 10-2017-0085615 | 7/2017 |
| MX | 318858 | 3/2014 |
| WO | WO 90/08155 A1 | 7/1990 |
| WO | WO 90/10636 A1 | 9/1990 |
| WO | WO 91/19721 A1 | 12/1991 |
| WO | WO 00/069810 A1 | 11/2000 |
| WO | WO 00/071510 A2 | 11/2000 |
| WO | WO 01/019830 A1 | 3/2001 |
| WO | WO 01/062717 A1 | 8/2001 |
| WO | WO 02/00612 A1 | 1/2002 |
| WO | WO 02/040444 A1 | 5/2002 |
| WO | WO 03/048109 A1 | 6/2003 |
| WO | WO 03/053938 A1 | 7/2003 |
| WO | WO 04/002480 A1 | 1/2004 |
| WO | WO 04/050039 A2 | 6/2004 |
| WO | WO 04/052869 A1 | 6/2004 |
| WO | WO 04/069158 A2 | 8/2004 |
| WO | WO 2004/092156 A1 | 10/2004 |
| WO | WO 04/100875 A2 | 11/2004 |
| WO | WO 05/051298 A1 | 6/2005 |
| WO | WO 05/054213 A1 | 6/2005 |
| WO | WO 05/065680 A1 | 7/2005 |
| WO | WO 05/118542 A1 | 12/2005 |
| WO | WO 05/121097 A2 | 12/2005 |
| WO | WO 05/123668 A1 | 12/2005 |
| WO | WO 06/086488 A2 | 8/2006 |
| WO | WO 06/102067 A1 | 9/2006 |
| WO | WO 06/104826 A2 | 10/2006 |
| WO | WO 07/015999 A2 | 2/2007 |
| WO | WO 07/047177 A1 | 4/2007 |
| WO | WO 07/106181 A2 | 9/2007 |
| WO | WO 07/111864 A2 | 10/2007 |
| WO | WO 07/114855 A2 | 10/2007 |
| WO | WO 07/120270 A2 | 10/2007 |
| WO | WO 07/120284 A2 | 10/2007 |
| WO | WO 07/123581 A1 | 11/2007 |
| WO | WO 07/136577 A2 | 11/2007 |
| WO | WO 08/001883 A1 | 1/2008 |
| WO | WO 08/042223 A1 | 4/2008 |
| WO | WO 08/066356 A1 | 6/2008 |
| WO | WO 08/098244 A1 | 8/2008 |
| WO | WO 10/019830 A1 | 2/2010 |
| WO | WO 2013/012959 A1 | 1/2013 |
| WO | WO 2015/191900 A1 | 12/2015 |
| WO | WO 2017/084226 | 5/2017 |

OTHER PUBLICATIONS

Baddiley et al., "Structure of Coenzyme A," Nature 171:76 (1953).
Benzaria et al., "Synthesis, in Vitro Antiviral Evaluation, and Stability Studies of Bis(S-acyl-2-thioethyl) Ester Derivatives of 9-[2-(Phosphonomethoxy)ethyl] adenine (PMEA) as Potential PMEA Prodrugs with Improved Oral Bioavailability," J. Med. Chem. 39(25):4958-4965 (1996).
Bhongle et al., "Expedient and High-Yield Synthesis of Alkylphosphonyl Cichlorides Under Mile, Neutral Conditions: Reaction of Bis (Trimethylsilyl) Slkyl Phosphonates with Oxalyl Chloridel Dimethylformarnide," Synth. Commu. 17:1071-1706 (1987).
Blackburn et al., "Specific Dealkylation of Phosphonate Esters using Iodotrimcthylsilanc," J. Chem. Soc. , Chem. Commun. 870-871 (1978).
Brand et al., "Evidence for a Major Role of Glucagon in the Hyperglycemia of Experimental Diabetes," A Journal of the American Diabetes Association, 1994, 43 (Suppl. 1), 172A.
Brand et al., "Immunoneutralization of endogenous glucagon with monoclonal glucagon antibody normalizes hyperglycaemia in moderately streptozotocin-diabetic rats," Diabetologia 1994, vol. 37, pp. 985-993.
Brechbühler et al., "Die Reaktion von Carbonsauren mit Acetalen des N, N-Dimethylformmids: eine Veresterungsmethode," Helv. Chim. Acta. 48(7):1746-1771 (1965).
Bundgaaard, ed., Design of Prodrugs, Elsevier Science, Amsterdam, 1985.
Busch-Peterson et al., "Lithium N-trityl-N-(R)-I-phenethylamide, a readily available and useful base for the enantioselective formation of chiral cnolates from achiral ketones," Tetrahedron Letters 41(36):6941-6944 (2000).

(56) References Cited

OTHER PUBLICATIONS

Campagne, J.-M. et al., "Synthesis of Mixed Phosphonate Diester Analogues of Dipeptides using BOP or PyBOP Reagents," Tetrahedron Left. 34(42), 6743-6744, Pergamon Press Ltd. (1993).
Campbell, DA, "The Synthesis of Phosphonate Esters, an Extension of the Mitsunobu Reaction," J. Org. Chem. 57,6331-6335, American Chemical Society (1992).
CAS Registry No. 852460-16-3, STN Entry Date Jun. 17, 2005.
CAS Registry No. 131055-48-6, STN Entry Date Dec. 14, 1990.
CAS Registry No. 127192-35-2, STN Entry Date May 18, 1990.
CAS Registry No. 141740-28-5, STN Entry Date Jun. 12, 1992.
CAS Registry No. 141220-32-8, STN Entry Date May 8, 1992.
CAS Registry No. 127192-36-3, STN Entry Date May 18, 1990.
CAS Registry 699001-74-6, STN Entry Date Jun. 25, 2004.
Casara, P.J. et al., Synthesis of Acid Stable 5'-O-Fluoromethyl Phosphonates of Nucleosides. Evaluation as Inhibitors of Reverse Transcriptase,• Bioorg. Med. Chem. Left. 2(2), 145-148, Pergamon Press pic. (1992).
Cereda et al., "Solid-phase synthesis of 3-hydroxymethyl isoxazoles via resin bound nitrile oxides," Tetrahedron Lett. 42(30):4951-4953(2001).
Coppi et al., "Lewis Acid Mediated Condensation of Alkenols and Aldehydes. A Selective Synthesis of Tetrahydropyrans and Oxepanes," J. Org. Chern. 53(4) 911-913 (1988).
Curran et al., "Thermolysis ofbis[2-[(trimethylsilyl)oxy]prop-2-yl] furoxan (TOP-furoxan). The First Practical Method for Intermolecular Cycloaddition of an in Situ Generated Nitrile Oxide with 1, 2-Di- and Trisubstituted Olefins," J. Am. Chem. Soc. 107(21):6023-6028 (1985).
DeLombaert et al., "N-Phosphonomethyl Dipeptides and Their Phosphonate Prodrugs, a New Generation of Neutral Endopeptidase (NEP, TIC3.4.24.11) Inhibitors," J. Med. Chem. 37(7):498-511 (1994).
Egron et al., "Synthesis and Anti-HIV Activity of Some S-Acyl-2-thioethyl (SATE) Phosphoramidate Derivatives of3'-Acido-2' 3'-dideoxythymidine," Nucleosides & Nucleotides 18(4):981-982 (1999).
Elhaddadi et al., "A Convenient Synthesis of Alkyl and Dialkyl 1-benzyloxyamino alkyl phosphonates and phosphinates," Phosphorus, Sulfur and Silicon 54:143-150 (1990).
Elliott, RL. et al., "Synthesis and Biological Evaluation of Phosphonamidate Peptide Inhibitors of Enkephalinase and Angiotensin-Converting Enzyme," J. Med. Chem. 28: 1208-1216, American Chemical Society (1985).
Farquhar et al., "Biologically Reversible Phosphate-Protective Groups," J. Pharm. Sci. 72(3):324-325 (1983).
Faulon, J-L., et al.: "The Signature Molecular Descriptor. 2. Enumerating Molecules from Their Extended Valence Sequences," Journal of Chemical Information and Computer Sciences, 2003, vol. 43, No. 3, pp. 721-734.
Federal Register 2011, 76 (27), p. 7166.
Ferres, "Pro-Drugs of B-Lactam Antibiotics," Drugs of Today 19(9):499-538 (1983).
Franchetti, P. et al.: Potent and selective inhibitors of human Immunodeficiency virus protease structurally related toL-694,746, Antiviral Chemistry and Chemotherapy, 1998, vol. 9, No. 4, pp. 303-309.
Freed et al., "Evidence for Acyloxymethyl Esters of Pyrimidine 5'-Deoxyribonucleotides as Extracellular Sources of Active 5'-Deoxyribonucleotides in Cultured Cells," Biochem. Pharmac. 38:3193-3198 (1989).
Garbisch et al, "Conformations. IV. The Conformational Preference of the Phenyl Group in Cyclohexane," J. Am. Chem. Soc., 1963, vol. 85, pp. 3228-3231.
Gibson, Ed., Pharmaceutical Preformulation and Formulation, CRC Press LLC, Boca Raton, FL, 2004.
Greene et al., Protective Groups in Organic Synthesis, John Wiley, New York, 1990.
Grundy et al., "Diagnosis and Management of the Metabolic Syndrome," Circulation, 112 (2005), p. 2735-2752.

Gupta et al., "An Improved Synthesis of Vinylic Phosphonates from Ketones," Synth. Commun. 10(4):299-304 (1980).
Hoffman, "A Simple Efficient Synthesis of Dibenzyl and Di-p-nitrobenzyl 1-Hydroxyalkanephosphonates," Synthesis 1988(1):62-64 (1988).
Huang et al., "a-Hypervalent Iodine Functionalized Phosphonium and Arsonium Ylides and Their Tandem Reaction as Umpolung Reagents," J Org. Chem. 67(23):8261-8264 (2002).
Inanaga et al., "A Rapid Esterification by Means of Mixed Anydride and Its Application to Large-ring Lactonization," Bulletin of the Chemical Society of Japan 52(7):1989-1993 (1979).
Johnson et al., "The Regulation of Gluconeogenesis in Isolated Rat Liver Cells by Glucagon, Insulan, Dibutyrl Cyclic Adenosine Monophosphate, and Fatty Acids," J. Biol. Chem., 1972, vol. 247, No. 10, pp. 3229-3235.
Juliano, Ed., Drug Delivery Systems, Oxford Univ. Press, Oxford, 1980.
Kerns et al., "Selective N-Sulfation of Glucosamine Derivatives Using Phenyl Chlorosulfate in Non-Qqueous Solvent," Synthetic Communications., 26:2671-2680, 1996.
Khamnei, S. et al., "Neighboring Group Catalysis in the Design of Nucleotide Prodrugs," J. Med. Chem. 39, 4109-4115, American Chemical Society (1996).
Kim, Cherug-ju, Controlled Release Dosage Form Design, 231-238, Technomic Publishing, Lancaster PA 2000.
Kozma, CRC Handbook of Optical resolutions via Diastereomeric Salt Formation, CRC Press, 2001.
Kurti et al., Strategic Applications of Named Reactions in Organic Synthesis, Elsvier, 340-342, 2005.
Kurukulasuriya et al., "Biaryl amide glucagon receptor antagonists," Bioorg. Med. Chem. Lett. 14(9):2047-2050 (2004).
Larock, Comprehensive Organic transformations, VCH, New York, 1989.
Latour et al., "Simple Syntheses of 2-Hydroxymethy-1, 3-propanediol and Related Compounds," Synthesis 1987(8):742-745 (1987).
Lee et al., "Synthesis and In Vitro Activity of Novel Isoxazolyl Tetrahydropyridinyl Oxazolidinone Antibacterial Agents," Bioorg. Med. Chern. Lett. 13(22):4117-4120 (2003).
Lejczak et al., Transcstcrification ofDiphenyl Phosphonates Using the Potassium Fluoride/Crown Ether/Alcohol System; Part 2. The Use of Diphenyl 1-Aminoalkanephosphonates in Phosphonopeptide Synthesis 1982(5):412-414 (1982).
Li et al.: "Chiral Drug Separation," Encyclopedia of Chemical Processing (2006), pp. 449-458.
Lyapkalo et al., (Enantioselective Synthesis of Cyclohexenylalkenes by Asymmetric Depprotonation of 4-tert-Butylcyclohexanone Followed by O-Nonatlation and Heck Couplings, SynZett 1292-1295 (2001).
Martin et al., "Synthesis and Antiviral Activity of Various Esters of 9-[(1 ,3-Dihydroxy-2-propoxy)methyl]guanine," J. Pharm. Sci. 76(2):180-184 (1987).
Mathur,"Metabolic Syndrome" see section "How is metabolic syndrome defined?" <http://www.medicinenet.com/metabolic syndrome/article.htm>, pp. 2-3, Accessed Mar. 31, 2009.
McGuigan, C. et al., "Kinase Bypass: A New Strategy for Anti-HIV Drug Design," Bioorganic & Medicinal Chemistry Letters 3(6): 1207-1210, Pergamon Press Ltd. (1993).
McKenna et al., "The facile dealkylation of phosphonic acid dialkyl esters by bromotrimcthylsilanc," Tetrahedron Lett. 2:155-158 (1977).
Meier, C. et al., "Cyclic Saligenyl Phosphotriesters of 2',3'-Dideoxy-2',3'-didehydrothymidine (d4T)—A New Pro-Nucleotide Approach," Bioorganic Med. Chem. Lett. 7(2), 99-104, Elsevier Science Ltd. (1997).
Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonacetate," J. Chem. Soc. Perkin Trans. 1 38:2345-2353, Chemical Society, London (1992).
Mitsunobu, 0., "The Use of Diethyl Azodicarboxylate and Triphenylphosphine in Synthesis and Transformation of Natural Products," Synthesis 1-28, Georg Thieme Verlag (1981).

(56) References Cited

OTHER PUBLICATIONS

Moriarty et al., "Diphenyl Methylphosphonate as a Phosphonylation Reagent with High Diastereoselectivity at Phosphorus," Tetrahedron Lett. 38(15):2597-2600 (1997).
Mukalyama et al., "Synthesis of Oligothymidylates and Nucleoside Cyclic Phosphates by Oxidation-Reduction Condensation," J. Am. Chem. Soc. 94(24):8528-8532 (1972).
Nishimura et al., "Orally Active 1-(Cyclohexyloxycarbonyloxy)alkyl Ester Prodrugs of Cefotiam," J. Antibiotics 40(1):81-90 (1987).
Ogg, M.S. et al., "A Reporter Gene Assay to Assess the Molecular Mechanisms of Xenobiotic-dependent Induction of the Human CYP3A4 Gene in Vitro," Xenobiotica 29(3), 269-279, Taylor & Francis Ltd. (Mar. 1999).
Ohashi, K. et al., "Synthesis of Phosphonosphingoglycolipid Found in Marine Snail Turbo Cornutus," Tetrahedron Lett. 29(10), 1189-1192, Pergamon Press pic. (1988).
Patois et al., "Easy preparation of alkylphosphonyl dichlorides," Bull. Soc. Chim Fr. 130:485-487 (1993).
Pelchowicz, "Organic Phosphorus Compounds. Part 1.The Reaction of Dialkyl Mthylphosphnates and Methylphosphonothionates with Inorganic Acid Chlorides," J Chern. Soc. 238-240 (1961).
Petasis et al., "The boronic acid mannich reaction: A new method for the synthesis of geometrically pure allylarnines," Tetrahedron Lett. 34(4):583-586 (1993).
Posner et al., "3-bromo-2-pyrone: an easily prepared chameleon diene and a synthetic equivalent of 2-pyrone in thermal diels-alder cycloadditions," Tetrahedron Letters 32(39):5295-5298 (1991).
PubMed Health,"Type 1 diabetes'" Jun. 28, 2011.
Puech et al., "Intracellular delivery ofnucleoside monophosphates through a reductase-mediated activation process," Antiviral Res. 22(2-3):155-174 (1993).
Quast et al., "Herstellung von Methylphosphonsaure-dichlorid," Synthesis 1974(7):490 (1974).
Rabinowitz, "The Reactions of Phosphonic Acid Esters with Acid Chlorides. A Very Mild Ilydrolytic Route," J. Org. Chem. 28(11):2975-2978 (1963).
Ramachandran et al., "Efficient General Synthesis of 1,2- and 1,3-diols in High Enantiomeric Excess via the Intramolecular Asymmetric Reduction of the Corresponding Ketoalkyl Diisopinocampheylborinate Intermediates," Tetrahedron, 38(5):761-764 (1997).
Rao et al., "Studies directed towards the synthesis of immunosuppressive agent FK-506: synthesis of the entire top-half," Tetrahedron Letters 32(4):547-550 (1991).
Rathbone et al, Eds., Modified-Release Drug Deliver Technology, Drugs and the Pharmaceutical Science, Marcel Dekker, Inc.: New York, NY, vol. 126, 2003.
Remington: The Science and Practice of Pharmacy, 21st Ed., Lippincott Williams & Wilkins, Philadephia, PA, 2005.
Remington's Pharmaceutical Sciences, 18th ed., Mack Publishing, Easton PA, 173, 1990, and pp. 172-174.
Roche, Ed., Design of Biopharmaceutical Properties through Prodrugs and Analogs, American Pharmaceutical Association, Washington, 1977.
Roden et al., "The Roles of Insulin and Glucagon in the Regulation of Hepatic Glycogen Synthesis and Turnover in Humans," J. Clin. Invest. 1996, vol. 97, No. 3, pp. 642-648.
Rosowsky et al., "Methotrexate Analogues. 32. Chain Extension, a-Carboxyl Delection, and y-Carboxyl Replacement by Sulfonate and Phosphonate: Effect on Enzyme Binding and Cell-Growth Inhibition," J. Med. Chem. 31: 1326-1331 (1988).
Rowe et al., Eds., Handbook of Pharmaceutical Excipients, 5th Ed., The Pharmaceutical Press and the Merican Pharmaceutical Association, 2006.
Sakamoto et al., "The palladium-catalyzed arylation of 4H-1,3-dioxin," Tetrahedron Lett. 33(45):6845-6848 (1992).
Schoeller, et al., "Measurement of energy expenditure in humans by doubly labeled water method," J. Appl Physiol., 53(4), pp. 955-959, (1982).

Serafinowska et al., "Synthesis and in Vivo Evaluation of Prodrugs of 9-[2-(Phosphonomethoxy)ethoxy] adenine," J. Med. Chem. 38(8):1372-1379 (1995).
Shafer et al., "On the Mechanism of Reductive Cleavage of Aryl Phosphates," J. Am. Chem. Soc. 99(15):5118-5123 (1977).
Shaw-Ponter et al., "New synthesis of both D- and L-3-O-Carbamoyl-2-deoxy-4-thioribosides, Substrates for I)-selective Glycosylations," Tetrahedron Letters 37:1871-1874 (1981).
Shono et al., "Electroreductive Elimination of Phenolic Hydroxyl Groups and a New Synthesis of Olivetol," J. Org. Chem. 44(25):4508-4511.
Siddiqui et al., "The Presence of Substitucnts on the Aryl Moeity of the Aryl Phosphoramidate Derivative of d4T Enhances Anti-HIV Efficacy in Cell Culture: A Structure-Activity Relationship," J. Med. Chem. 42: 393-399 (1999).
Silverman, Chapter 8: "Prodrugs and Drug Delivery Systems", The Organic Chemistry of Drug Design and Drug Action, Academic Press, 1992, pp. 352-401.
Singh et al., "Design and Synthesis ofIsoxazole Containing Bioisosteres of Epihatidine as Potent Nicotinic Acetylcholine Receptor Agonists," Chem. Pharm. Bull. 47(10):1501-1505 (1999).
Slavica et al., "Systhesis and Biological Activities of a New Set of Irreversibly Acting 2-(4'Isothiocyanatobenzyl)imidazoline Analogs in Rat Thoracic Aorta," J. Med. Chem. 1994, vol. 37, No. 12, pp. 1874-1881.
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med, Chem 37:1857-1864 (1994).
Still et al., "Direct synthesis of Z-unsaturated esters. A useful modification of the hormer-emmons olefination," Tetrahedron Letters 24(41):4405-4408 (1983).
Stowell et al., "The Mild Preparation of Synthetically Useful Phosphonic Dichlorides: Applicationt to the Synthesis of Cyclic Phosphonic Diesters and Diamides," Tetrahedron Letters 31(23):3261-3262 (1990).
Tawfik et al., "1,8-Diazabicyclo[5.4.0]undecene Mediated Transesterification ofp-Nitrophenyl Phosphonates: A Novel Route to Phosphono Esters," Synthesis 1993(10):968-972 (1993).
Toke et al., "A Versatile Building Block for the Synthesis of Substituted Cyclopropanephosphonic Acid Esters," Tetrahedron Letters 51(33):9167-9178 (1995).
Turner, JA, "A General Approach to the Synthesis of 1,6-,1,7-, and 1,8-Naphthyridines," J. Org. Chem. 55(15),4744-4750, American Chemical Society (1990).
United States Pharmacopeia, The, 23rd ed., pp. 1843-1844, 1995.
Valette et al., "Decomposition Pathways and in Vitro HIV Inhibitory Effects of IsoddA Pronucleotides: Toward a Rational Approach for Intracellular Delivery of Nucleotide 5'-Monophosphates," J. Med. Chem. 39(10):1981-1990 (1996).
Vanderwal et al., "An Enantioscicctive Synthesis of FR182877 Provides a Chemical Rationalization ofIts Structure and Affords Multigram Quantities ofIts Direct Precursor," J. Am. Chem. Soc. 125(18):5393-5407.
Xu et al., "A General Route to the Synthesis of N-Protected 1-Substituted and 1,2-Disubstituted Taurines," Synthesis 2004(2):276-282 (2004).
Yamamoto et. al., "Synthesis of Pyridine N-Oxide-SbCls Complexes and Their Intramolecular and Oxygen-Transfer Reaction," Tetrahedron 37:1871-1873 (1981).
Yan et al., "Preparation, Properties, Reactions, and Adenosine Receptor Affinities of Sulfophenylxanthine Nitrophenyl Esters: Toward the Development of Sulfonic Acid Prodrugs with Peroral Bioavailability," J. Med. Chem. 47(4):1031-1043 (2004).
Yao et al., "Generation of Nitroalkanes, Hydroximoyl Halides and Nitrile Oxides from the Reactions of B-Nitrostyrenes with Grignard or Organolithium Reagents," Tetrahedron Letters 54(5/6):791-822 (1998).
Younker et al., "A mechanistic Study of the Alkaline Hydrolysis of Diaryl Sulfate Diesters," J. Org. Chem. 69(26):9043-9048 (2004).
Ballatore: "Carboxylic Acid (Bio)Isosteres in Drug Design," ChemMedChem 8.3 (2013): 385-395.

(56) References Cited

OTHER PUBLICATIONS

R. Jason Herr: "5-Substituted--1H-tetrazoles as Carboxylic Acid Isosteres: Medicinal Chemistry and Synthetic Methods," Bioorg. Med. Chem. 10 (2002) 3379-3393.
Macchiarulo, et al.: "Exploring the other side of bilogically relevant chemical space: Insights into carboxylic, sulfonic and phosphonic acid bioisosteric relationships Roberto Pellicciari," Journal of Molecular Graphics and Modelling 26 (2007) 728-739.
Lidia Moerira Lima, et al.: "Bioisosterism: A Useful Strategy for Molecular Modificaion and Drug Design, Current Medicinal Chemistry," 2005, 12, 23-49.
Australian Office Action in AU Application No. 2008212816, dated Nov. 9, 2012.
Australian Office Action in AU Application No. 2008212816, dated Dec. 20, 2012.
Australian Office Action in AU Application No. 2014204420, dated Aug. 22, 2016.
Office Action in U.S. Appl. No. 13/083,321, dated Jul. 12, 2013.
Office Action in U.S. Appl. No. 14/860,593, dated Jan. 5, 2016.
Canadian Office Action in CA Application No. 2,678,265, dated Feb. 4, 2014.
Canadian Office Action in CA Application No. 2,678,265, dated Jul. 11, 2014.
Canadian Office Action in CA Application No. 2,894,112, dated Jul. 4, 2016.
First Office Action in Chinese Application No. 200880004461.9 dated Jun. 15, 2012.
Second Office Action in Chinese Application No. 200880004461.9 dated Apr. 28, 2013.
Third Office Action in Chinese Application No. 200880004461.9 dated Jan. 17, 2014.
Decision on Rejection in Chinese Application No. 200880004461.9 dated Jun. 27, 2014.
Supplementary Partial European Search Report dated Jul. 17, 2012, European Patent Application No, EP 08 72 9528, 7 pages.
Examination Report, re EP Application No. EP 08 729 528.3, dated Feb. 20, 2013.
Extended Search Report, re EP Application No. 14162609.3, dated Jan. 8, 2015.
Exam Report, re EP Application No. 14162609.3, dated Feb. 2, 2017.
Indian Office Action, re in Application No. 5771/DELNP/2009, dated Sep. 13, 2009.
Japanese Office Action, re JP Application No. JP 2009-549286, dated Feb. 26, 2013.
Japanese Office Action, re JP Application No. JP 2013-110101, dated Jun. 3, 2014.
Japanese Office Action, re JP Application No. JP 2013-110101, dated Jun. 2, 2015.
Japanese Pre-appeal Exam Report, re JP Application No. JP 2013-110101, dated Oct. 29, 2015.
Japanese Office Action, re JP Application No. JP 2015-196171, dated Nov. 8, 2016.
Korean Office Action (Reasons for Rejection), re KR Application No. 10-2012-7025865, (undated/docketing lists as Nov. 14, 2014).
Korean Office Action, re KR Application No. 10-2014-7036395, dated Mar. 23, 2015.
Korean Office Action, re KR Application No. 10-2014-7036395, dated Jan. 4, 2016.
Korean Notice on the Result of Reexamination, re KR Application No. 10-2014-7036395, dated (appx.) Jun. 16, 2016.
Korean Office Action (w/Translation), re KR Application No. 10-2016-7011147, dated Jul. 19, 2016.
Office Action in Mexico Application No. MX/a/2009/008534 dated Jun. 27, 2013.
Office Action in Mexico Application No. MX/a/2009/008534 (FA correspondence dated Nov. 5, 2013).
Office in Mexico Application No. MX/a/2014/003565, dated May 16, 2016 (w/translation).
Office in Mexico Application No. MX/a/2014/003565, dated Oct. 26, 2016 (w/translation).
International Search Report dated Jul. 17, 2008, in International Application No. PCT/US2008/053581.
International Preliminary Report on Patentability dated Aug. 11, 2009, in International Application No. PCT/US2008/053581.
Canadian Office Action, re CA Application No. 2,770,298, dated Jun. 8, 2015.
Canadian Office Action, re CA Application No. 2,770,298, dated Feb. 17, 2016.
Chinese Office Action in CN Application No. 200980141324.4, dated Apr. 15, 2013.
Chinese Search Report in CN Application No. 200980141324.4, dated Apr. 3, 2013.
Chinese Office Action in CN Application No. 200980141324.4, dated Jan. 6, 2014.
Chinese Third Office Action in CN Application No. 200980141324.4, dated Aug. 5, 2014.
Chinese First Office Action in CN Application No. 201510257808.2, dated Feb. 16, 2016.
Chinese Second Office Action in CN Application No. 201510257808.2, dated Oct. 26, 2016.
European Exam Report, re EP Application No. 09 791 510.2, dated Feb. 7, 2013.
European Exam Report, re EP Application No. 09 791 510.2, dated Apr. 2, 2014.
European Extended Search Report, re EP Application No. 14179199.6, dated Nov. 17, 2104.
Japanese Office Action, re JP Application No. JP 2011-523184, dated Jan. 14, 2014.
Japanese Office Action, re JP Application No. JP 2015-005005, dated Dec. 1, 2015.
Japanese Office Action, re JP Application No. JP 2015-005005, dated Sep. 6, 2016.
Korean Office Action, re KR Application No. 10-2014-7036395 (Original KR App. No. 10-2009-7016602), dated Mar. 20, 2015.
Korean Notice of Preliminary Rejection, re KR Application No. 10-2014-7036395 (Original KR App. No. 10-2009-7016602), dated Aug. 11, 2015.
Korean Notice of Preliminary Rejection, re KR Application No. 10-2015-7027964 (Original KR App. No. 10-2011-7005737), dated Dec. 1, 2015.
Korean Notice of Allowance, re KR Application No. 10-2015-7027964 (Original KR App. No. 10-2011-7005737), dated Mar. 24, 2016.
Mexican Office Action, re MX Application No. MX/a/2011/001708, dated Jul. 23, 2013.
International Search Report in Application No. PCT/US2009/053795 (now International Publication No. WO 2010/019830 A1), dated Dec. 18, 2009 (2 pages).
International Search Report and Written Opinion in Application No. PCT/US15/35400, dated Sep. 3, 2015. (23 pages).
International Preliminary Report on Patentability in Application No. PCT/US15/35400, dated Dec. 15, 2016. (14 pages).
U.S. Appl. No. 15/614,418, filed Jun. 5, 2017, Gomez-Galeno et al. San Diego, "Ligand Initiates Phase 1 Trial with Glucagon Receptor Antagonist for Type 2 Diatests," Diabetes Week, Nov. 25, 2013.
Vajda et al., "Pharmacokinetics and pharmacodynamics of single and multiple doses of the glucagon receptor antagonist LGD-6972 in healthy subjects and subjects with type 2 diabetes mellitus," Diabetes, Obesity and Metabolism, vol. 19, No. 1, Aug. 31, 2016.
European Extended Search Report re EP Application No. 15805822.2, dated Dec. 20, 2016.

\* cited by examiner

GLUCAGON ANTAGONISTS

CROSS-REFERENCE TO RELATED APPLICATIONS

This application claims benefit of U.S. Provisional Application No. 62/011,547, filed Jun. 12, 2014, U.S. Provisional Application No. 62/073,916, filed Oct. 31, 2014, and U.S. Provisional Application No. 62/078,926, filed Nov. 12, 2014 which are incorporated herein by reference in their entirety.

FIELD

Provided are antagonists of glucagon receptors. In particular, provided are compounds and compositions for use in treatment, prevention or amelioration of one or more symptoms of a glucagon receptor mediated disease or disorder.

BACKGROUND

Glucagon is a 29-amino acid pancreatic hormone which is secreted from the pancreatic a cells into the portal blood supply in response to hypoglycemia and acts as a counter-regulatory hormone to insulin. Most of the physiological effects of glucagon are mediated by its interaction with a glucagon receptor in the liver, followed by activation of adenylate cyclase to increase the intracellular cAMP levels. The result is an increase in glycogenolysis and gluconeogenesis, while attenuating the ability of insulin to inhibit these metabolic processes (Johnson et al., *J. Biol. Chem.* 1972, 247, 3229-3235). As such, the overall rates of hepatic glucose synthesis and glycogen metabolism are controlled by the systemic ratio of insulin and glucagon (Roden et al., *J. Clin. Invest.* 1996, 97, 642-648; Brand et al., *Diabetologia* 1994, 37, 985-993).

Diabetes is a disease characterized by elevated levels of plasma glucose. Uncontrolled hyperglycemia is associated with an increased risk for microvascular and macrovascular diseases, including nephropathy, retinopathy, hypertension, stroke, and heart disease. Control of glucose homeostasis is a major approach to the treatment of diabetes. It has been demonstrated in healthy animals as well as in animal models of types I and II diabetes that removal of circulating glucagon with selective and specific antibodies resulted in reduction of the glycemic level (Brand et al., *Diabetologia* 1994, 37, 985-993; Brand et al., *Diabetes* 1994, 43(Suppl. 1), 172A). Therefore, one of the potential treatments for diabetes and other diseases involving impaired glycemia is to block a glucagon receptor with a glucagon receptor antagonist to improve insulin responsiveness, to decrease the rate of gluconeogenesis, and/or to lower plasma glucose levels by reducing the rate of hepatic glucose output in a patient.

BRIEF SUMMARY

Provided herein are compounds, including enantiomerically pure forms thereof, and pharmaceutically acceptable salts or co-crystals and prodrugs thereof which have glucagon receptor antagonist or inverse agonist activity. Further, provided herein are pharmaceutical compositions comprising the same as well as methods of treating, preventing, delaying the time to onset or reducing the risk for the development or progression of a disease or condition for which one or more glucagon receptor antagonist is indicated, including without limitation Type I and II diabetes, insulin resistance and hyperglycemia. Moreover, provided herein are methods of making or manufacturing compounds disclosed herein, including enantiomerically pure forms thereof, and pharmaceutically acceptable salts or co-crystals and prodrugs thereof.

In one embodiment, the compounds have Formula I

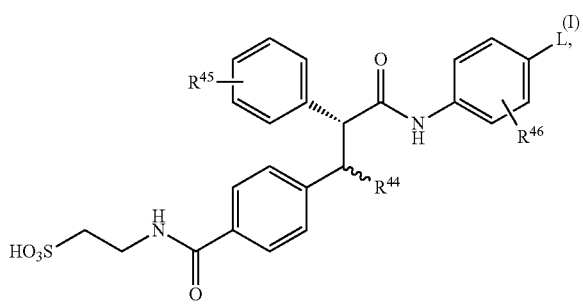

wherein:

$R^{44}$ is H, $CH_3$ or $CH_3CH_2$;

$R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or phenyl, any of which can be optionally substituted with one or more substituents;

L is phenyl, indenyl, benzoxazol-2-yl, $C_{3-6}$-cycloalkyl, $C_{4-8}$-cycloalkenyl or $C_{4-8}$-bicycloalkenyl, any of which can be optionally substituted with one or more substituents; and $R^{46}$ represents one or more substituents selected from H, F, Cl, $CH_3$, $CF_3$, $OCF_3$ or CN;

or a pharmaceutically acceptable salt, solvate, or prodrug thereof.

In another embodiment, the compounds have formula II

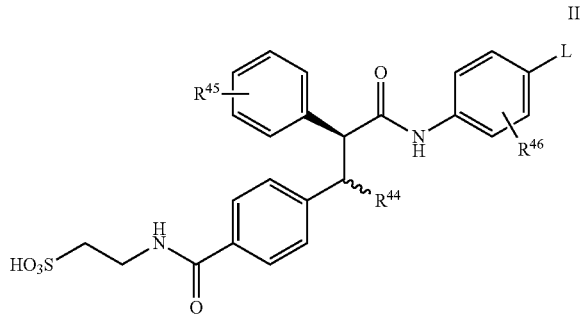

wherein:

$R^{44}$ is H, $CH_3$ or $CH_3CH_2$;

$R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or phenyl, any of which can be optionally substituted with one or more substituents;

L is phenyl, indenyl, benzoxazol-2-yl, $C_{3-6}$-cycloalkyl, $C_{4-8}$-cycloalkenyl or $C_{4-8}$-bicycloalkenyl, any of which can be optionally substituted with one or more substituents; and $R^{46}$ represents one or more substituents selected from H, F, Cl, $CH_3$, $CF_3$, $OCF_3$ or CN;

or a pharmaceutically acceptable salt, solvate, or prodrug thereof.

In another embodiment, the compounds have formula III

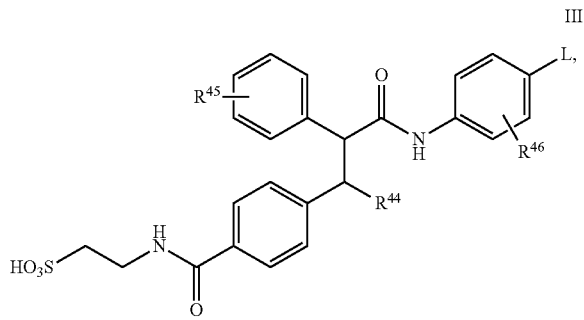

wherein:

R[44] is H;

R[45] is cis-4-t-butylcyclohexyl, trans-4-t-butylcyclohexyl, 4,4-dimethylcyclohexyl, (S)-4-t-butylcyclohexenyl, (R)-4-t-butylcyclohexenyl, 4,4-dipropylcyclohexenyl, (1R,4S)-1,7,7-trimethylbicyclo[2.2.1]-3-hept-2-enyl or (1R,4R)-1,7,7-trimethylbicyclo[2.2.1]-2-hept-2-enyl;

L is phenyl, benzoxazol-2-yl or 4,4-dimethylcyclohexenyl, any of which can be optionally substituted with one or more substituents; and R$_{46}$ is H;

or a pharmaceutically acceptable salt, solvate, or prodrug thereof.

Also provided herein are pharmaceutical compositions comprising a compound provided herein, e.g., a compound of Formula I, II or III, or a pharmaceutically acceptable salt, solvate, or prodrug thereof; in combination with one or more pharmaceutically acceptable carriers.

Further provided herein is a method of treating, preventing, or ameliorating one or more symptoms of a condition, disorder, or disease associated with a glucagon receptor, comprising administering to a subject having or being suspected to have such a condition, disorder, or disease, a therapeutically effective amount of a compound provided herein, e.g., a compound of Formula I, II or III, or a pharmaceutically acceptable salt, solvate, or prodrug thereof.

Additionally, provided herein is a method of treating, preventing, or ameliorating one or more symptoms of a condition, disorder, or disease responsive to the modulation of a glucagon receptor, comprising administering to a subject having or being suspected to have such a condition, disorder, or disorder, a therapeutically effective amount of a compound provided herein, e.g., a compound of Formula I, II or III, or a pharmaceutically acceptable salt, solvate, or prodrug thereof; or a pharmaceutical composition thereof.

Provided herein is a method of treating, preventing, or ameliorating one or more symptoms of a GCGR-mediated condition, disorder, or disease, comprising administering to a subject having or being suspected to have such a condition, disorder, or disease, a therapeutically effective amount of a compound provided herein, e.g., a compound of Formula I, II or III, or a pharmaceutically acceptable salt, solvate, or prodrug thereof; or a pharmaceutical composition thereof.

Provided herein is a method of treating, preventing, or ameliorating one or more symptoms of a condition, disorder, or disease responsive to a decrease in the hepatic glucose production or in the blood glucose level of a subject, comprising administering to the subject a therapeutically effective amount of a compound provided herein, e.g., a compound of Formula I, II or III, or a pharmaceutically acceptable salt, solvate, or prodrug thereof; or a pharmaceutical composition thereof.

Provided herein is a method of modulating the biological activity of a glucagon receptor, comprising contacting the receptor with one or more of the compounds provided herein, e.g., a compound of Formula I, II or III, or a pharmaceutically acceptable salt, solvate, or prodrug thereof; or a pharmaceutical composition thereof.

DETAILED DESCRIPTION a. Definitions

Figure 1:
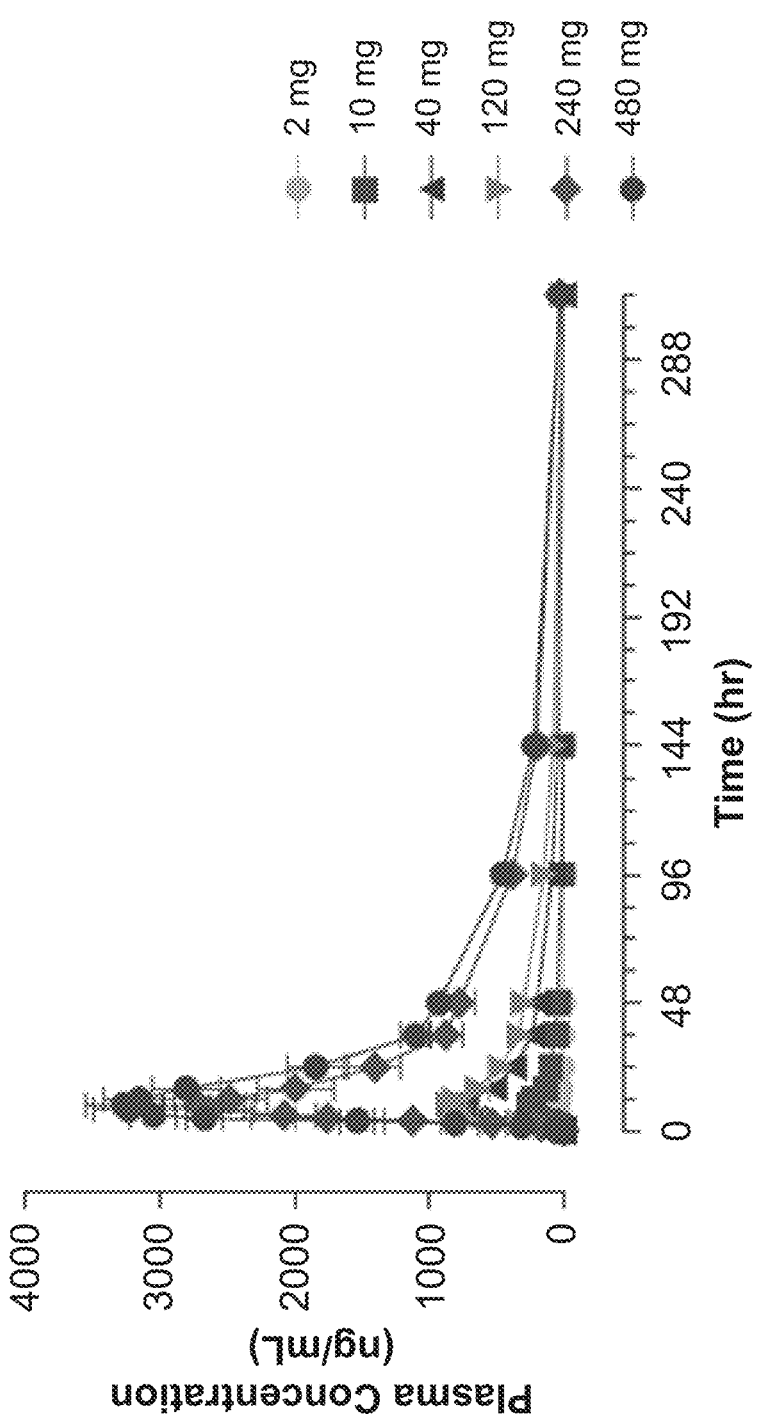
FIG. 1 shows the compound of Formula (IIIa) plasma concentration versus time following administration of 2 mg, 10 mg, 40 mg, 120 mg, 240 mg, and 480 mg, respectively, to normal healthy volunteers.
Figure 2:
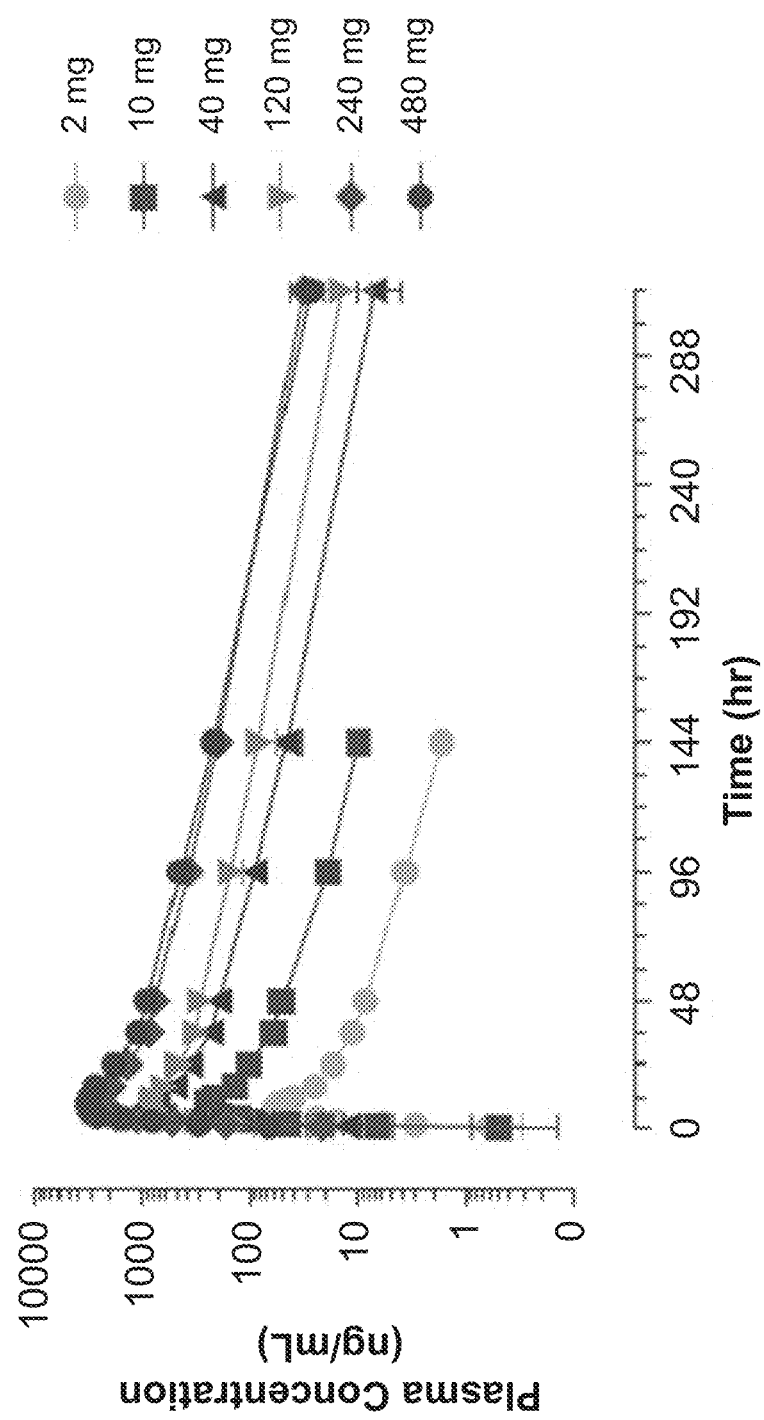
FIG. 2 shows the compound of Formula (IIIa) plasma concentration versus time following administration of 2 mg, 10 mg, 40 mg, 120 mg, 240 mg, and 480 mg, respectively, to normal healthy volunteers.
Figure 3:
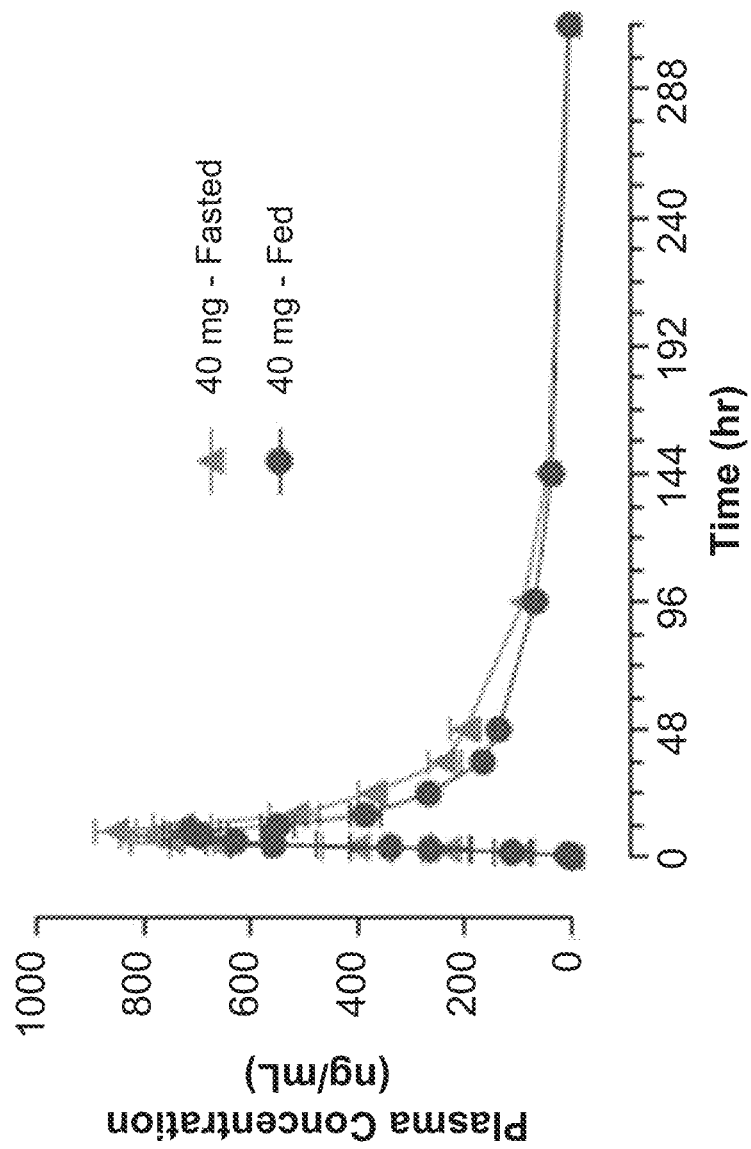
FIG. 3 shows the compound of Formula (IIIa) plasma concentration versus time following administration of 40 mg under fasted and fed conditions to normal healthy volunteers.
Figure 4:
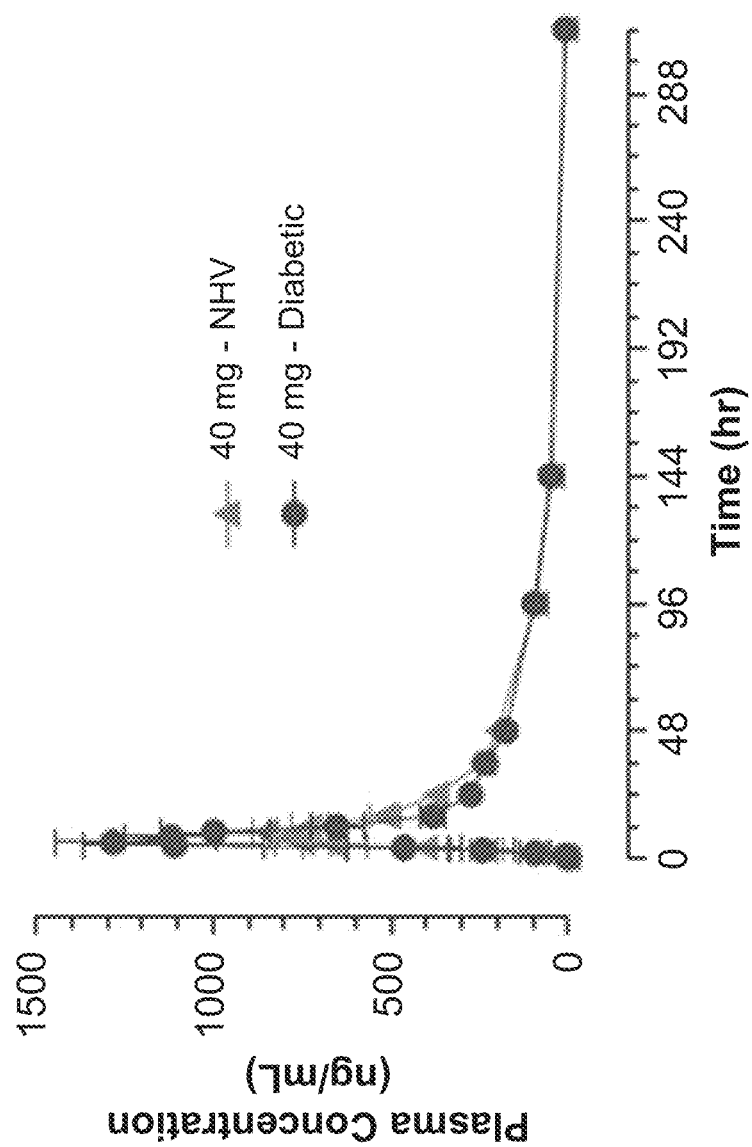
FIG. 4 shows the compound of Formula (IIIa) plasma concentration versus time following administration of 40 mg under fasted and fed conditions to T2DM subjects.
Figure 5B:
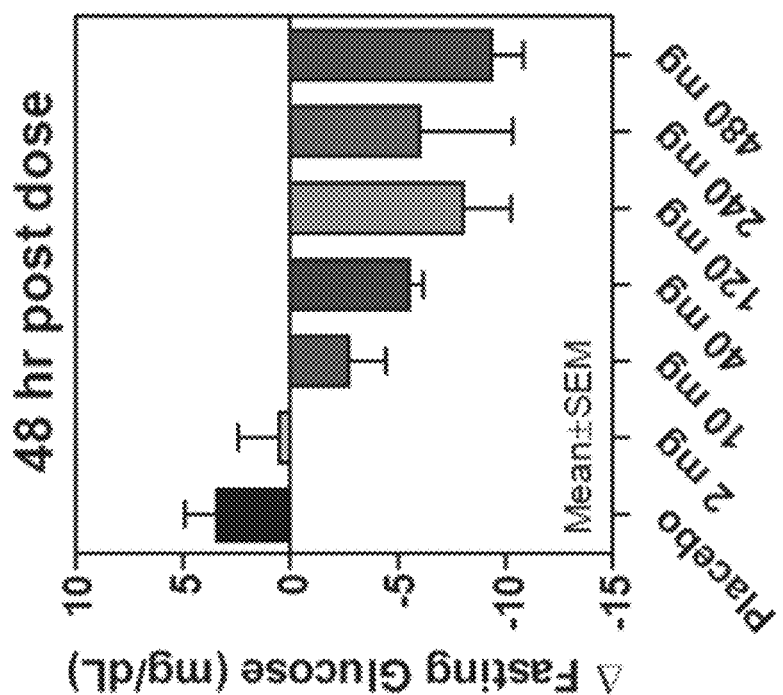
FIGS. 5A and 5B show changes in fasting plasma glucose at 24 hours post dose and 48 hours post dose, respectively, in normal healthy volunteers following administration of 2 mg, 10 mg, 40 mg, 120 mg, 240 mg, and 480 mg compound of Formula (IIIa) versus placebo.
Figure 5A:
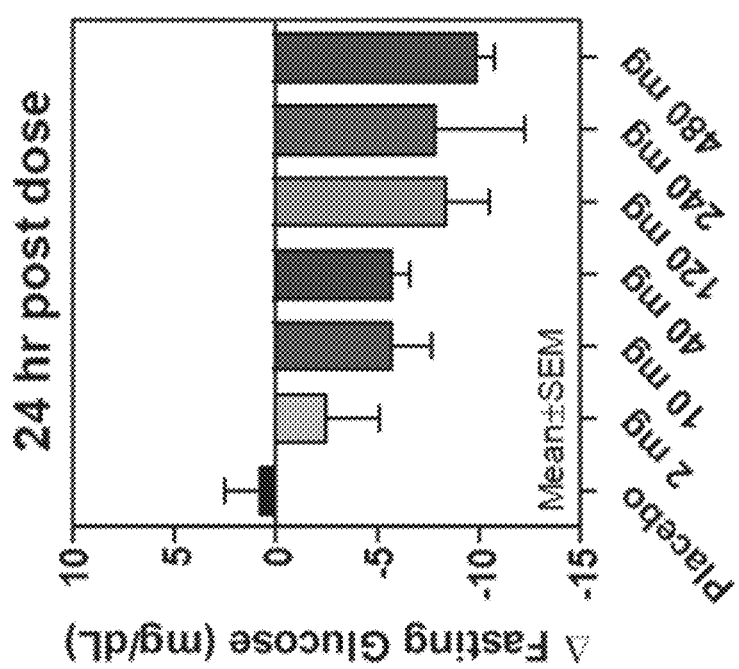
Figure 6B:
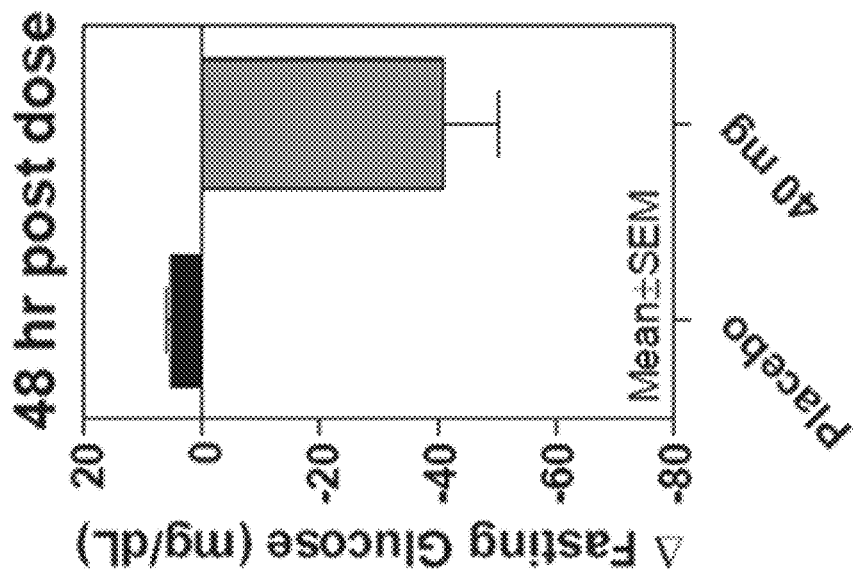
FIGS. 6A and 6B show changes in fasting plasma glucose at 24 hours post dose and 48 hours post dose, respectively, in T2DM subjects following administration of 40 mg compound of Formula (IIIa) versus placebo.
Figure 6A:
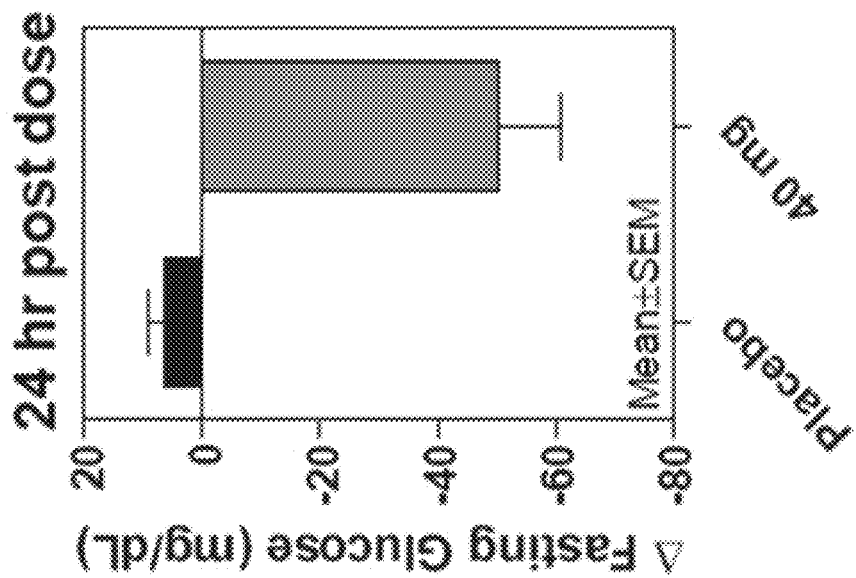
Figure 7:
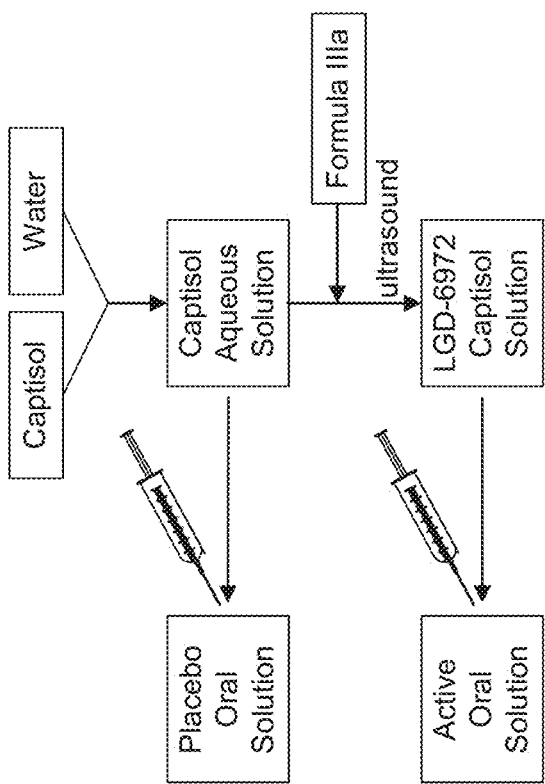
FIG. 7 shows a compounding scheme of preparing a placebo oral solution with Captisol® and an active oral solution with the compound of Formula IIIa (LGD-6972) and Captisol®.
Figure 8:
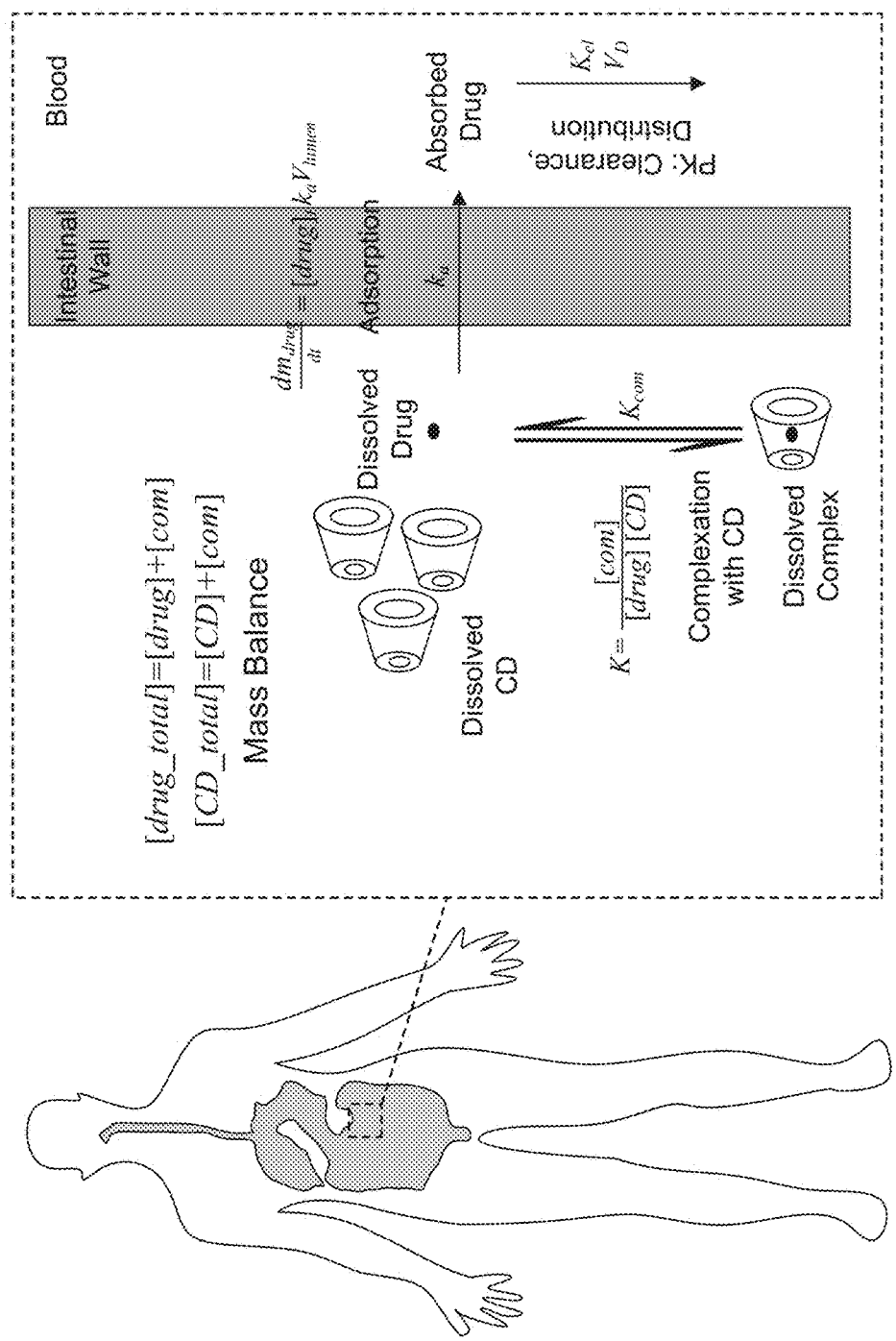
FIG. 8 illustrates a method of predicting pharmacokinetics of an oral dosing of the compound of Formula (IIIa) in an solution with cyclodextrin according to Gamsiz and Carrier et al., Biotechnol Bioeng (2010) 105:409-420.
Figure 9:
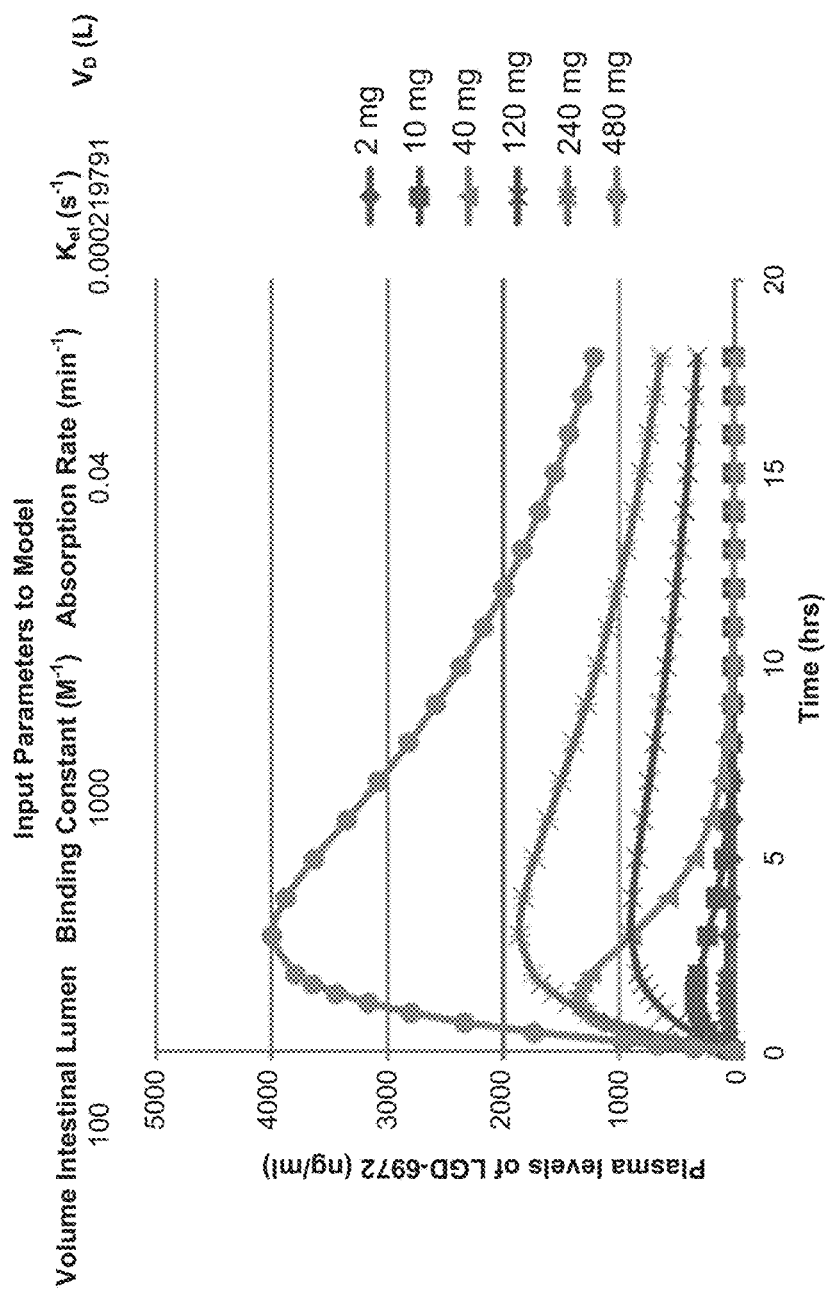
FIG. 9 shows a model prediction of the compound of Formula (IIIa) plasma concentration versus time following administration of 2 mg, 10 mg, 40 mg, 120 mg, 240 mg, and 480 mg, respectively, and a calculation of the complex stability constant (binding constant) of the compound of Formula (IIIa) (LGD-6972) with Captisol®.
Figure 10:
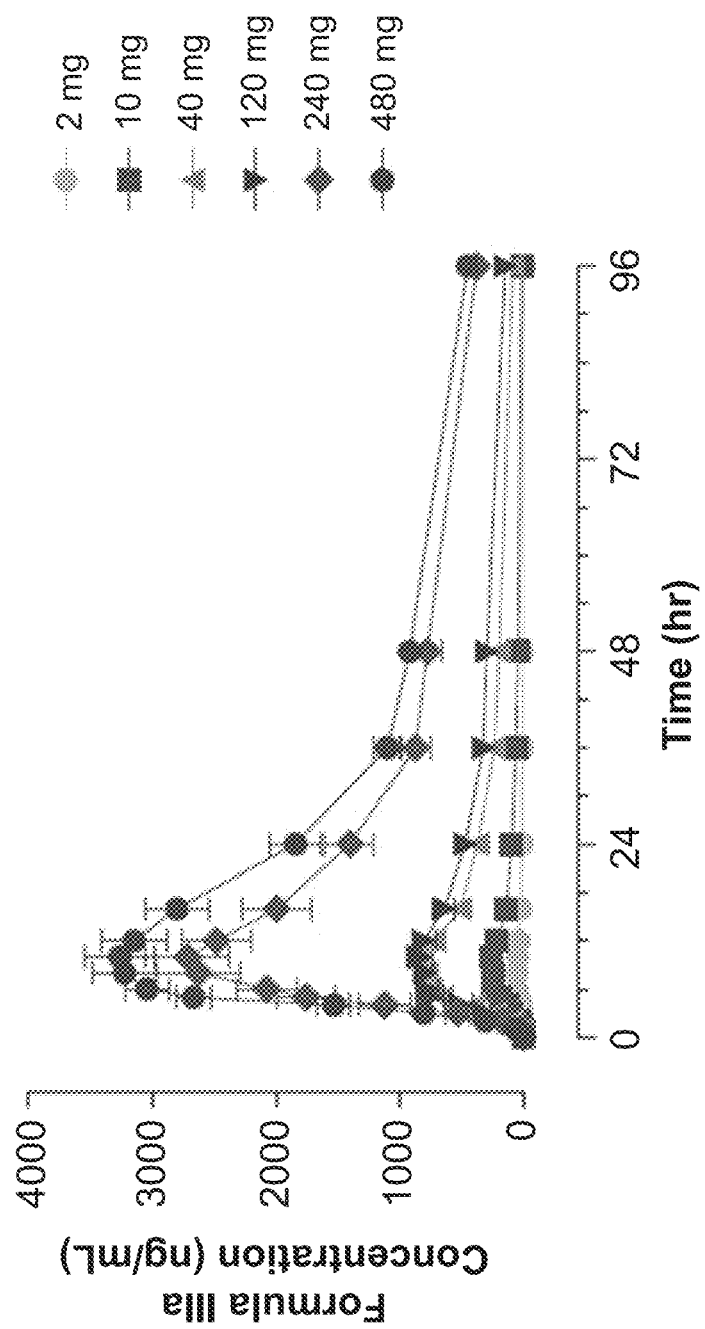
FIG. 10 shows the compound of Formula (IIIa) plasma concentration versus time following oral administration of 2 mg, 10 mg, 40 mg, 120 mg, 240 mg, and 480 mg, respectively.

To facilitate understanding of the disclosure set forth herein, a number of terms are defined below, Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician, The term "$IC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st Edition, Lippincott Williams & Wilkins: Philadelphia, Pa., 2005; Handbook of Pharmaceutical Excipients, 5th Edition, Rowe et al., Eds., The Pharmaceutical Press and the American Pharmaceutical Association: 2005; and Handbook of Pharmaceutical Additives, 3rd Edition, Ash and Ash Eds., Gower Publishing Company: 2007; Pharmaceutical Preformulation and Formulation, Gibson Ed., CRC Press LLC: Boca Raton, Fla., 2004.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "glucagon receptor" or "GCGR" refers to a glucagon receptor protein or variant thereof, which is capable of mediating a cellular response to glucagon in vitro or in vivo. GCGR variants include proteins substantially homologous to a native GCGR, i.e., proteins having one or more naturally or non-naturally occurring amino acid deletions, insertions, or substitutions (e.g., GCGR derivatives, homologs, and fragments), as compared to the amino acid sequence of a native GCGR. In certain embodiments, the amino acid sequence of a GCGR variant is at least about 80% identical, at least about 90% identical, or at least about 95% identical to a native GCGR. In certain embodiments, the GCGR is a human glucagon receptor.

The term "glucagon receptor antagonist" or "GCGR antagonist" refers to a compound that, e.g., partially or completely blocks, decreases, prevents, inhibits, or downregulates GCGR activity. There terms also refer to a compound that binds to, delays the activation of, inactivates, or desensitizes GCGR. A GCGR antagonist may act by interfering with the interaction of glucagon with GCGR.

The term "GCGR-mediated condition, disorder, or disease" refers to a condition, disorder, or disease characterized by inappropriate, e.g., less than or greater than normal, GCGR activity. Inappropriate GCGR functional activity might arise as the result of an increase in glucagon concentration, GCGR expression in cells which normally do not express GCGR, increased GCGR expression or degree of intracellular activation, leading to, e.g., abnormal plasma glucose levels; or decreased GCGR expression. A GCGR-mediated condition, disorder or disease may be completely or partially mediated by inappropriate GCGR activity. In particularly, a GCGR-mediated condition, disorder or disease is one in which modulation of GCGR results in some effect on the underlying condition, disorder, or disease, e.g., a GCGR antagonist results in some improvement in at least some of patients being treated.

The term "alkyl" and the prefix "alk" refers to a linear or branched saturated monovalent hydrocarbon radical, wherein the alkyl may optionally be substituted with one or more substituents. The term "alkyl" also encompasses linear, branched, and cyclic alkyl, unless otherwise specified. In certain embodiments, the alkyl is a linear saturated monovalent hydrocarbon radical that has 1 to 20 (C1-20), 1 to 15 (C1-15), 1 to 12 (C1-12), 1 to 10 (C1-10), or 1 to 6 (C1-6) carbon atoms, or branched saturated monovalent hydrocarbon radical of 3 to 20 (C3-20), 3 to 15 (C3-15), 3 to 12 (C3-12), 3 to 10 (C3-10), or 3 to 6 (C3-6) carbon atoms. As used herein, linear C1-6 and branched C3-6 alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, C1-6 alkyl refers to a linear saturated monovalent hydrocarbon radical of 1 to 6 carbon atoms or a branched saturated monovalent hydrocarbon radical of 3 to 6 carbon atoms. Cycloalkyl also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

The term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also embraces radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, C2-6 alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 (C2-20), 2 to 15 (C2-15), 2 to 12 (C2-12), 2 to 10 (C2-10), or 2 to 6 (C2-6) carbon atoms, or a branched monovalent hydrocarbon radical of 3 to 20 (C3-20), 3 to 15 (C3-15), 3 to 12 (C3-12), 3 to 10 (C3-10), or 3 to 6 (C3-6) carbon atoms. Examples of alkenyl groups include, but are not limited to, vinyl, isopropenyl, pentenyl, hexenyl, heptenyl, ethenyl, propen-1-yl, propen-2-yl, allyl, butenyl, 2-butenyl, 2-methyl-2-butenyl, 4-methylbutenyl, and the like.

The term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 (C2-20), 2 to 15 (C2-15), 2 to 12 (C2-12), 2 to 10 (C2-10), or 2 to 6 (C2-6) carbon atoms, or a branched monovalent hydrocarbon radical of 3 to 20 (C3-20), 3 to 15 (C3-15), 3 to 12 (C3-12), 3 to 10 (C3-10), or 3 to 6 (C3-6) carbon atoms. Examples of alkynyl groups include, but are not limited to, ethynyl (—C≡CH), propargyl (—CH2C≡CH), 3-methyl-1-pentynyl, 2-heptynyl, and the like. For example, C2-6 alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted with one or more substituents. In certain embodiments, the cycloalkyl has from 3 to 20 (C3-20), from 3 to 15 (C3-15), from 3 to 12 (C3-12), from 3 to 10 (C3-10), or from 3 to 7 (C3-7) carbon atoms. Examples of cycloalkyl groups include, but are not limited to, cyclopropyl, cyclobutyl, cyclopentyl, cyclohexyl, cycloheptyl, decalinyl, and adamantyl.

The term "cycloalkenyl" refers to a cyclic unsaturated bridged and/or non-bridged monovalent hydrocarbon radical, which contains one or more double bonds in its ring. The cycloalkenyl may be optionally substituted with one or more substituents. In certain embodiments, the cycloalkenyl has from 3 to 20 (C3-20), from 3 to 15 (C3-15), from 3 to 12 (C3-12), from 3 to 10 (C3-10), or from 3 to 7 (C3-7) carbon atoms.

The term "cycloalkynyl" refers to a cyclic unsaturated bridged and/or non-bridged monovalent hydrocarbon radical, which contains one or more triple bonds in its ring. The cycloalkynyl may be optionally substituted with one or more substituents. In certain embodiments, the cycloalkynyl has from 3 to 20 (C3-20), from 3 to 15 (C3-15), from 3 to 12 (C3-12), from 3 to 10 (C3-10), or from 3 to 7 (C3-7) carbon atoms.

The term "aryl" (Ar) refers to a monocyclic aromatic group and/or multicyclic monovalent aromatic group that contain at least one aromatic hydrocarbon ring. In certain embodiments, the aryl has from 6 to 20 (C6-20), from 6 to 15 (C6-15), or from 6 to 10 (C6-10) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents.

The term "aralkyl" or "aryl-alkyl" refers to a monovalent alkyl group substituted with aryl. In certain embodiments, both alkyl and aryl may be optionally substituted with one or more substituents.

The term "heteroaryl" (HAR) refers to a monocyclic aromatic group and/or multicyclic aromatic group that contain at least one aromatic ring, wherein at least one aromatic ring contains one or more heteroatoms independently selected from O, S, and N. In some embodiments, each ring contains 5 to 6 atoms. Each ring of a heteroaryl group can contain one or two 0 atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyramidyl, pyridazinyl, triazolyl, tetrazolyl, and triazinyl. Examples of bicyclic heteroaryl groups include, but are not limited to, indolyl, benzothiazolyl, benzoxazolyl, benzothienyl, benzothiophenyl, furo(2,3-b) pyridyl, quinolinyl, tetrahydroisoquinolinyl, isoquinolyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, heteroaryl may also be optionally substituted with one or more substituents. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

The term "heterocyclyl" (Hetcy) or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may includes a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, □-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, 2,3-dihydrofuro(2,3-b)pyridyl, dihydrofuryl, dihydroindolyl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxixanyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydrohydroquinolinyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. Heterocyclyl/heterocyclic also includes partially unsaturated monocyclic rings that are not aromatic, such sa 2- or 4-pyridones attached through the nitrogen or N-substituted-(1H,3H)-pyrimidine-2,4-diones (N-substituted uracils). Heterocyclyl/heterocyclic also includes such moieties in charged form, e.g., piperidinium. In certain embodiments, heterocyclyl/heterocyclic may also be optionally substituted with one or more substituents.

The term "alkoxy" refers to an —OR radical, wherein R is, for example, alkyl, alkenyl, alkynyl, cycloalkyl, aryl, heteroaryl, or heterocyclyl, each as defined herein. When R is aryl, it is also known as aryloxy. Examples of alkoxy groups include, but are not limited to, methoxy, ethoxy, propoxy, n-propoxy, 2-propoxy, n-butoxy, isobutoxy, tert-butoxy, cyclohexyloxy, phenoxy, benzoxy, and 2 naphthyloxy. In certain embodiments, alkoxy may also be optionally substituted with one or more substituents.

The term "acyl" refers to a —C(O)R radical, wherein R is, for example, hydrogen, alkyl, alkenyl, alkynyl, cycloalkyl, aryl, heteroaryl, or heterocyclyl, each as defined herein. Examples of acyl groups include, but are not limited to, formyl, acetyl, propionyl, butanoyl, isobutanoyl, pentanoyl, hexanoyl, heptanoyl, octanoyl, nonanoyl, decanoyl, dodecanoyl, tetradecanoyl, hexadecanoyl, octadecanoyl, eicosanoyl, docosanoyl, myristoleoyl, palmitoleoyl, oleoyl, linoleoyl, arachidonoyl, benzoyl, pyridinylcarbonyl, and furoyl. In certain embodiments, acyl may also be optionally substituted with one or more substituents.

The term "halogen", "halide" or "halo" (Halo) refers to fluorine, chlorine, bromine, and/or iodine.

The term "optionally substituted" is intended to mean that a group, including alkyl, alkoxy, acyl, alkyl-cycloalkyl, hydroxyalkyl, alkenyl, alkynyl, cycloalkyl, cycloalkenyl, cycloalkynyl, cycloalkylalkyl, aryl, aryloxy, aralkyl, aryl-alkenyl, aryl-alkynyl, heteroaryl, heteroarylalkyl, heteroaryl-alkenyl, heteroaryl-alkynyl, and heterocyclyl, or acyl, may be substituted with one or more substituents, in one embodiment, one, two, three, four substituents, where in some embodiments each substituent is independently selected from the group consisting of cyano, halo, oxo, nitro, $C_{1-6}$ alkyl, $C_{2-6}$alkenyl, $C_{2-6}$alkynyl, $C_{3-7}$cycloalkyl, $C_{6-14}$aryl, heteroaryl, heterocyclyl, —C(O)R$^c$, —C(O)OR$^c$, —C(O)NR$^f$R$^8$, —C(NR$^c$)NR$^f$R$^8$, —OR$^c$, —OC(O)R$^c$, —OC(O)OR$^e$, —OC(O)NR$^f$R$^8$, —OC(=NR$^e$)NR$^f$R$^8$, —(OS)(O)R$^c$, —OS(O)$_2$R$^e$, —OS(O)NR$^f$R$^8$, —OS(O)$_2$NR$^f$R$^g$, —NR$^f$R$^g$, —NR$^e$C(O)R$^f$, —NR$^e$C(O)OR$^f$, —NR$^e$C(O)NR$^f$R$^g$, NR$^e$C(=NR)NR$^f$R$^g$, —NR$^e$S(O)R$^f$, —NR$^e$S(O)$_2$R$^f$, —NR$^e$S(O)NR$^f$R$^g$, —NR$^e$S(O)$_2$NR$^f$R$^g$, —SR$^e$, —S(O)R$^e$, —S(O)$_2$R$^e$, and —S(O)$_2$NR$^f$R$^g$, wherein each R$^e$, R$^f$, R$^g$, and R$^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or R$^f$ and R$^g$ together with the N atom to which they are attached form heterocyclyl.

The term "optically active" refers to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise, However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

"Binding" means the specific association of the compound of interest to the target of interest, e.g., a receptor.

The term "crystalline" and related terms used herein, when used to describe a substance, component or product, means that the substance, component or product is crystalline as determined by X-ray diffraction. See, e.g., *Reming-* ton's *Pharmaceutical Sciences,* 18'h ed., Mack Publishing, Easton Pa., 173 (1990); *The United States Pharmacopeia,* 23*rd* ed., 1843-1844 (1995).

"Co-crystal" as used herein means a crystalline material comprised of two or more unique solids at room temperature that are H-bonded.

"Diabetes" refers to a heterogeneous group of disorders that share impaired glucose tolerance in common. It may be characterized by hyperglycemia, glycosuria, ketoacidosis, neuropathy or nephropathy, increased hepatic glucose production, insulin resistance in various tissues, insufficient insulin secretion and enhanced or poorly controlled glucagon secretion from the pancreas.

The vast majority of cases of diabetes fall into two broad etiopathogenetic categories. In one category, type 1 diabetes, the cause is a deficiency of insulin secretion. In the other, more prevalent category, type 2 diabetes, the cause is resistance to insulin action and/or an inadequate compensatory insulin secretory response. In the latter category, a degree of hyperglycemia sufficient to cause pathologic and functional changes in various target tissues, but without clinical symptoms, may be present for a long period of time before diabetes is detected. During this asymptomatic period, it is possible to demonstrate an abnormality in carbohydrate metabolism by measurement of elevated plasma glucose in the fasting state or after a challenge with an oral glucose load. Diabetes may also appear during pregnancy (gestational diabetes or GDM).

Criteria for the diagnosis of diabetes include:

1. Symptoms of diabetes plus casual plasma glucose concentration 200 mg/dl (11.1 mmol/l). Casual is defined as any time of day without regard to time since last meal. The classic symptoms of diabetes include polyuria, polydipsia, and unexplained weight loss; or
2. Fasting plasma glucose (FPG) concentration of 126 mg/dl (7.0 mmol/1). Fasting is defined as no caloric intake for at least 8 h; or
3. 2-h postmeal or postload (during an oral glucose tolerance test (OGTT) glucose concentration of 200 mg/dl (11.1 mmol/l)

The term "drug" refers to a compound, or a pharmaceutical composition thereof, which is administered to a subject for treating, preventing, or ameliorating one or more symptoms of a condition, disorder, or disease.

The term "$EC_{50}$" refers an amount, concentration, or dosage of a compound at which 50% of a maximal response is observed in an assay that measures such response.

The term "percent enantiomeric excess (% ee)" refers to optical purity. It is obtained by using the following formula:

$$\frac{[R]-[S]}{[R]+[S]} \times 100 = \% \ R - \% \ S$$

where [R] is the amount of the R isomer and [S] is the amount of the S isomer. This formula provides the % ee when R is the dominant isomer.

The term "enantiomerically pure" refers to a compound which comprises at least about 80% by weight of the designated enantiomer and at most about 20% by weight of the other enantiomer or other stereoisomer(s), at least about 90% by weight of the designated enantiomer and at most about 10% by weight of the other enantiomer or other stereoisomer(s), at least about 95% by weight of the designated enantiomer and at most about 5% by weight of the other enantiomer or other stereoisomer(s), at least about 96.6% by weight of the designated enantiomer and at most about 3.4% by weight of the other enantiomer or other stereoisomer(s), at least about 97% by weight of the designated enantiomer and at most about 3% by weight of the other enantiomer or other stereoisomer(s), at least about 99% by weight of the designated enantiomer and at most about 1% by weight of the other enantiomer or other stereoisomer(s), or at least about 99.9% by weight of the designated enantiomer and at most about 0.1% by weight of the other enantiomer or other stereoisomer(s). In certain embodiments, the weights are based upon total weight of the compound.

As used in connection with the compounds of Formula I and III disclosed herein, the terms "R-isomer" and "R-enantiomer" refer to the configuration R of the aliphatic carbon which is alpha to the —C(O)NH— group. Formula I below shows the R-stereochemistry.

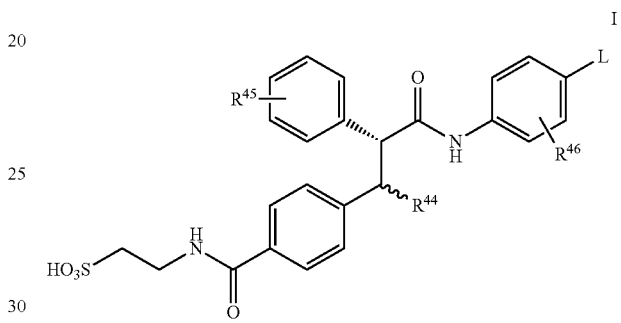

As used in connection with the compounds of Formula II and III disclosed herein, the terms "S-isomer" and "S-enantiomer" refer to the configuration S of the aliphatic carbon which is alpha to the —C(O)NH— group. Formula II below shows the S-stereochemistry.

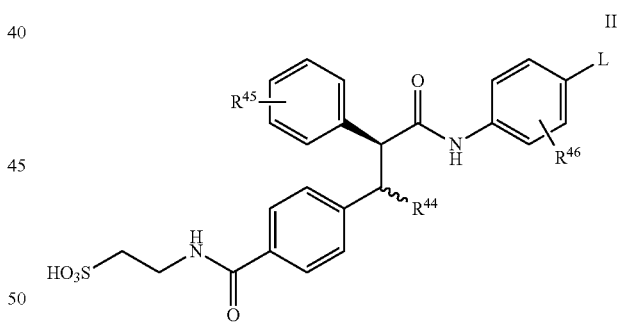

The term "chiral" as used herein includes a compound that has the property that it is not superimposable on its mirror image.

"Hypercholesterolemia" refers to presence of an abnormally large amount of cholesterol in the cells and plasma of the circulating blood.

"Hyperinsulinemia" refers to a patient with a fasting serum insulin concentration of at least 12 μU/mL.

"Hyperlipidemia" or "lipemia" refers to the presence of an abnormally large amount of lipids in the circulating blood.

"Insulin resistance" is defined clinically as the impaired ability of a known quantity of exogenous or endogenous insulin to increase whole body glucose uptake and utilization.

"Impaired glucose tolerance (IGT)" refers to a condition known to precede the development of overt Type 2 diabetes. It is characterized by abnormal blood glucose excursions following a meal. The current criteria for the diagnosis of IGT are based on 2-h plasma glucose levels post a 75 g oral glucose test (144-199 mg/dL). Although variable from population to population studied, IGT progresses to full-blown NIDDM at a rate of 1.5 to 7.3% per year, with a mean of 3-4% per year. Individuals with IGT are believed to have a 6 to 10-fold increased risk in developing Type 2 diabetes, IGT is an independent risk factor for the development of cardiovascular disease.

"Lower" referred to herein in connection with organic radicals or compounds respectively defines such radicals or compounds as containing up to and including 6 carbon atoms. One aspect provides organic radicals or compounds as containing up to and including 4 carbon atoms. Yet another aspect provides organic radicals or compounds that contain one to three carbon atoms. Such groups may be straight chain, branched, or cyclic.

"Metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary artery disease, cardiovascular disease.

"Metabolic Syndrome" or "Metabolic Syndrome X" refers to a condition identified by the presence of three or more of these components:
 Central obesity as measured by waist circumference:
  Men: Greater than 40 inches
  Women: Greater than 35 inches
 Fasting blood triglycerides greater than or equal to 150 mg/dL
 Blood HDL cholesterol:
  Men: Less than 40 mg/dL
  Women: Less than 50 mg/dL
 Blood pressure greater than or equal to 130/85 mmHg
 Fasting blood glucose greater than or equal to 110 mg/dL "Obesity" refers to the condition of being obese. Being obese is defined as a BMI of 30.0 or greater; and extreme obesity is defined at a BMI of 40 or greater. "Overweight" is defined as a body mass index of 25.0 to 29.9.

"Prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, —NHR, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I, II or III disclosed herein fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

b. Compounds

One aspect provides for compounds of Formula I

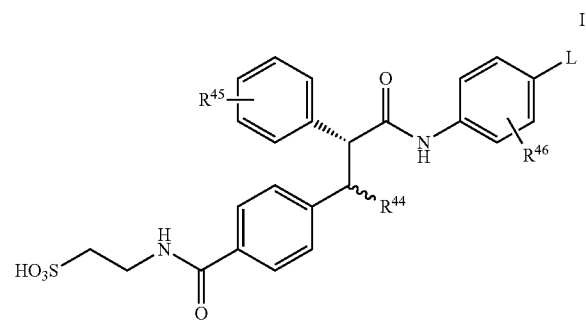

wherein:
 $R^{44}$ is H, $CH_3$ or $CH_3CH_2$;
 $R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or phenyl, any of which can be optionally substituted with one or more substituents;
 L is phenyl, indenyl, benzoxazol-2-yl or 4,4-dimethylcyclohexenyl, any of which can be optionally substituted with one or more substituents; and
 $R^{46}$ represents one or more substituents selected from H, F, Cl, $CH_3$, $CF_5$, $OCF_3$ or CN.

In certain embodiments according to Formula I, the configuration of the aliphatic carbon which is alpha to the —C(O)NH— group is R.

In certain embodiments according to Formula I, L is substituted with one or more substituents independently selected from F, Cl, $CH_3$, $CF_3$, $OCF_3$ or CN.

In another embodiment, L is phenyl, benzoxazol-2-yl or 4,4-dimethylcyclohexanyl, any of which can be optionally substituted with one or more substituents. In another embodiment, L is 4-chloro-2-methylphenyl, 4-methyl-2-benzoxazolyl, 2,4,6-trimethylphenyl, 2-benzoxazolyl, 4-chloro-3-methylphenyl or 4,4-dimethylcyclohexenyl.

In another embodiment, $R^{44}$ is H or $CH_3$. In another embodiment, $R^{44}$ is H.

In certain embodiments, $R^{45}$ is attached to the 3 (meta) or 4 (para) position. In another embodiment, $R^{45}$ is attached to the 4 (para) position.

In another embodiment, $R^{45}$ is alkenyl, $C_{3-6}$-cycloalkyl, $C_{4-8}$-cycloalkenyl, $C_{4-8}$-bicycloalkenyl or phenyl, any of which can be optionally substituted with one or more substituents.

In certain embodiments according to Formula I, $R^{45}$ is optionally substituted and is selected from $(CH_3)_3CCH=CH-$, t-butyl-cycloalkyl-, dimethyl-cycloalkyl-, t-butyl-cycloalkenyl-, dimethyl-cycloalkenyl-, bicycloalkenyl or phenyl-.

In certain embodiments according to Formula I, $R^{45}$ is substituted with one or more substituents independently selected from $CH_3$ and $(CH_3)_3C-$.

In certain embodiments according to Formula I, $R^{45}$ is trans-t-butylvinyl, cis-4-t-butylcylcohex butylcyclohexyl, trans-4-t-butylcyclohexyl, 4,4-dimethylcyclohexyl, cyclohexenyl, (S)-4-t-butylcyclohexenyl, (R)-4-t-butylcyclohexenyl, 4,4-dimethylcyclohexenyl, 4,4-diethylcyclohexenl, diethylcyclohexenyl, 4,4-diethylcyclohexyl, 4,4-dipropylcyclohexyl, 4,4-dipropylcyclohexeny, 4,4-dimethylcyclohexadienyl, (1R,4S)-1,7,7-trimethylbicyclo[2.2.1]3-heptyl-2-ene, (1R,4R)-1,7,7-trimethylbicyclo[2.2.1]2-heptyl-2-ene, 2-methyl-4-chloro-phenyl, 2,4,6 trimethylphenyl or 4-t-butylphenyl.

In certain embodiments according to Formula I, $R^{45}$ is trans-t-butylvinyl, cis 4-butylcyclohexyl, trans-4-t-butylcyclohexyl, 4,4-dimethylcyclohexyl, (S)-4-t-butylcyclohexenyl. (R)-4-t-butylcyclohexenyl, 4,4-dimethylcyclohexenyl, (1R,4R) 1,7,7-trimethylbicyclo [2.2.1]2-heptyl-2-ene or 4-t-butylphenyl.

In another embodiment, $R^{46}$ is H or $CH_3$. In another embodiment, $R^{46}$ is H.

In certain embodiments, the compound of Formula I is selected from the group presented in Table I:

TABLE 1

Compounds of Formula I

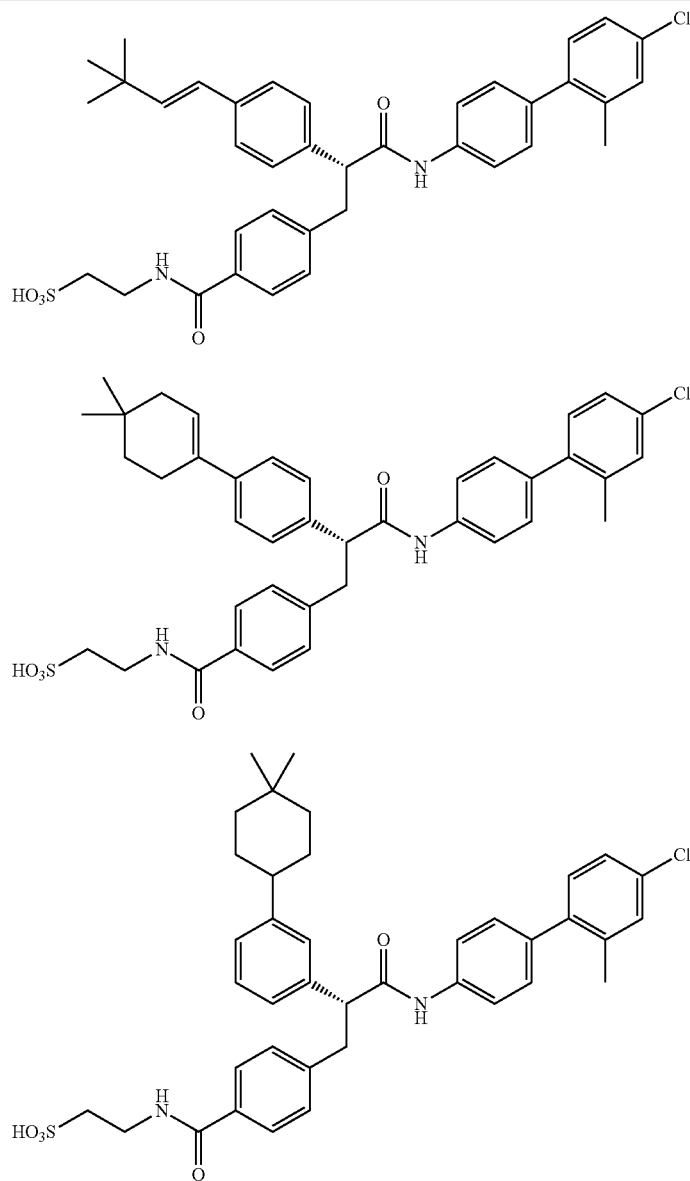

TABLE 1-continued
Compounds of Formula I
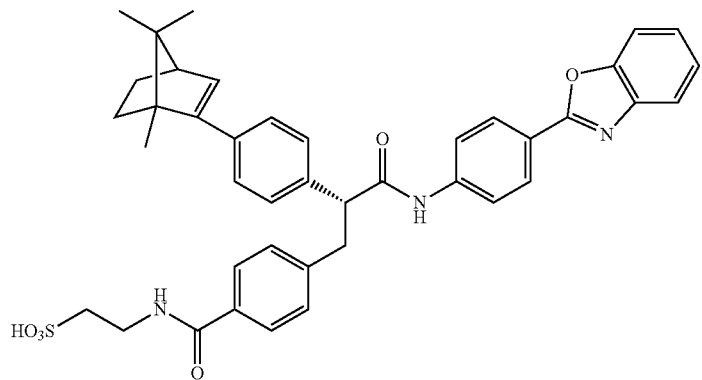 [SMILES: CC12CCC(C=C1c1ccc([C@@H](Cc3ccc(C(=O)NCCS(=O)(=O)O)cc3)C(=O)Nc3ccc(-c4nc5ccccc5o4)cc3)cc1)C2(C)C]
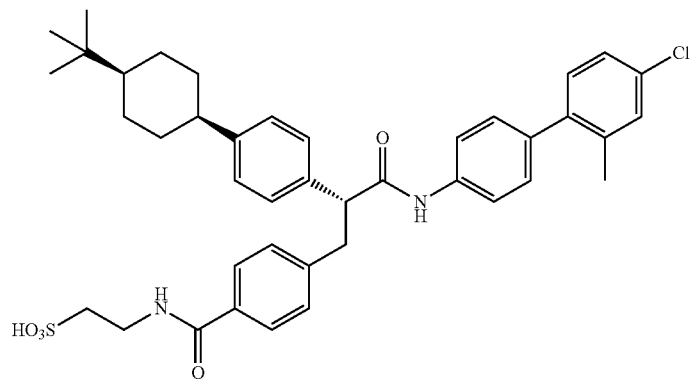 [SMILES: Cc1cc(Cl)ccc1-c1ccc(NC(=O)[C@H](Cc2ccc(C(=O)NCCS(=O)(=O)O)cc2)c2ccc([C@H]3CC[C@@H](C(C)(C)C)CC3)cc2)cc1]
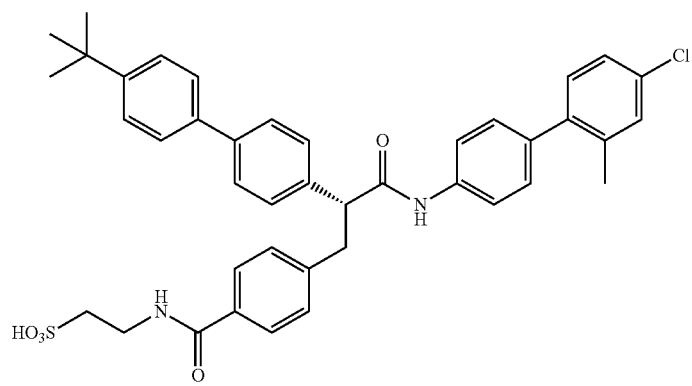 [SMILES: Cc1cc(Cl)ccc1-c1ccc(NC(=O)[C@H](Cc2ccc(C(=O)NCCS(=O)(=O)O)cc2)c2ccc(-c3ccc(C(C)(C)C)cc3)cc2)cc1]
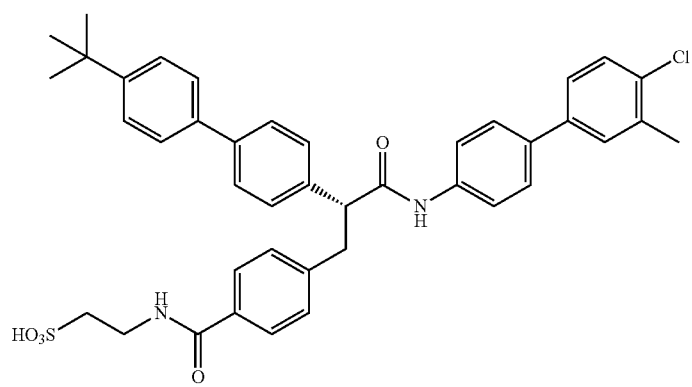 [SMILES: Cc1cc(-c2ccc(NC(=O)[C@H](Cc3ccc(C(=O)NCCS(=O)(=O)O)cc3)c3ccc(-c4ccc(C(C)(C)C)cc4)cc3)cc2)ccc1Cl]

TABLE 1-continued
Compounds of Formula I
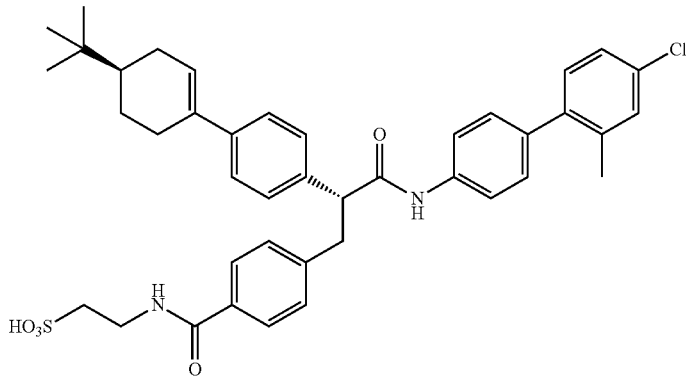 [SMILES: Cc1cc(Cl)ccc1-c1ccc(NC(=O)[C@H](Cc2ccc(C(=O)NCCS(=O)(=O)O)cc2)c2ccc(C3=CC[C@H](C(C)(C)C)CC3)cc2)cc1]
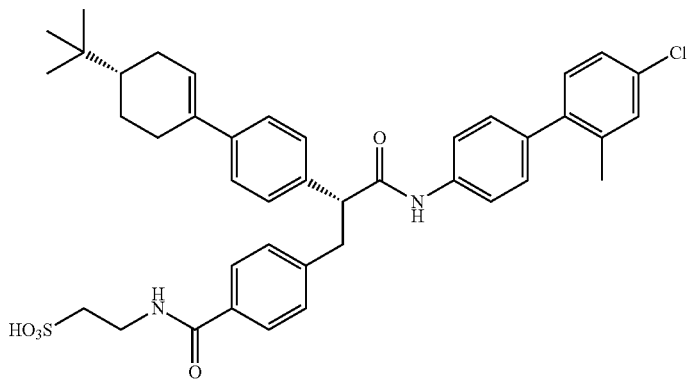 [SMILES: Cc1cc(Cl)ccc1-c1ccc(NC(=O)[C@H](Cc2ccc(C(=O)NCCS(=O)(=O)O)cc2)c2ccc(C3=CC[C@@H](C(C)(C)C)CC3)cc2)cc1]
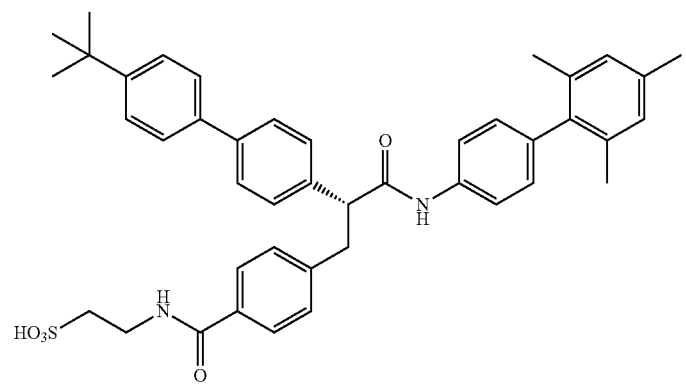 [SMILES: Cc1cc(C)c(-c2ccc(NC(=O)[C@H](Cc3ccc(C(=O)NCCS(=O)(=O)O)cc3)c3ccc(-c4ccc(C(C)(C)C)cc4)cc3)cc2)c(C)c1]
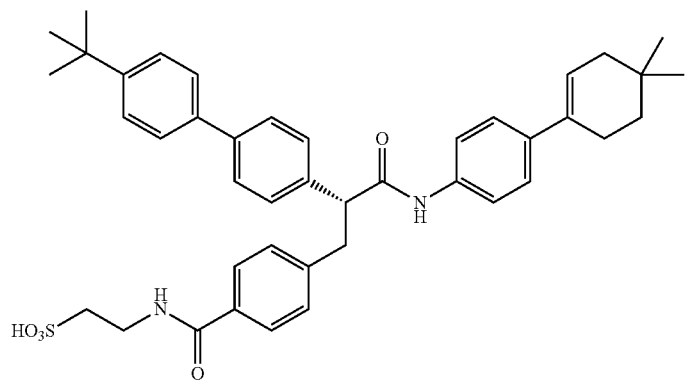 [SMILES: CC1(C)CC=C(c2ccc(NC(=O)[C@H](Cc3ccc(C(=O)NCCS(=O)(=O)O)cc3)c3ccc(-c4ccc(C(C)(C)C)cc4)cc3)cc2)CC1]

TABLE 1-continued

Compounds of Formula I

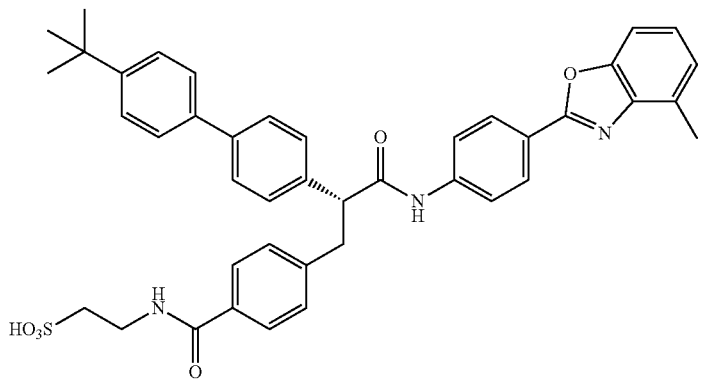 [SMILES: Cc1cccc2oc(-c3ccc(NC(=O)[C@H](Cc4ccc(C(=O)NCCS(=O)(=O)O)cc4)c4ccc(-c5ccc(C(C)(C)C)cc5)cc4)cc3)nc12]

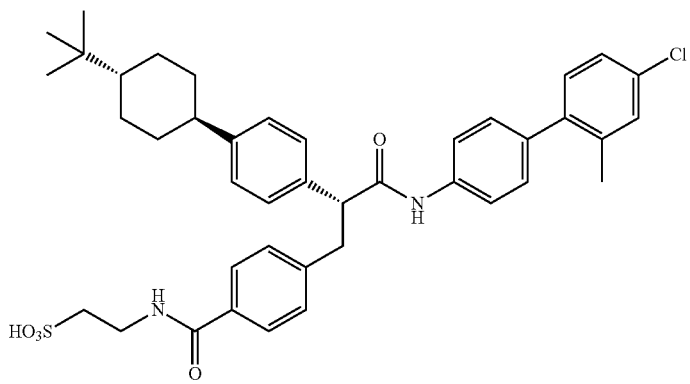 [SMILES: Cc1cc(Cl)ccc1-c1ccc(NC(=O)[C@H](Cc2ccc(C(=O)NCCS(=O)(=O)O)cc2)c2ccc([C@H]3CC[C@H](C(C)(C)C)CC3)cc2)cc1]

In certain embodiments, the compound of Formula I is selected from the group consisting of:

(R)-2-(4-(3-(4'-chloro-2'-methylbiphenyl-4-ylamino)-2-(4-((E)-3,3-dimethylbut-1-enyl)phenyl)-3 oxopropyl)benzamido)ethanesulfonic acid;

(R)-2-(4-(3-(4'-chloro-2'-methylbiphenyl-4-ylamino)-2-(3-(4,4-dimethylcyclohexyl)phenyl)-3-oxopropyl)benzamido)ethanesulfonic acid;

2-(4-((R)-2-(4-(cis-4-tert-butylcyclohexyl)phenyl)-3-(4'-chloro-2'-methylbiphenyl-4-ylamino)-3-oxopropyl)benzamido)ethanesulfonic acid;

2-(4((R)-2-(4-(trans-4-tert-butylcyclohexyl)phenyl)-3-(4'-chloro-2'-methylbiphenyl-4-ylamino)-3-oxopropyl)benzamido)ethanesulfonic acid;

2-(4((R)-2-(4-((R)-4-tert-butylcyclohex-1-enyl)phenyl)-3 (4'-chloro-2'-methylbiphenyl-4-ylamino)-3-oxopropyl) benzamido)ethanesulfonic acid;

2-(4-((R)-2-(4-((S)-4-tert-butylcyclohex-1-enyl)phenyl)-3-(4'-chloro-2'-methylbiphenyl-4-ylamino)-3-oxopropyl) benzamido)ethanesulfonic acid;

(R)-2-(4-(2-(4'-tert-butylbiphenyl-4-yl)-3-(4-(4,4-dimethyl-cyclohex-1-enyl)phenylamino)-3-oxopropyl)benzamido) ethanesulfonic acid;

(R)-2-(4-(3-(4'-chloro-2'-methylbiphenyl-4-ylamino)-2-(4-(4,4-dimethylcyclohex-1-enyl)phenyl)-3-oxopropyl)benzamido)ethanesulfonic acid;

2-(4((R)-3-(4-(benzo[d]oxazol-2-yl)phenylamino)-3-oxo-2-(4-((1S,4R)-1,7,7-trimethybicyclo[2.2.1]hept-2-en-2-yl) phenyl)propyl)benzamido)ethanesulfonic acid;

(R)-2-(4-(2-(4'-tert-butylbiphenyl-4-yl)-3-(4'-chloro-2'-methylbiphenyl-4-ylamino)-3-oxopropyl)benzamido)ethanesulfonic acid;

(R)-2-(4-(2-(4'-tert-butylbiphenyl-4-yl)-3-(4'-chloro-3'-methylbiphenyl-4-ylamino)-3-oxopropyl)benzamido)ethanesulfonic acid;

(R)-2-(4-(2-(4'-tert-butylbiphenyl-4-yl)-3-oxo-3-(2',4',6'-trimethylbiphenyl4-ylamino)propyl) benzamido)ethanesulfonic acid; and (R)-2-(4-(2-(4'-tert-butyl biphenyl yl)-3-(4-(4-methylbenzo [d]oxacol-2-yl)phenylamino)-3-oxopropyl)benzamido) ethanesulfonic acid.

In certain embodiments, the compound of Formula I is:

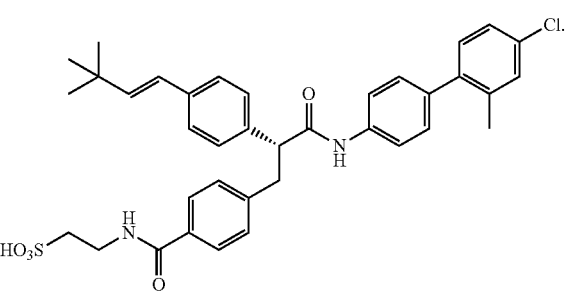 [SMILES: Cc1cc(Cl)ccc1-c1ccc(NC(=O)[C@H](Cc2ccc(C(=O)NCCS(=O)(=O)O)cc2)c2ccc(/C=C/C(C)(C)C)cc2)cc1]

In certain embodiments, the compound of Formula I is:

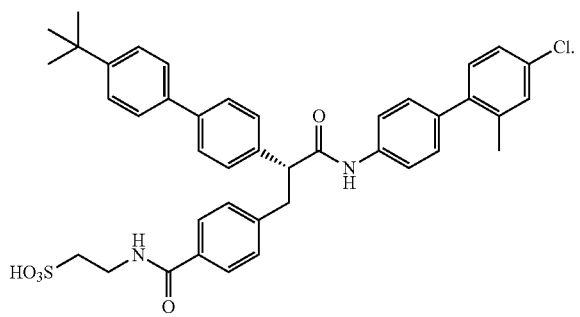 [SMILES: Cc1cc(Cl)ccc1-c1ccc(NC(=O)[C@H](Cc2ccc(C(=O)NCCS(=O)(=O)O)cc2)c2ccc(-c3ccc(C(C)(C)C)cc3)cc2)cc1]

In certain embodiments, the compound of Formula I is:

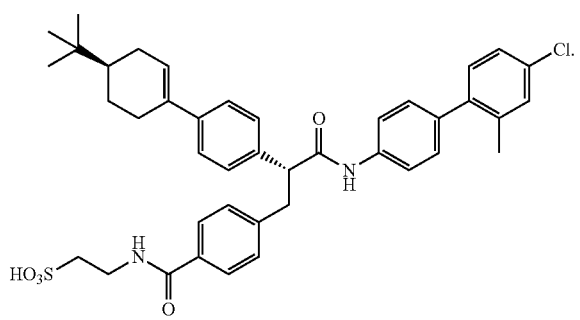 [SMILES: Cc1cc(Cl)ccc1-c1ccc(NC(=O)[C@H](Cc2ccc(C(=O)NCCS(=O)(=O)O)cc2)c2ccc(C3=CC[C@H](C(C)(C)C)CC3)cc2)cc1]

In certain embodiments, the compound of Formula I is:

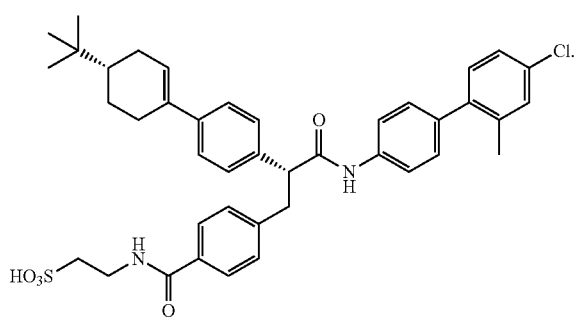 [SMILES: Cc1cc(Cl)ccc1-c1ccc(NC(=O)[C@H](Cc2ccc(C(=O)NCCS(=O)(=O)O)cc2)c2ccc(C3=CC[C@@H](C(C)(C)C)CC3)cc2)cc1]

In certain embodiments, the compound of Formula I is:

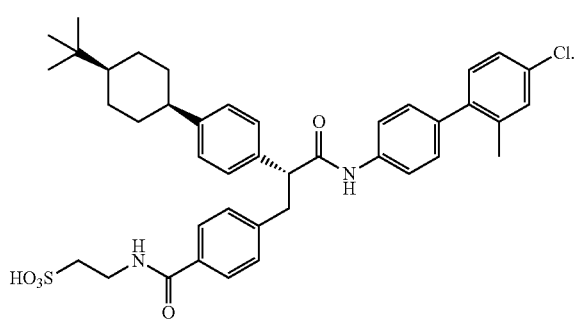 [SMILES: Cc1cc(Cl)ccc1-c1ccc(NC(=O)[C@H](Cc2ccc(C(=O)NCCS(=O)(=O)O)cc2)c2ccc([C@H]3CC[C@@H](C(C)(C)C)CC3)cc2)cc1]

In certain embodiments, the compound of Formula I is:

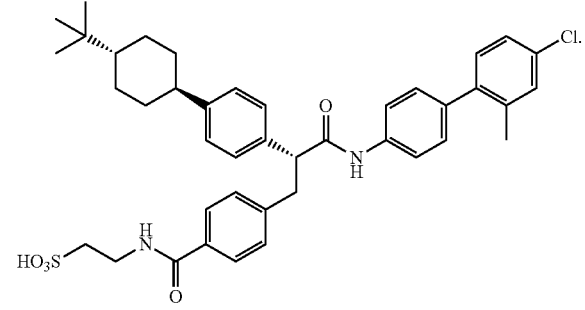 [SMILES: Cc1cc(Cl)ccc1-c1ccc(NC(=O)[C@H](Cc2ccc(C(=O)NCCS(=O)(=O)O)cc2)c2ccc([C@H]3CC[C@H](C(C)(C)C)CC3)cc2)cc1]

In certain embodiments, the compound of Formula I is (R)-2-(4-(3-(4'-chloro-2'-methylbiphenyl-4-ylamino)-2-(4 (E)-3,3-dimethylbut-1-enyl)phenyl)-3-oxopropyl)benzamido)ethanesulfonic acid.

In certain embodiments, the compound of Formula I is (R)-2-(4-(2-(4'-tert-butylbiphenyl-4-yl)-3-(4'-chloro-2'-methylbiphenyl-4-ylamino)-3-oxopropyl)benzamido)ethanesulfonic acid.

In certain embodiments, the compound of Formula I is 2-(4-((R)-2-(4-((R)-4-tert-butylcyclohex-1-enyl)phenyl)-3-(4'-chloro-2'-methylbiphenyl-4-ylamino)-3-oxopropyl)benzamido)ethanesulfonic acid.

In certain embodiments, the compound of Formula I is 2-(4-((R)-2-(4-((S)-4-tert-butylcyclodex-1-enyl)phenyl)-3-(4'-chloro-2'-methylbiphenyl-4-ylamino)-3-oxopropyl)benzamido)ethanesulfonic acid.

Another aspect provides for compounds of Formula II

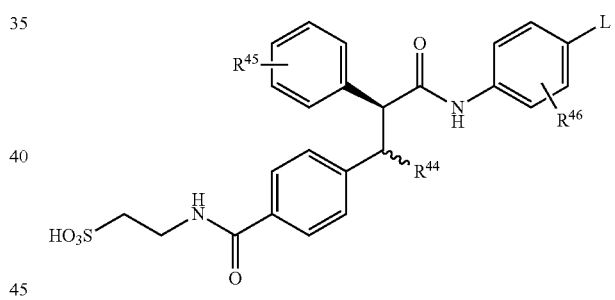

wherein:

$R^{44}$ is H, $CH_3$ or $CH_3CH_2$;

$R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or phenyl of which can be optionally substituted with one or more substituents;

L is phenyl, indenyl, benzoxazol-2-yl or 4,4-dimethylcyclohexenyl, any of which can be optionally substituted with one or more substituents; and $R^{46}$ represents one or more substituents selected from H, F, Cl, $CH_3$, $CF_3$, $OCF_3$ or CN.

In certain embodiments according to Formula II, the configuration of the aliphatic carbon which is alpha to the —C(O)NH— group is S.

In certain embodiments according to Formula II, L is substituted with one or more substituents independently selected from F, Cl, $CH_3$, $CF_3$, $OCF_3$ or CN.

In another embodiment, L is phenyl, benzoxazol-2-yl or 4,4-dimethylcyclohexenyl, optionally substituted with one or more substituents. In another embodiment, L is 4-chloro-2-methylphenyl, 4-methyl-2-benzoxazolyl, 2,4,6-trimethylphenyl, 2-benzoxazolyl, 4-chloro-3-methylphenyl or 4,4-dimethylcyclohexenyl.

In another embodiment, $R^{44}$ is H or $CH_3$. In another embodiment, $R^{44}$ is H.

In certain embodiments, $R^{45}$ is attached to the 3 (meta) or 4 (para) position. In another embodiment, $R^{45}$ is attached to the 4 (para) position.

In another embodiment, $R^{45}$ is alkenyl, $C_{3-6}$-cycloalkyl, $C_{4-8}$-cycloalkenyl, $C_{4-8}$-bicycloaklkenyl or phenyl, any of which can be optionally substituted with one or more substituents.

In certain embodiments according to Formula I, $R^{45}$ is optionally substituted and is selected from $(CH_3)_3CCH=CH-$, t-butyl-cycloalkyl-, dimethyl-cycloalkyl-, t-butyl-cycloalkenyl-, dimethyl-cycloalkenyl-, bicycloalkenyl or phenyl-.

In certain embodiments according to Formula I, $R^{45}$ is substituted with one or more substituents independently selected from $CH_3$ and $(CH_3)_3C-$.

In certain embodiments according to Formula I, $R^{45}$ is t-butylvinyl, cis-4-t-butylcyclohexyl, trans-4-t-butylcyclohexyl, 4,4-dimethylcyclohexyl, cyclohexenyl, (S)-4-t-butylcyclohexenyl, (R)-4-t-butylcyclohexenyl, 4,4-dimethylcyclohexenyl, 4,4-dipropylcyclohexanyl, 4,4-dimethylcyclohexadienyl, (1R,4S)-1,7,7-trimethylbicyclo[2.2.1]3-heptyl-2-ene, (1R,4R)-1,7,7-trimethylbicyclo[2.2.1]2-heptyl-2-ene, 2-methyl-4-chloro-phenyl, 2,4,6-trimethylphenyl or 4-t-butylphenyl.

In certain embodiments according to Formula I, $R^{45}$ is t-butylvinyl, cis-4-t-butylcyclohexyl, 4,4-dimethylcyclohexyl, (S)-4-t-butylcyclohexenyl, (R)-4-t-butylcyclohexenyl, 4,4-dimethylcyclohexenyl, (1R,4R)-1,7,7-trimethylbicyclo[2.2.1]2-heptyl-2-ene or 4-t-butylphenyl.

In another embodiment, $R^{46}$ is H or $CH_3$. In another embodiment, $R^{46}$ is H.

TABLE 2

Compounds of Formula II

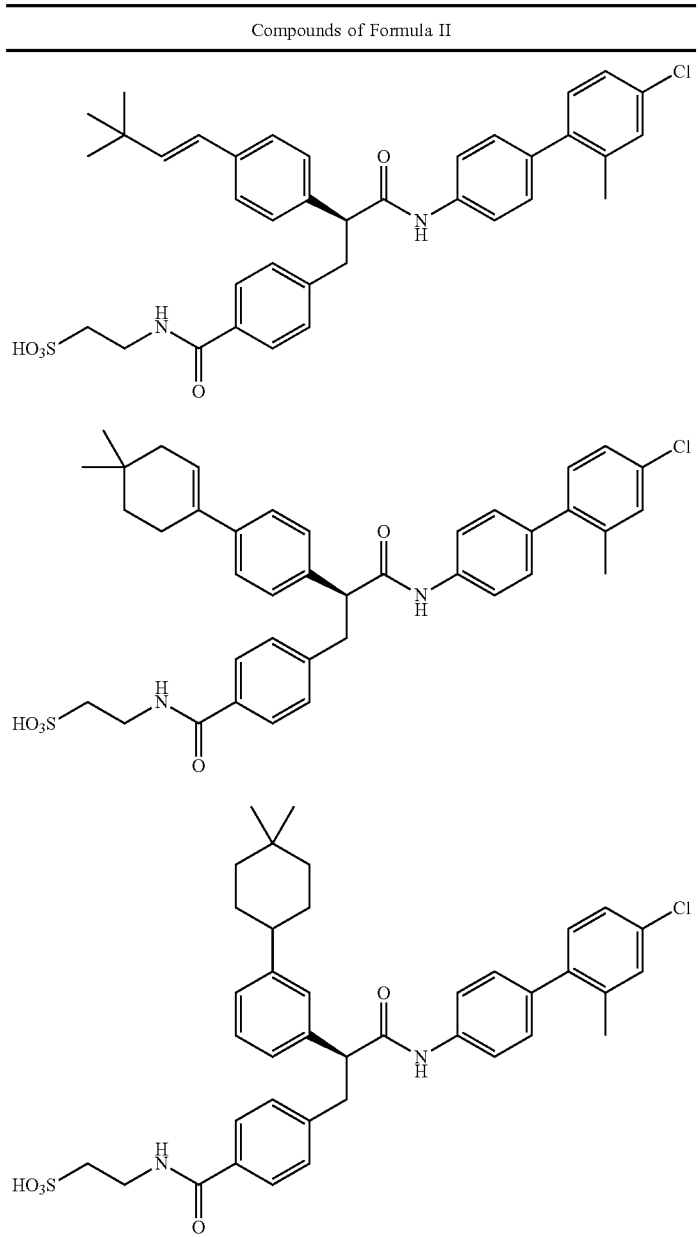

TABLE 2-continued
Compounds of Formula II
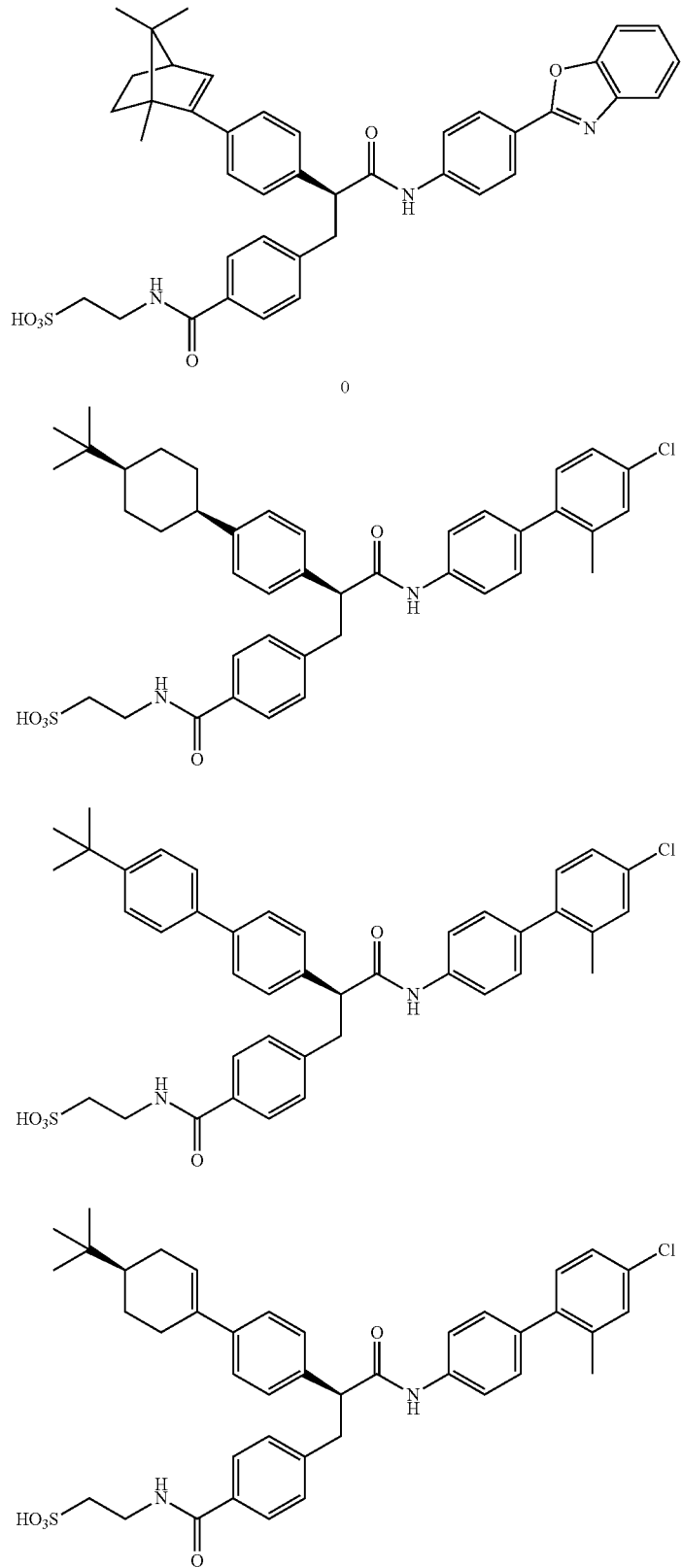

TABLE 2-continued
Compounds of Formula II
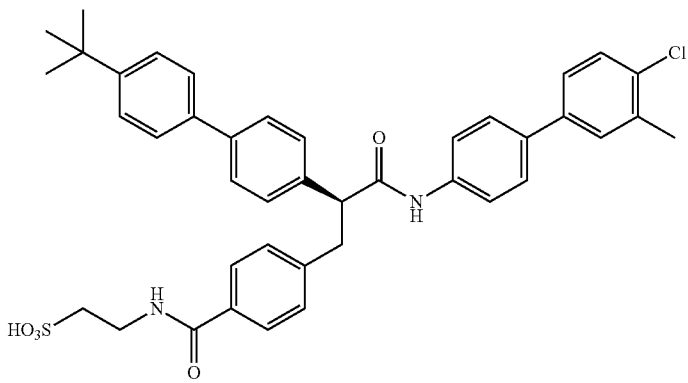 [SMILES: Cc1cc(-c2ccc(NC(=O)[C@@H](Cc3ccc(C(=O)NCCS(=O)(=O)O)cc3)c3ccc(-c4ccc(C(C)(C)C)cc4)cc3)cc2)ccc1Cl]
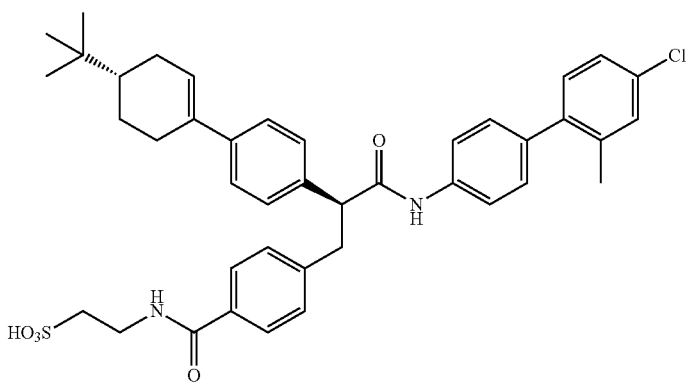 [SMILES: Cc1cc(Cl)ccc1-c1ccc(NC(=O)[C@@H](Cc2ccc(C(=O)NCCS(=O)(=O)O)cc2)c2ccc(C3=CC[C@@H](C(C)(C)C)CC3)cc2)cc1]
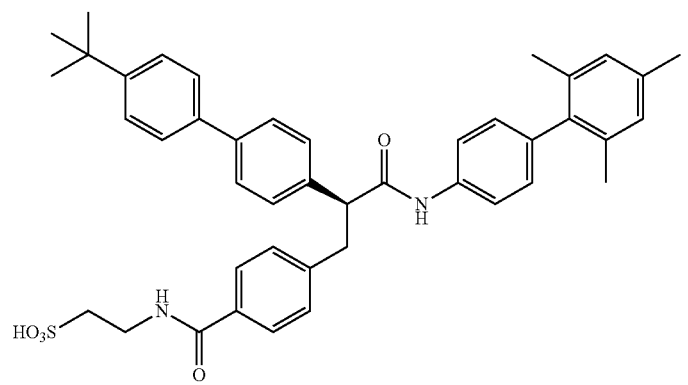 [SMILES: Cc1cc(C)c(-c2ccc(NC(=O)[C@@H](Cc3ccc(C(=O)NCCS(=O)(=O)O)cc3)c3ccc(-c4ccc(C(C)(C)C)cc4)cc3)cc2)c(C)c1]
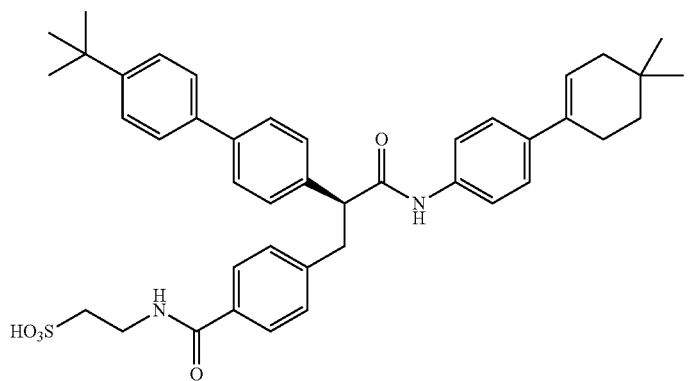 [SMILES: CC1(C)CC=C(c2ccc(NC(=O)[C@@H](Cc3ccc(C(=O)NCCS(=O)(=O)O)cc3)c3ccc(-c4ccc(C(C)(C)C)cc4)cc3)cc2)CC1]

TABLE 2-continued

Compounds of Formula II

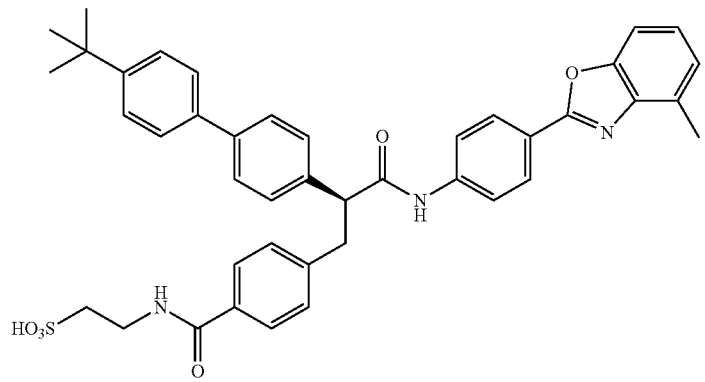 [SMILES: Cc1cccc2oc(-c3ccc(NC(=O)[C@@H](Cc4ccc(C(=O)NCCS(=O)(=O)O)cc4)c4ccc(-c5ccc(C(C)(C)C)cc5)cc4)cc3)nc12]

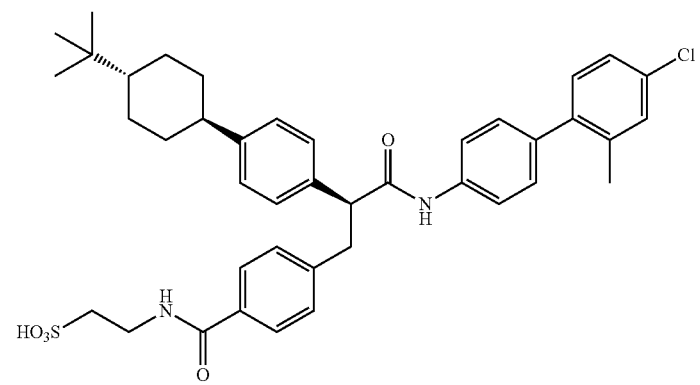 [SMILES: Cc1cc(Cl)ccc1-c1ccc(NC(=O)[C@@H](Cc2ccc(C(=O)NCCS(=O)(=O)O)cc2)c2ccc([C@H]3CC[C@H](C(C)(C)C)CC3)cc2)cc1]

In certain embodiments, the compound of Formula II is selected from the group consisting of:
- (S)-2-(4-(3-(4'-chloro-2'-methylbiphenyl-4-ylamino)-2-(4-((E)-3,3-dimethylbut-1-enyl)phenyl)-3-oxopropyl)benzamido)ethanesulfonic acid;
- (S)-2-(4-(3-(4'-chloro-2'-methylbiphenyl-4-ylamino)-2-(3-(4,4-dimethylcyclohexyl)phenyl)-3-oxopropyl)benzamido)ethanesulfonic acid;
- 2-(4-((S)-2-(4-(cis-4-tert-butylcyclohexyl)phenyl)-3-(4'-chloro-2'-methylbiphenyl-4-ylamino)-3-oxopropyl)benzamido)ethanesulfonic acid;
- 2-(4-((S)-2-(4-(trans-4-tert-butylcyclohexyl)phenyl)-3-(4'-chloro-2'-methylbiphenyl-4-ylamino)-3-oxopropyl)benzamido)ethanesulfonic acid;
- 2-(4-((S)-2-(4-((R)-4-tert-butylcyclohex-1-enyl)phenyl)-3-(4'-chloro-2'-methylbiphenyl-4-ylamino)-3-oxopropyl)benzamido)ethanesulfonic acid;
- 2-(4-((R)-2-(4-((S)-4-tert-butylcyclohex-1-enyl)phenyl)-3-(4'-chloro-2'-methylbiphenyl-4-ylamino)-3-oxopropyl)benzamido)ethanesulfonic acid;
- (S)-2-(4-(2-(4'-tert-butylbiphenyl-4-yl)-3-(4-(4,4-dimethylcyclohex-1-enyl)phenylamino)-3-oxopropyl)benzamido)ethanesulfonic acid;
- (S)-2-(4-(3-(4'-chloro-2'-methylbiphenyl-4-ylamino)-2-(4-(4,4-dimethylcyclohex-1-enyl)phenyl)-3-oxopropyl)benzamido)ethanesulfonic acid;
- 2-(4-((S)-3-(4-(benzo[d]oxazol-2-yl)phenylamino)-3-oxo-2-(4-((1S,4R)-1,7,7-trimethylbicyclo[2.2.1]hept-2-en-2-yl)phenyl)propyl)benzamido)ethanesulfonic acid;
- (S)-2-(4-(2-(4'-tert-butylbiphenyl-4-yl)-3-(4'-chloro-2'-methylbiphenyl-4-ylamino)-3-oxopropyl)benzamido)ethanesulfonic acid;
- (S)-2-(4-(2-(4'-tert-butylbiphenyl-4-yl)-3-(4'-chloro-3'-methylbiphenyl-4-ylamino)-3-oxopropyl)benzamido)ethanesulfonic acid;
- (S)-2-(4-(2-(4'-tert-butylbiphenyl-4-yl)-3-oxo-3-(2',4',6'-trimethylbiphenyl-4-ylamino)propyl)benzamido)ethanesulfonic acid; and
- (S)-2-(4-(2-(4'-tert-butylbiphenyl-4-yl)-3-(4-(4-methylbenzo[d]oxazol-2-yl)phenylamino)-3-oxopropyl)benzamido)ethanesulfonic acid.

In certain embodiments, the compound of Formula II is:

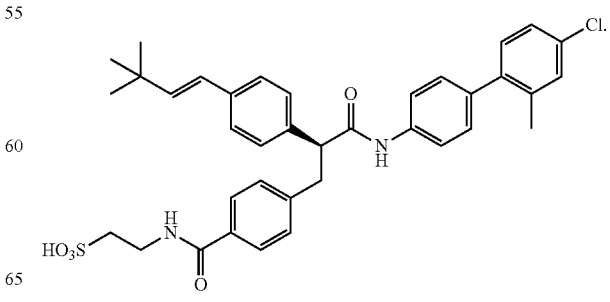

In certain embodiments, the compound of Formula II is:

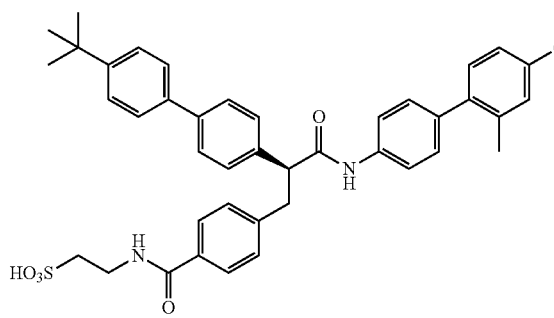

In certain embodiments, the compound of Formula II is:

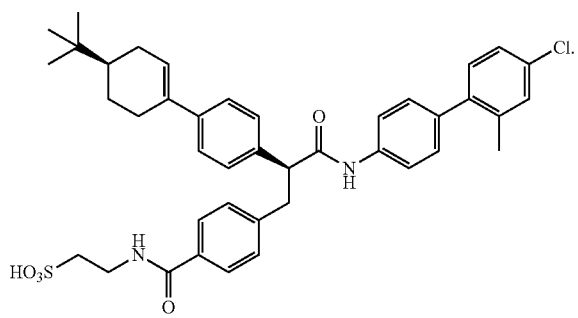 [SMILES: Cc1cc(Cl)ccc1-c1ccc(NC(=O)[C@@H](Cc2ccc(C(=O)NCCS(=O)(=O)O)cc2)c2ccc(C3=CC[C@H](C(C)(C)C)CC3)cc2)cc1]

In certain embodiments, the compound of Formula II is:

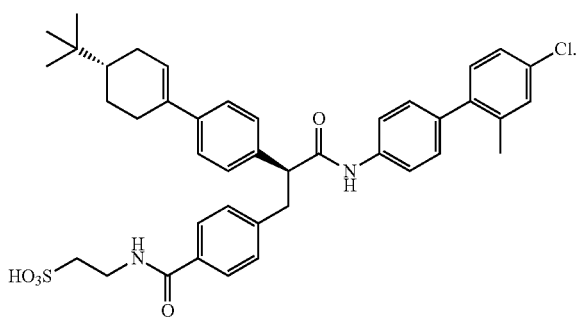 [SMILES: Cc1cc(Cl)ccc1-c1ccc(NC(=O)[C@@H](Cc2ccc(C(=O)NCCS(=O)(=O)O)cc2)c2ccc(C3=CC[C@@H](C(C)(C)C)CC3)cc2)cc1]

In certain embodiments, the compound of Formula II is:

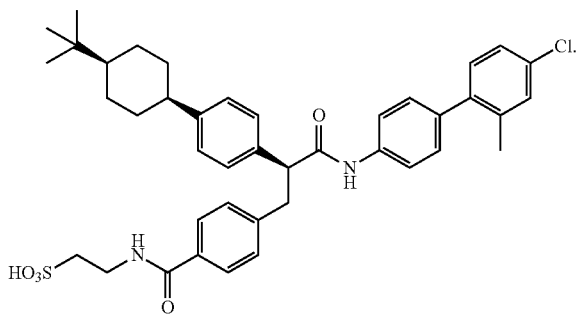 [SMILES: Cc1cc(Cl)ccc1-c1ccc(NC(=O)[C@@H](Cc2ccc(C(=O)NCCS(=O)(=O)O)cc2)c2ccc([C@H]3CC[C@@H](C(C)(C)C)CC3)cc2)cc1]

In certain embodiments, the compound of Formula II is:

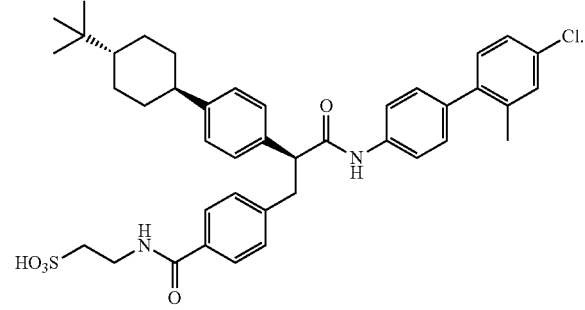 [SMILES: Cc1cc(Cl)ccc1-c1ccc(NC(=O)[C@@H](Cc2ccc(C(=O)NCCS(=O)(=O)O)cc2)c2ccc([C@H]3CC[C@H](C(C)(C)C)CC3)cc2)cc1]

In certain embodiments, the compound of Formula II is (S)-2-(4-(3-(4'-chloro-2'-methylbiphenyl-4-ylamino)-2-(4-((E)-3,3-dimethylbut-1-enyl)phenyl)-3-oxopropyl)benzamido)ethanesulfonic acid.

In certain embodiments, the compound of Formula II is (S)-2-(4-(2-(4'-tert-butylbiphenyl-4-yl)-3-(4'-chloro-2"-methylbiphenyl-4-ylamino)-3-oxopropyl)benzamido)ethanesulfonic acid.

In certain embodiments, the compound of Formula II is 2-(4-((S)-2-(4-((R)-4-tert-butylcyclohex-1-enyl)phenyl)-3-(4'-chloro-2'-methylbiphenyl-4-ylamino)-3-oxopropyl)benzamido)ethanesulfonic acid.

In certain embodiments, the compound of Formula II is 2-(4-((S)-2-(4-((S)-4-tert-butylcyclohex-1-enyl)phenyl)-3-(4'-chloro-2'-methylbiphenyl-4-ylamino)-3-oxopropyl)benzamido)ethanesulfonic acid.

Another aspect provides for compounds, prodrugs thereof, and compositions comprising the compounds or prodrugs thereof wherein the compound is:

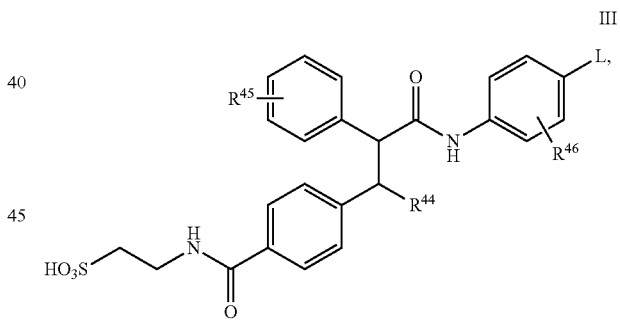

wherein:
$R^{44}$ is H;
$R^{45}$ is cis-4-t-butylcyclohexyl, trans-4-t-butylcyclohexyl, 4,4-dimethylcyclohexyl, 4,4-diethylcyclohexyl, 4,4-dipropylcyclohexyl, 4,4-diethylcyclohex-1-enyl, 4,4-dimethylcyclohex-1-enyl, (S)-4-t-butylcyclohexenyl, (R)-4-t-butylcyclohexenyl, 4,4-dipropylcyclohexanyl, (1R,4S)-1,7,7-trimethylbicyclo[2.2.1]-3-hept-2-enyl or (1R,4R)-1,7,7-trimethylbicyclo[2.2.1]-2-hept-2-enyl;
L is phenyl, benzoxazol-2-yl, 4-alkyl-cyclohex-1-enyl, 4,4-dialkylcyclohex-1-enyl, 4-alkyl-cyclohexyl, 4,4-dialkylcyclohexyl or 4,4-dimethylcyclohexenyl, any of which can be optionally substituted with one or more substituents; and
$R_{46}$ is H.

In certain embodiments according to Formula III, L is substituted with one or more substituents independently selected from Cl or $CH_3$. In another embodiment, L is phenyl, benzoxazol-2-yl or 4,4-dimethylcyclohexenyl, any of which can be optionally substituted with one or more substituents.

In certain embodiments according to Formula III, $R^{45}$ is attached to the 3 (meta) or 4 (para) position. In another embodiment, $R^{45}$ is attached to the 4 (para) position.

In another embodiment, $R^{45}$ is cis-4-t-butylcyclohexyl, trans-4-t-butylcyclohexyl, 4,4-dimethylcyclohexyl, (S)-4-t-butylcyclohexenyl, (R) 4-t-butylcyclohexenyl, 4,4-dipropylcyclohexenyl, (1R,4S)-1,7,7-trimethylbicyclo[2.2.1]-3-hept-2-enyl or (1R,4R)-1,7,7-trimethylbicyclo[2.2.1]-2-hept-2-enyl. In other embodiments, $R^{45}$ is cis-4-t-butylcyclohexyl, 4,4-dimethylcyclohexyl, (S)-4-t-butylcyclohexenyl, (R)-4-t-butylcyclohexenyl or (1R,4S)-1,7,7-trimethylbicyclo[2.2.1]-3-hept-2-enyl.

In certain embodiments according to Formula III, the compound has the Formula I.

In certain embodiments according to Formula III, the compound has the Formula II.

In certain embodiments according to Formula III, the configuration of the aliphatic carbon which is alpha to the —C(O)NH— group is R.

In certain embodiments according to Formula III, the configuration of the aliphatic carbon which is alpha to the —C(O)NH— group is S.

In certain embodiments, the compounds of Formula III are a racemic mixture.

Another aspect provides for enantiomerically pure compounds of Formula I, II or III. In certain embodiments, a single enantiomer is >60%, >70%, >80%, >85%, >90%, >91%, >92%, >93%, >94%, >95%, >96%, >97%, >98% or >99% as compared to the total percentage of all other enantiomers of the same compound present in the composition.

Another aspect provides enantiomerically pure compounds of Formula I, II or III. In certain embodiments, the compound comprises at least about 80% by weight of the designated enantiomer and at most about 20% by weight of the other enantiomer or other stereoisomer(s). In certain embodiments, the compound comprises at least about 90% by weight of the designated enantiomer and at most about 10% by weight of the other enantiomer or other stereoisomer(s). In certain embodiments, the compound comprises at least about 95% by weight of the designated enantiomer and at most about 5% by weight of the other enantiomer or other stereoisomer(s). In certain embodiments, the compound comprises at least about 96.6% by weight of the designated enantiomer and at most about 3.4% by weight of the other enantiomer or other stereoisomer(s). In certain embodiments, the compound comprises at least about 97% by weight of the designated enantiomer and at most about 3% by weight of the other enantiomer or other stereoisomer(s). In certain embodiments, the compound comprises at least about 99% by weight of the designated enantiomer and at most about 1% by weight of the other enantiomer or other stereoisomer(s). In certain embodiments, the compound comprises at least about 99.9% by weight of the designated enantiomer and at most about 0.1% by weight of the other enantiomer or other stereoisomer(s). In certain embodiments, the weights are based upon total weight of the compound.

Another aspect provides for salts, including pharmaceutically acceptable salts, of compounds of Formula I, II or III and pharmaceutical compositions comprising a pharmaceutically acceptable salt of compounds of Formula I, II or III. Salts of compounds of Formula I, II or III include an inorganic base addition salt such as sodium, potassium, lithium, calcium, magnesium, ammonium, aluminum salts or organic base addition salts, or an inorganic acid addition salt such as HBr, HCl, sulfuric, nitric, or phosphoric acid addition salts or an organic acid addition salt such as acetic, propionic, pyruvic, malanic, succinic, malic, maleic, fumaric, tartaric, citric, benzoic, methanesulfonic, ethanesulforic, stearic or lactic acid addition salt.

Another aspect provides for anhydrates, hydrates and solvates of compounds of Formula I, II or III and pharmaceutical compositions comprising a pharmaceutically acceptable anhydrates, hydrates and solvates of compounds of Formula I, II or III. Included are an anhydrate, hydrate or solvate of a free form or salt of a compound of Formula I, II or III. Hydrates include, for example, a hemihydrate, monohydrate, dihydrate, trihydrate, quadrahydrate, pentahydrate, sesquihydrate.

In certain embodiments, the compounds of Formula I, II or III are able to displace radiolabeled glucagon from the human glucagon receptor by at least 15% at 1000 nM. In one embodiment, the compounds of Formula I, II or III are able to displace at least 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of radiolabeled glucagon from the human glucagon receptor as described in Example A.

Alternatively, the activities of the compounds of Formula I, II or III can be described in terms of the concentrations of compounds required for displacement of 50% of the radiolabeled glucagon from the human glucagon receptor (the $IC_{50}$ values) according to the methods of Example A. In one embodiment, the $IC_{50}$ values for the compounds of Formula I are less than <10,000 nM, 9,000 nM, 8,000 nM, 7,000 nM, 6,000 nM, 5,000 nM, 4,000 nM, 3,000 nM, 2,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM or 5 nM.

In another alternative, the activities of the compounds of Formula I, II or III can be described in terms of the concentrations of compounds required for functional antagonism of glucagon in hepatocytes from various species. The $EC_{50}$ is determined using the method of Example B. In one embodiment, the $EC_{50}$ values for the compounds of Formula I, II or III are less than <10,000 nM, 9,000 nM, 8,000 nM, 7,000 nM, 6,000 nM, 5,000 nM, 4,000 nM, 3,000 nM, 2,000 nM. 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM or 5 nM.

The compounds of Formula I, II or III disclosed herein also exhibit the ability to reduce blood glucose in an animal. In certain aspects, circulating blood glucose in fasting or non-fasting (freely-feeding) animals can be reduced between 10% and 100%. A reduction of 100% refers to complete normalization of blood glucose levels, not 0% blood glucose levels. Normal blood glucose in rats, for example, is approximately 80 mg/dl (fasted) and approximately 120 mg/dl (fed). Thus, contemplates herein is a method for reducing excessive circulating blood glucose levels in fasting or freely fed animals (e.g. rat), by administered 10 mg/kg of a compound of Formula I, by at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% c. Formulations

Provided herein are pharmaceutical compositions including a compound provided herein as an active ingredient, e.g., a compound of Formula I, II or III, or a pharmaceutically acceptable salt, solvate, or prodrug thereof; in combination with a pharmaceutically acceptable vehicle, carrier, diluent, excipient, or a mixture thereof.

The pharmaceutical compositions may be formulated in various dosage forms, including, but limited to, the dosage forms for oral, parenteral, or topical administration. The pharmaceutical compositions may also be formulated as modified release dosage forms, including, but not limited to, delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2003 Vol. 126).

In one embodiment, the pharmaceutical compositions are provided in a dosage form for oral administration, which comprise a compound provided herein, e.g., a compound of Formula I, II or III, or a pharmaceutically acceptable salt, solvate, or prodrug thereof; and a pharmaceutically acceptable vehicle, carrier, diluent, excipient, or a mixture thereof.

In another embodiment, the pharmaceutical compositions are provided in a dosage form for parenteral administration, which comprise a compound provided herein, e.g., a compound of Formula I, II or III, or a pharmaceutically acceptable salt, solvate, or prodrug thereof; and a pharmaceutically acceptable vehicle, carrier, diluent, excipient, or a mixture thereof.

In yet another embodiment, the pharmaceutical compositions are provided in a dosage form for topical administration, which comprise a compound provided herein, e.g., a compound of Formula I, II or III, or a pharmaceutically acceptable salt, solvate, or prodrug thereof; and a pharmaceutically acceptable vehicle, carrier, diluent, excipient, or a mixture thereof.

The pharmaceutical compositions provided herein may be provided in a unit- or multiple-dosage form. A unit-dosage form, as used herein, refers to a physically discrete unit suitable for administration to a subject, and packaged individually as is known in the art. Each unit-dose contains a predetermined quantity of the active ingredient(s) sufficient to produce the desired therapeutic effect, in association with the required pharmaceutically acceptable vehicle, carrier, diluent, excipient, or a mixture thereof. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include a vial, bottle of tablets or capsules, or bottle of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the pharmaceutical compositions provided herein.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions (e.g., aqueous or oil suspensions), wafers, sprinkles, elixirs, syrups, bolus, electuaries, or pastes. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, preserving agents, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof, In certain embodiments, the binder or filler is present from about 50 to about 99% by weight in the pharmaceutical compositions provided herein.

Suitable diluents include, but are not limited to, dicalcium phosphate, calcium sulfate, calcium carbonate, sodium carbonate, sodium phosphate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, maize starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. In certain embodiments, the pharmaceutical compositions provided herein contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, Md.) and CAB-O-SIL® (Cabot Co. of Boston, Mass.); and mixtures thereof. In certain embodiments, the pharmaceutical compositions provided herein contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Coloring agents include, but are not limited to, any of the approved, certified, water soluble FD&C dyes, water insoluble FD&C dyes suspended on alumina hydrate, and color lakes, and mixtures thereof. A color lake is the combination by adsorption of a water-soluble dye to a hydrous oxide of a heavy metal, resulting in an insoluble form of the dye. Flavoring agents include, but are not limited to, natural flavors extracted from plants, such as fruits, and synthetic blends of compounds which produce a pleasant taste sensation, such as peppermint and methyl salicylate. Sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Preservatives include, but are not limited to, glycerin, methyl and propylparaben, benzoic add, sodium benzoate and alcohol. Wetting agents include, but are not limited to, propylene glycol monostearate, sorbitan monooleate, diethylene glycol monolaurate, and polyoxyethylene lauryl ether. Solvents include, but are not limited to, glycerin, sorbitol, ethyl alcohol, and syrup. Examples of non-aqueous liquids utilized in emulsions include mineral oil and cottonseed oil. Organic acids include, but are not limited to, citric and tartaric acid. Sources of carbon dioxide include, but are not limited to, sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, uncoated tablets, enteric coated tablets, sugar-coated tablets, or film-coated tablets, Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered, press-coated, and dry-coated tablets. Tablets may also be coated using microencapsulation to delay disintegration and absorption in the gastrointestinal tract and thereby provide a sustained action over a longer period.

The tablet dosage forms may be prepared from the active ingredient in powdered, crystalline, or granular forms, alone or in combination with a pharmaceutically acceptable vehicle, carrier, diluent, or excipient, or a mixture thereof; including a binder, disintegrant. controlled-release polymer, lubricant, diluent, and/or colorant. Flavoring and sweetening agents are especially useful in the formation of chewable tablets and lozenges. Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

A tablet may be made by compression or molding, optionally with one or more accessory ingredients. Compressed tablets may be prepared by compressing in a suitable machine a compound provided herein in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross linked povidone, cross linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This can be useful in embodiments where the compounds provided herein are susceptible to acid hydrolysis.

The pharmaceutical compositions provided herein may be provided as soft or hard capsules, which can be made from gelatin, methylcellulose, starch, or calcium alginate. The hard gelatin capsule, also known as a dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including, but not limited to, methyl- and propyl-parabens, and sorbic acid. The liquid, semisolid, and solid dosage forms provided herein may be encapsulated in a capsule. Suitable liquid and semisolid dosage forms include, but are not limited to, solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient. In other embodiments, a hard gelatin capsule contains a mixture of a compound provided herein and an inert solid diluent, e.g., calcium phosphate or kaolin. In other embodiments, a soft gelatin capsule contains a mixture of a compound provided herein and an inert fluidic diluent, e.g., water or an oil medium such as peanut oil, liquid paraffin, or olive oil.

The pharmaceutical compositions provided herein may be provided in liquid and semisolid dosage forms, including, but not limited to, emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative.

Suspensions may include a pharmaceutically acceptable suspending agent and preservative. In some embodiments, aqueous suspensions contain an admixture of a compound provided herein and an excipient suitable for the manufacture of aqueous suspensions. Examples of suitable excipients a suspending agent, such as sodium carboxymethylcellulose, methylcellulose, ethylcellulose, hydroxypropylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n propyl p hydroxy benzoate, one or more coloring agents, one or more flavoring agents and one or more sweetening agents, such as sucrose or saccharin.

Oil suspensions may be formulated by suspending a compound provided herein in a vegetable oil, such as arachid oil, olive oil, sesame oil or coconut oil, or in a mineral oil such as liquid paraffin. Suspensions for oral administration may contain a thickening agent, such as beeswax, hard paraffin or cetyl alcohol, sweetening agent, and/or a flavoring agent. Such compositions may be preserved by the addition of an antioxidant such as ascorbic acid.

Dispersible powders and granules of compounds provided herein are suitable for preparation of an aqueous suspension by the addition of water provide an admixture of a compound provided herein and a dispersing or wetting agent, a suspending agent, and one or more preservatives. Additional excipients, for example sweetening, flavoring and coloring agents, may also be present.

Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol.

Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration. Syrups and elixirs may be formulated with sweetening agents, such as glycerol, sorbitol or sucrose. Such formulations may also contain a demulcent, a preservative, a flavoring or a coloring agent.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates, The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the dosage forms described herein.

As described in greater detail below, the pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable outliers and excipients, including, but not limited to, aqueous vehicles, water-miscible vehicles, non-aqueous vehicles, bacteriostats, solutes which render the formulation isotonic with the blood of the intended recipient, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringer's injection, isotonic dextrose injection, sterile water injection, and dextrose and lactated Ringer's injection. Non-aqueous vehicles include, but are not limited to, oils including synthetic mono- or diglycerides, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, medium-chain triglycerides of coconut oil, oleic acid, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including a-cyclodextrin, b-cyclodextrin, hydroxypropyl-b-cyclodextrin, sulfobutylether-b-cyclodextrin, and sulfobutylether 7-b-cyclodextrin (CAPTISOL®, CyDex, Lenexa, Kans.).

The pharmaceutical compositions provided herein may be formulated for single or multiple dosage administration, The single dosage formulations are packaged in an ampoule, a vial, or a syringe. In certain embodiments, the multiple dosage parenteral formulations contain an antimicrobial agent at bacteriostatic or fungistatic concentrations. In certain embodiments, the parenteral formulations provided herein are sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders, hypodermic tablets, or granules, to be reconstituted with a vehicle (such as sterile water for injections) prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

Formulations suitable for parenteral administration may be administered in a continuous infusion manner, e.g., via an indwelling or external pump or via a hospital bag. The invusions may be done through a Hickman or PICC or any other suitable means of administering a formulation parentally.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semisolid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, bolus, electuaries, pastes, and dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including lard, benzoinated lard, olive oil, cottonseed oil, and other oils; white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; and emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream bases can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout a liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; a salicylate, and glycerinated gelatin. Combinations of the various vehicles may be used. Rectal and vaginal suppositories may further comprise antioxidants as described herein, including bisulfite and sodium metabisulfite. Rectal and vaginal suppositories may be prepared by the compressed method or molding. The typical weight of a rectal and vaginal suppository is about 2 to about 3 g.

Formulations suitable for vaginal administration may be presented as pessaries, tampons, creams, gels, pastes, foams or spray formulations containing in addition to the active ingredient such carriers as are known in the art to be appropriate.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; or nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator may be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of monohydrates. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

In some embodiments, a "pill and patch" strategy may be taken, in which a fraction of the daily dose is provided topically (e.g., transdermally) to generate basal systemic levels, and an oral therapy further provided.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microparticles, microspheres, liposomes, and combinations thereof. The release rate of the active ingredient(s) can also be modified by varying the particle sizes and polymorphism of the active ingredient(s).

Additionally, ion exchange materials can be used to prepare immobilized, adsorbed co-crystals and thus effect controlled delivery of the drug. Examples of specific anion exchanges include, but are not limited to, Duolite A568 and Duolite AP143 (Rohm & Haas, Spring House Pa., USA).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,365,185; 6,376,461; 6,419,961; 6,589,548; 6,613,358; and 6,699,500, 1. Matrix Controlled Release Devices The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein is formulated in a modified release dosage form using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In certain embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, or melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents includes osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters, poly-(methacrylic) acids and esters, and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings as described in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In certain embodiments, the pharmaceutical compositions provided herein are formulated as an AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, or dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

One example of a suitable osmotic drug delivery system is referred to as OROS (Alza Corporation, Mountain View, Calif. USA). Various aspects of the technology are disclosed in U.S. Pat. Nos. 6,375,978; 6,368,626; 6,342,249; 6,333,050; 6,287,295; 6,283,953; 6,270,787; 6,245,357; and 6,132,420; each of which is incorporated herein by reference in its entirety. Specific adaptations of OROS that can be used to administer compounds and compositions provided herein include, but are not limited to, the OROS, Push-Pull, Delayed Push-Pull, Multi-Layer Push-Pull, and Push-Stick Systems available from Alza Corporation. Additional OROS systems that can be used for the controlled oral delivery of compounds and compositions provided herein include OROS-CT and L-OROS, also available from Alza Corporation.

OROS oral dosage forms may be made by compressing a drug powder into a hard tablet, coating the tablet with cellulose derivatives to form a semi-permeable membrane, and then drilling an orifice in the coating (e.g., with a laser). For further details, see Kim, Cherug-ju, Controlled Release Dosage Form Design, 231-238 (Technomic Publishing, Lancaster, Pa.: 2000). One feature of such dosage forms is that the delivery rate of the drug is not influenced by physiological or experimental conditions. Even a drug with a pH-dependent solubility can be delivered at a constant rate regardless of the pH of the delivery medium.

In one embodiment, a dosage form is provided in which a wall is formed defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer includes a crystalline form of a compound provided herein, For further details, see U.S. Pat. No. 6,368,626, the entirety of which is incorporated herein by reference.

In another embodiment, a dosage is provided in which a wall is formed defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer, the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent includes a crystalline form of a compound provided herein. For further details, see U.S. Pat. No. 6,342,249, the entirety of which is incorporated herein by reference, 3. Multiparticulate Controlled Release Devices The pharmaceutical compositions provided herein in a modified release dosage form may be fabricated a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, Multiparticulate Oral Drug Delivery; Marcel Dekker: 1994; and Pharmaceutical Pelletization Technology; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, those described in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, preventing, or ameliorating one or more symptoms of a condition, disorder, or disease associated with a glucagon receptor, comprising administering to a subject having or being suspected to have such a condition, disorder, or disease, a therapeutically effective amount of a compound provided herein, e.g., a compound of Formula I, II or III, or a pharmaceutically acceptable salt, solvate, or prodrug thereof; or a pharmaceutical composition thereof. In one embodiment, the subject is a mammal. In another embodiment, the subject is a human.

In another embodiments, provided herein is a method of treating, preventing, or ameliorating one or more symptoms of a condition, disorder, or disease responsive to the modulation of a glucagon receptor, comprising administering to a subject having or being suspected to have such a condition, disorder, or disease, a therapeutically effective amount of a compound provided herein, e.g., a compound of Formula I, II or III, or a pharmaceutically acceptable salt, solvate, or prodrug thereof; or a pharmaceutical composition thereof. In one embodiment, the subject is a mammal. In another embodiment, the subject is a human.

In yet another embodiment, provided herein is a method of treating, preventing, or ameliorating one or more symptoms of a glucagon-mediated condition, disorder, or disease, comprising administering to a subject having or being suspected to have such a condition, disorder, or disease, a therapeutically effective amount of a compound provided herein, e.g., a compound of Formula I, II or III, or a pharmaceutically acceptable salt, solvate, or prodrug thereof; or a pharmaceutical composition thereof. In one embodiment, the subject is a mammal. In another embodiment, the subject is a human.

In yet another embodiments, provided herein is a method of treating, preventing, or ameliorating one or more symptoms of a condition, disorder, or disease responsive to a decrease in the hepatic glucose production or in the blood glucose level of a subject, comprising administering to the subject having or being suspected to have such a condition, disorder, or disease, a therapeutically effective amount of a compound provided herein, e.g., a compound of Formula I, II or III, or a pharmaceutically acceptable salt, solvate, or prodrug thereof; or a pharmaceutical composition thereof. In one embodiment, the subject is a mammal. In another embodiment, the subject is a human.

The conditions and diseases treatable with the methods provided herein include, but are not limited to, type 1 diabetes, type 2 diabetes, gestational diabetes, ketoacidosis, nonketotic hyperosmolar coma (nonketotic hyperglycaemia), impaired glucose tolerance (IGT), insulin resistance syndromes, syndrome X, low HDL levels, high LDL levels, hyperglycemia, hyperinsulinemia, hyperlipidemia, hypertriglyceridemia, hyperlipoproteinemia, hypercholesterolemia, dyslipidemia, arteriosclerosis, atherosclerosis, glucagonomas, acute pancreatitis, cardiovascular diseases, hypertension, cardiac hypertrophy, gastrointestinal disorders, obesity, vascular resenosis, pancreatitis, neurodegenerative disease, retinopathy, nephropathy, neuropathy, accelerated gluconeogenesis, excessive (greater than normal levels) hepatic glucose output, and lipid disorders.

In one embodiment, the condition or disease treatable with the methods provided herein is diabetes mellitus, including type 1, type 2, and gestational diabetes. In one embodiment, the diabetes is type 1. In another embodiment, the diabetes is type 2. In yet another embodiment, the diabetes is gestational diabetes.

Provided herein are also methods of delaying the time to onset or reducing the risk of the development or progression of a disease or condition responsive to decreased hepatic glucose production or responsive to lowered blood glucose levels.

Depending on the condition, disorder, or disease to be treated and the subject's condition, a compound provided herein may be administered by oral, parenteral (e.g., intramuscular, intraperitoneal, intravenous or intraarterial (e.g., via catheter), ICV, intracistemal injection or infusion, subcutaneous injection, or implant), inhalation, nasal, vaginal, rectal, sublingual, and/or topical (e.g., transdermal or local) routes of administration, and may be formulated alone or together in suitable dosage unit with a pharmaceutically acceptable vehicle, carrier, diluent, excipient, or a mixture thereof, appropriate for each route of administration.

The dose may be in the form of one, two, three, four, five, six, or more sub-doses that are administered at appropriate intervals per day. The dose or sub-doses can be administered in the form of dosage units containing from about from about 0.01 to 2500 mg, from 0.1 mg to about 1,000 mg, from about 1 mg to about 1000 mg, from about 1 mg to about 500 mg, from about 0.1 mg to about 500 mg, from about 0.1 mg to about 100 mg, from about 0.5 mg about to about 100 mg, from about 1 mg to about 100 mg, from about 10 mg to about 1000 mg, from about 10 mg to about 500 mg, or from about 10 mg to about 100 mg of active ingredient(s) per dosage unit. For example, the dose or subdoses can be administered in the form of dosage units containing about 10 mg, about 25 mg, about 50 mg, about 75 mg, about 100 mg, about 250 mg, about 300 mg, about 400 mg, about 500 mg, about 600 mg, about 700 mg, about 800 mg, about 900 mg, or about 1000 mg. If the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range, the dosage may be about 0.01 to about 0.1, about 0.1 to about 1.0, about 1.0 to about 10, or about 10 to about 50 mg/kg per day.

For oral administration, the pharmaceutical compositions can be provided in the form of tablets containing 1.0 to 1,000 mg of the active ingredient, particularly about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated, The compositions may be administered on a regimen of 1 to 4 times per day, including once, twice, three times, and four times per day. In various embodiments, the compositions may be administered before a meal, after a meal, in the morning hours, after awakening, in the evening hours, and/or at bedtime.

It will be understood, however, that the specific dose level, frequency, and timing of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In still another embodiment, provided herein is a method of modulating the biological activity of a glucagon receptor, comprising contacting the receptor with one or more of the compounds provided herein, e.g., a compound of Formula I, including a single enantiomer, a mixture of enantiomers, or a mixture of diastereomers thereof, or a pharmaceutically acceptable salt, solvate, or prodrug thereof; or a pharmaceutical composition thereof. In one embodiment, the glucagon receptor is expressed by a cell.

The compounds provided herein may also be combined or used in combination with other therapeutic agents useful in the treatment, prevention, or amelioration of one or more symptoms of the conditions, disorders, or diseases for which the compounds provided herein are useful. As used herein, the term "in combination" includes the use of more than one therapeutic agents. However, the use of the term "in combination" does not restrict the order in which therapeutic agents are administered to a subject with a condition, disorder, or disorder. A first therapeutic agent (e.g., a therapeutic agent such as a compound provided herein) can be administered prior to (e.g., 5 min, 15 min, 30 min, 45 min, 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 12 wks before), concomitantly with, or subsequent to (e.g., 5 min, 15 min, 30 min, 45 min, 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 1:2 wks after) the administration of a second therapeutic agent to a subject to be treated.

When a compound provided herein is used contemporaneously with one or more therapeutic agents, a pharmaceutical composition containing such other agents in addition to the compound provided herein may be utilized, but is not required. Accordingly, the pharmaceutical compositions provided herein include those that also contain one or more other therapeutic agents, in addition to a compound provided herein.

In one embodiment, the other therapeutic agent is an antidiabetic agent. Suitable antidiabetic agents include, but are not limited to, insulin sensitizers, biguanides (e.g., buformin, metformin, and phenformin), PPAR agonists (e.g., troglitazone, pioglitazone, and rosiglitazone), insulin and insulin mimetics, somatostatin, a-glucosidase inhibitors (e.g., voglibose, miglitol, and acarbose), dipeptidyl peptidase-4 inhibitors, liver X receptor modulators, insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, sulfonylureas, tolazamide, tolbutamide, tolcyclamide, nateglinide, and repaglinide), other glucagon receptor antagonists, GLP-1, GLP-1 mimetics, GLP-1 receptor agonists, GIP, GIP mimetics, GIP receptor agonists, PACAP, PACAP mimetics, PACAP receptor 3 agonists, cholesterol lowering agents, HMG-CoA reductase inhibitors (e.g., statins, such as lovastatin, simvastatin, pravastatin, fluvastatin, atorvastatin, itavastatin, rivastatin, NK-104 (a.k.a. itavastatin, nisvastatin, and nisbastatin), and ZD-4522 (also known rosuvastatin, atavastatin, and visastatin)), a cholesterol absorption inhibitor (e.g., ezetimibe), sequestrants, nicotinyl alcohol, nicotinic acid and salts thereof, PPAR α agonists, PPAR α/γ dual agonists, inhibitors of cholesterol absorption, acyl CoA:cholesterol acyltransferase inhibitors, anti-oxidants, PPAR δ agonists, anti-obesity compounds, ileal bile acid transporter inhibitors, anti-inflammatory agents, and protein tyrosine phosphatase-1B (PTP-1B) inhibitors.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIIb/IIIa blockers (e.g., eptifibatide, abciximab, cilostazol, clopidogrel, dipyridamole, ticlopidine, and tirofibin), P2Y(AC) antagonists (e.g., clopidogrel, ticlopidine and CS-747), and aspirin; anticoagulants, such as acenocoumarol, argatroban, bivalirudin, lepirudin, fondaparinux, heparin, phenindione, warfarin, and ximelagatran; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as anistreplase, reteplase, tissue plasminogen activator (tPA), recombinant tPA, streptokinase, tenecteplase, urokinase, prourokinase, and anisoylated plasminogen streptokinase activator complex (APSAC); antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as *vinca* alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

The dosages given will depend on absorption, inactivation and excretion rates of the drug as well as other factors known to those of skill in the art. It is to be noted that dosage values will also vary with the severity of the condition to be alleviated, It is to be further understood that for any particular subject, specific dosage regimens and schedules should be adjusted over time according to the individual need and the professional judgment of the person administering or supervising the administration of the compositions.

The weight ratio of a compound provided herein to the second active ingredient depends upon the effective dose of each ingredient. Generally, an effective dose of each will be used. Thus, for example, when a compound provided herein is combined with a PPAR agonist the weight ratio of the compound provided herein to the PPAR agonist will generally range from about 1000:1 to about 1:1000 or about 2001 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a mixture of an enantiomeric pair, an individual diastereomer, or a mixture of diastereomers thereof; or a pharmaceutically acceptable salt, solvate, or prodrug thereof.

In certain embodiments, the kit includes a container comprising a dosage form of the compound provided herein, including a single enantiomer, a mixture of an enantiomeric pair, an individual diastereomer, or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

5. Synthesis of Compounds

Compounds of Formula I, II and III can be prepared according to the methodology outlined in the following general synthetic schemes or with modifications of these schemes that will be evident to persons skilled in the art, or by other methods readily known to those of skill in the art.

In the following sections, the following abbreviations have the following meanings:

THF: Tetrahydrofuran

DME: 1,2-Dimethoxyethane

DMF: N,N-Dimethylformamide

DCC: N,N'-Dicyclohexycarbodiimide

EDCI or EDC: 1-(3-Dimethylaminopropyl)-3-ethyl carbodiimide hydrochloride

LiHMDS: Lithium hexamethyldisilyl azide

HOBt: 1-Hydroxybenzotriazole

EtOAc: Ethyl acetate

EtOH: Ethanol

IPA: iso-Propanol

ACN: Acetonitrile

DIPEA: N,N-Diisopropy-ethyl amine

MTBE: Methyl-tert-butyl ether

Synthesis of Various Building Blocks:

The carboxylic acids 3 can be generated using standard methods. As shown in Scheme 1, a carboxylic ester or acid 1 can be alkylated by reaction with a base (such as lithium diisopropylamide or lithium hexamethyldisilylamide) in a suitable solvent (such as THF or DME) followed by reaction with an aralkyl halide to generate intermediates 2. In one embodiment, when Ra is not hydrogen, then the Ra and Rb groups are adequately chosen so that liberation of the carboxylic acid to generate 3 can take place selectively (obviously, when Ra is H, 2 and 3 represent the same intermediate). For example, if Ra is a methyl or ethyl group, an Rb group can be a benzyl, t-butyl, 2-trimethylsilylethyl group or other groups that can be selectively removed under conditions where the ester group Ra would remain intact.

Scheme 1

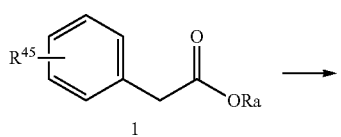

-continued

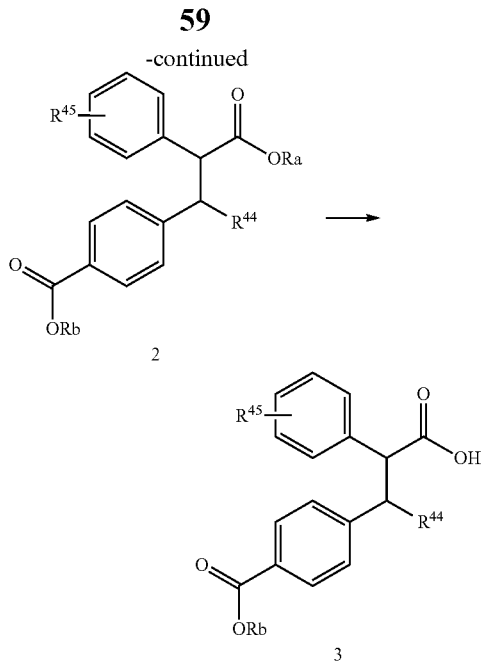

An alternative route for the synthesis of this particular building block, shown in Scheme 2, involves the condensation of an acetic acid derivative 1 with an aldehyde or a ketone leading to the α,β-unsaturated ester intermediate 4. The esters 4 can be hydrogenated under conditions that are well-documented in the literature (for example, hydrogen atmosphere and palladium on carbon as a catalyst in a solvent such as ethanol) to generate the carboxylate esters 3.

Scheme 2

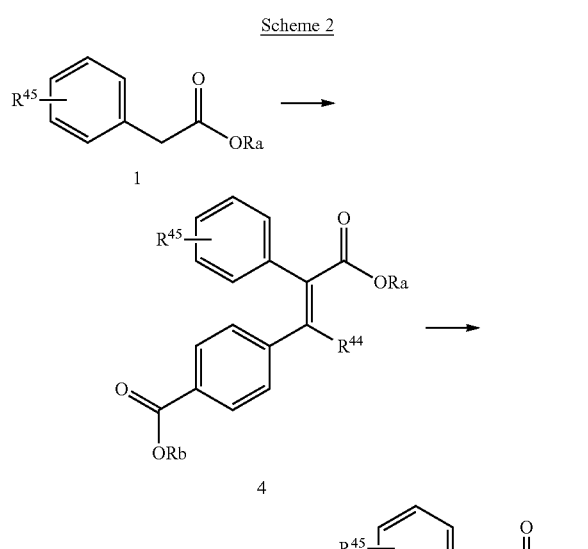

Alternatively, if $R^{44}$ in 4 is H (compound 5), 1,4-addition of an alkyl or aryl group can take place by reaction with a suitable carbon nucleophile (e.g. copper mediated reaction of alkyl or aryl lithium or an alkyl or aryl Grignard reagents) to yield compounds 3 where $R^{44}$ is alkyl (Scheme 3).

Scheme 3

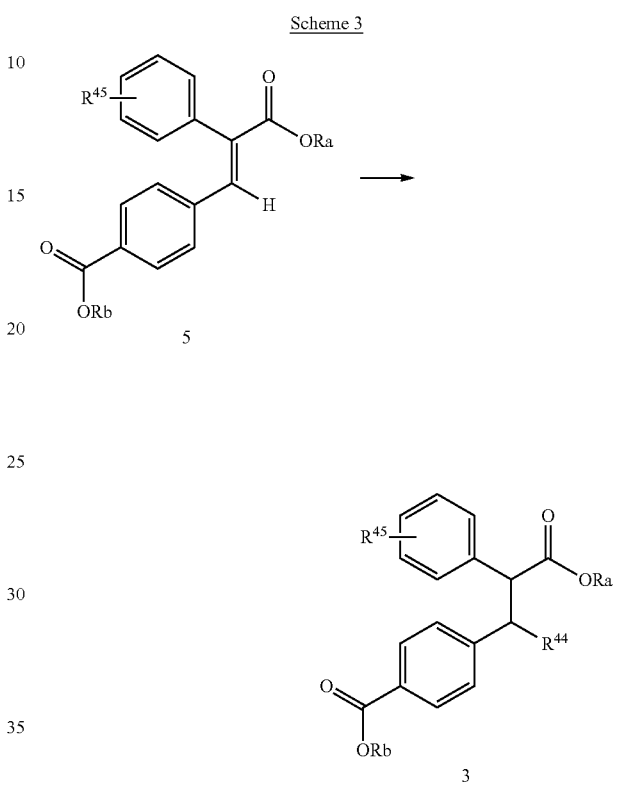

Scheme 4 shows an alternative route to precursors 5, involving the reaction of a vinylic halide 7 with an organometallic reagent such as a phenyl boronic acid or a phenyl stannane. These vinylic halides 7 (where Hal represents bromide or iodide), can be generated from the corresponding benzaldehydes and a halogenated Horner-Emmons reagent $(RO)_2P(O)CH(Hal)CO_2Ra$ (Toke et al, Tetrahedron 51, 9167 (1995),); Vanderwal et al, J. Am. Chem. Soc., 125 (18), 5393-5407 (2003)) in the presence of base or by the reaction of the same starting aldehyde with $[Ph_3P=C(IPh)CO_2Ra]$ $^{(+)[BF}4]^{(-)}$ in dichloromethane in the presence of a halide source such as tetra-n-butyl ammonium bromide or tetra-n-butyl ammonium iodide (Huang et al, J. Org. Chem 67, 8261(2002))

Scheme 4

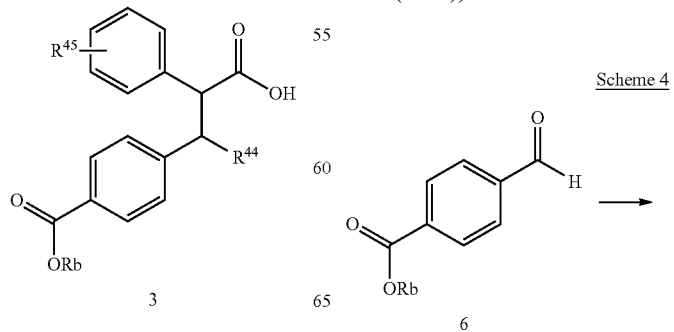

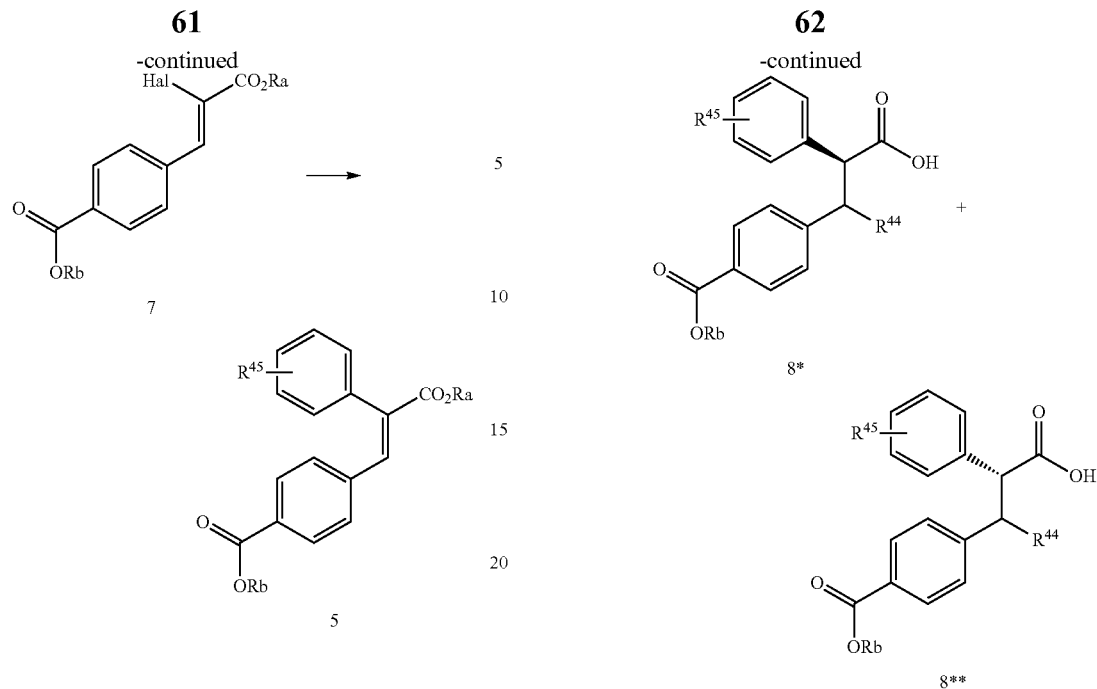

It is recognized that the carbon atom alpha to the central carbonyl group is an asymmetric center. The synthesis of compounds provided herein in enantiomerically pure form can be achieved by utilization of the methods described above if the starting material 8 exists in enantiomerically pure form. An optically pure precursor 8* or 8**, can be generated by resolution of racemic 8 or by use of synthetic methods that generate the asymmetric center in an enantioselective manner.

Resolution methods include the generation of a diastereomeric mixture of carboxylate salts with an optically active amine, which may be separated by fractional crystallization. Acidification of the individual diastereomeric salts and isolation of the carboxylic acid affords the individual enantiomers of the carboxylic acid (D. Kozma: 'CRC Handbook of Optical Resolutions via Diastereomeric Salt Formation' CRC Press, 2001). Alternatively, diastereomeric mixtures of ester or amide derivatives may be prepared by condensation of the racemic carboxylic acid with an optically active alcohol or amine, respectively; these diastereomers may be separated by chromatographic methods and/or fractional crystallization. The pure enantiomers are then generated from the individual diastereomers by reconversion to the carboxylic acid, using methods that are well established in the literature (Scheme 5).

Methods that generate the chiral center in an enantioselective manner include, but are not limited to, the alkylation of precursors containing a chiral auxiliary Xc. This may generate two diastereomers, which may be separated by fractional crystallization or chromatography (Scheme 6). After the separation of the diastereomers, they can be converted into the enantiomerically pure acid 3 and its enantiomer 3* by known procedures and further elaborated into the compounds provided herein as described in the Examples below.

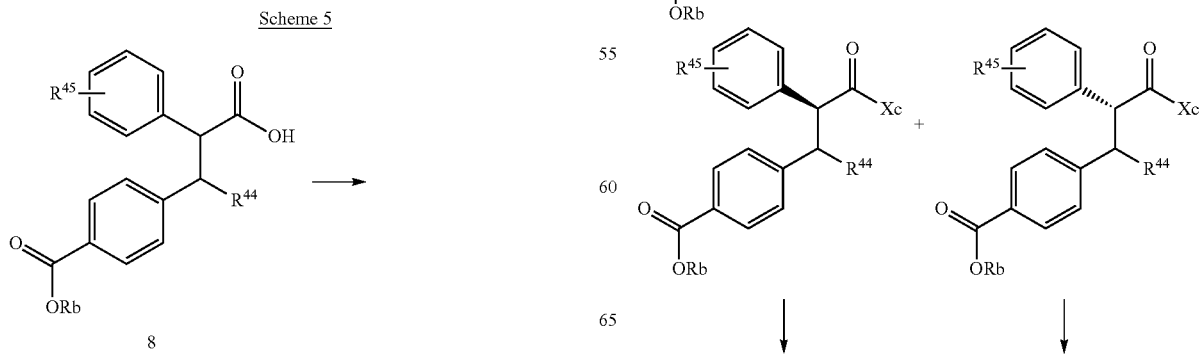

-continued

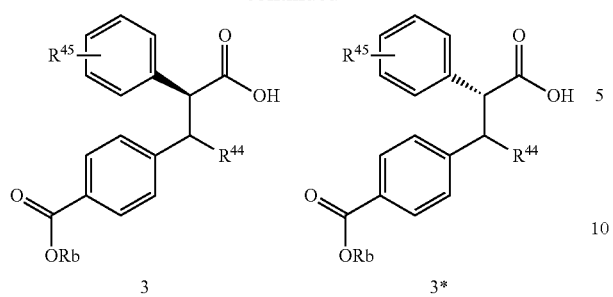

3    3*

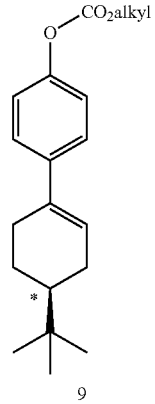

9

Asymmetric centers may be present in other positions of the molecule. As an example, substitution on a cyclohexenyl group generates a new chiral center in the compound of Example 1. This center can be established in an appropriately functionalized precursor prior to construction of the target molecule. A potential route to this chiral precursor involves the desymmetrization of a racemic ketone as illustrated in Scheme 7. The reaction of 4-t-butylcyclohexanone with a chiral amide base has been reported to generate the corresponding chiral enolate in an enantio selective manner [Busch-Petersen and Corey, Tetrahedron Letters 41, 6941 (2000), Lyapkalo et al, Synlett 1292(2001)]. Conversion of the enolate into a trifluoromethanesulfonate or a nonafluorobutanesulfonate [Busch-Petersen and Corey, Tetrahedron Letters 41, 6941(2000), Lyapkalo et al, Synlett 1292(2001)], leads to a chiral precursor that may be used in subsequent steps (A specific enantiomer is shown below, but it should be understood that either enantiomer can be synthesized by modifications of this method). The precursor 9 so obtained can then be elaborated into the single enantiomer as described above.

In a related manner, the two enantiomers of a 4-substituted cyclohex-1-enyl system can be obtained through resolution of the corresponding racemic alkene. For example, (enantiospecific or enantioselective) reaction of an alkene 10 (wherein $R^{50}$ and $R^{51}$ are different groups) generates a mixture of diastereomers which upon separation provides 11 and 12. Regeneration of the alkene provides the two enantiomers 13 and 13* (Scheme 8).

Scheme 8

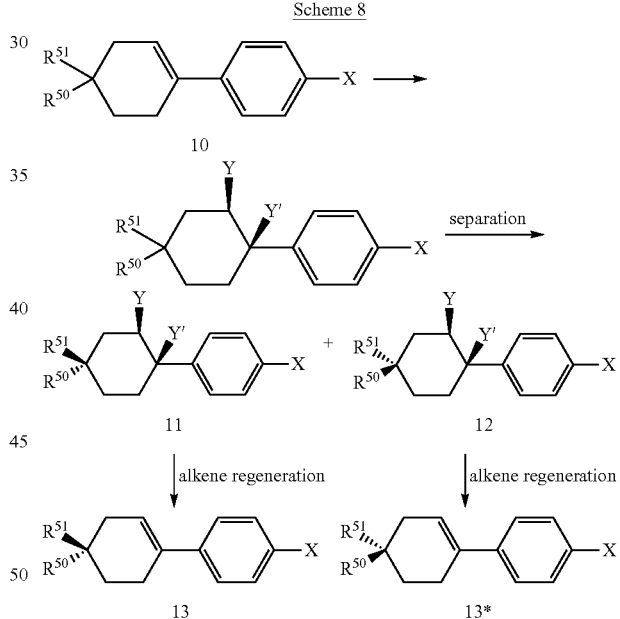

In addition to the methods described above, optically pure compounds can be obtained from their racemic parent compounds through chromatographic methods that utilize a chiral stationary phase.

A method that can be used to synthesize compounds of formula I is exemplified below (Scheme 9). The carboxylic acids 8 are converted to the corresponding amides by methods known for amide bond formation reactions. As an example, generation of an acid chloride 14 from 8 takes place under standard conditions (e.g. thionyl chloride in toluene or oxalyl chloride and catalytic DMF in dichloromethane). Treatment of acid chloride 14 with amines or anilines generates the amides 15. Alternatively, amines can be directly coupled with the carboxylic acid 8 by use of an Scheme 7

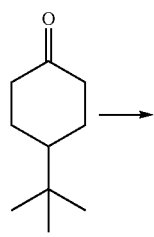

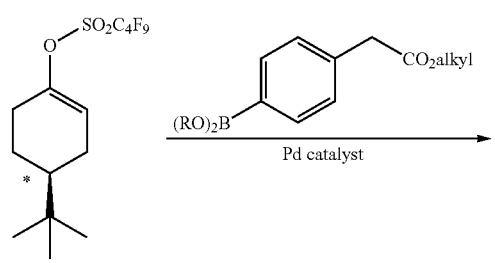

activating agent (for example, DCC or EDCI with or without a catalyst such as DMAP) to directly generate the amides 15. When L is a halo group such as bromo or iodo, aryl amides 15 with an appropriate substituent (e.g. a halo group such as bromo or iodo group on the aryl ring D) can be further functionalized through metal-mediated (e.g. Palladium) C—C bond coupling reactions to give further functionalized amides 15. Hydrolysis of the ester group of 15 (e.g. Rb=— $CH_3$ or —$C(CH_3)_3$) results in a carboxylic acid 15 (wherein Rb=—H), which can then be coupled with taurine derivatives using standard amide bond forming reactions to generate the targeted compounds 16.

The amide bond in the last step can also be formed by other reported methods known for amide bond formation, for example, reaction of an N-hydroxysuccinimidyl ester of 15 (Rb=O-succinimidyl) and taurine gives the target taurine amide derivative 16. Other activated esters (e.g. pentafluorophenyl esters) can also be used to effect the amide bond formation.

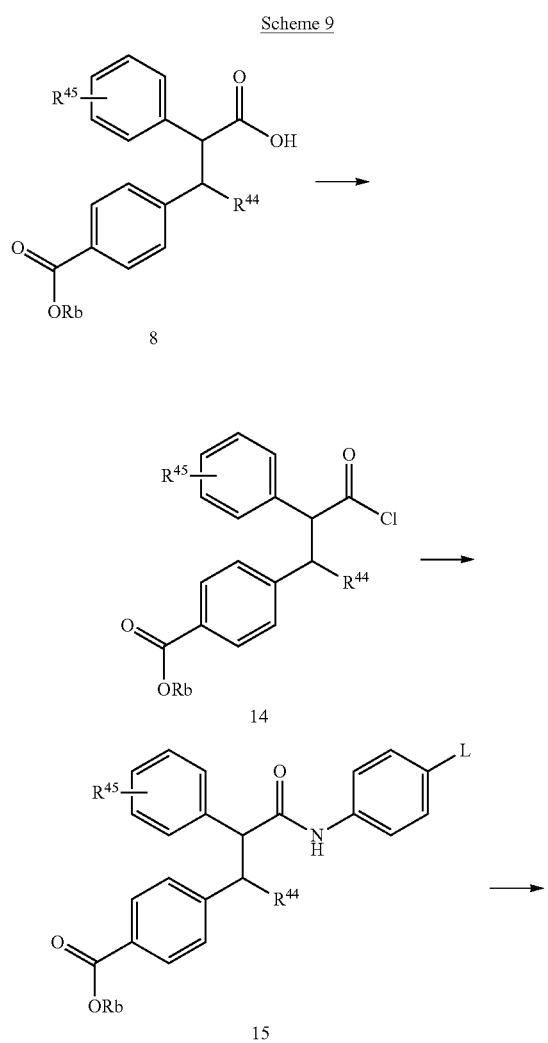

Scheme 9

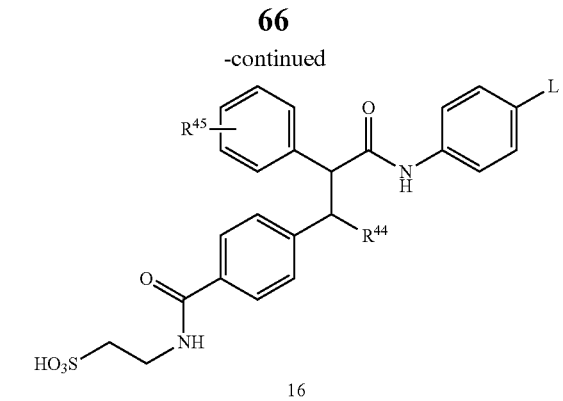

The following examples are provided so that this disclosure can be more fully understood. They should not be construed as limiting the disclosure in any way.

EXAMPLES: BIOLOGICAL EXAMPLES

Example A—Human Glucagon Receptor Activity

Compounds provided herein are dissolved in a suitable solvent (e.g., dimethylsulfoxide) at a concentration of 10 mM and then diluted in buffer (e.g., 50 mM Hepes, pH 7.4, 5 mM $MgCl_2$, 1 mM $CaCl_2$, and 0.2% BSA) to concentrations ranging from 1 nM to 100 μM. Compounds (20 μL/well) and [$^{125}$I]glucagon at the final concentration of 0.125 nM (20 μl/well) (Perkin Elmer) are added to and mixed in wells of a 96-well plate (Costar, Corning) containing 120 μL of buffer. Next, an appropriate aliquot of a membrane preparation containing the human glucagon receptor (isolated from human liver samples or obtained from a recombinant cell line) is added to the wells. The binding mixtures are incubated for 2 hrs at room temperature. In the meantime, a MultiScreen 96-well filter plate (Millipore) is treated with 200 μL of the buffer, which is vacuumed through the filter just before the binding mixtures are transferred to the plate. At the end of incubation, binding mixtures are transferred to the wells of the MultiScreen 96-well filter plate and filtered through by applying vacuum. The plate is washed once with 200 μL per well of the buffer, and the filters are dried and counted using a gamma counter.

Compounds provided herein have been shown to have high affinity for the glucagon receptor. Examples of some compounds are provided in the Table below. The Table below displays the results of testing the compounds shown in the human glucagon receptor binding assay. The column marked "stereo" indicates whether the tested compound tested was racemic or the R-isomer (rac=racemic).

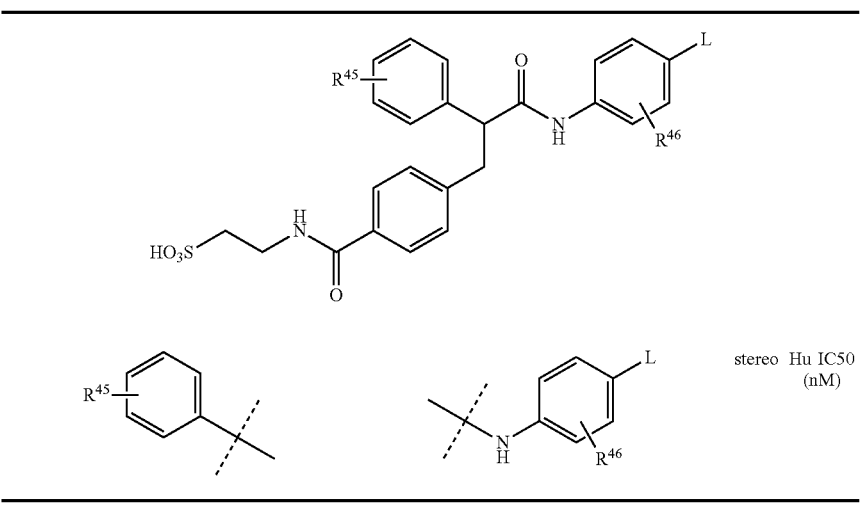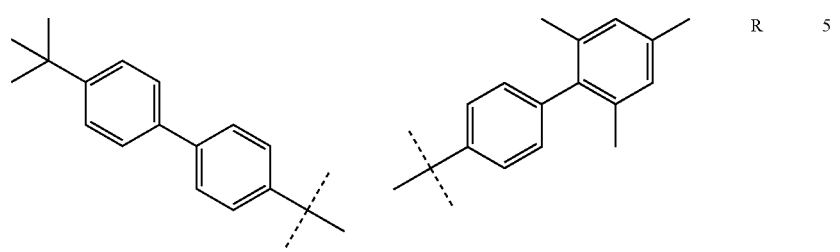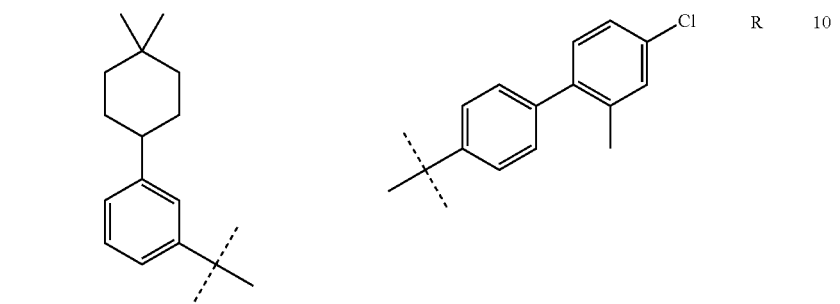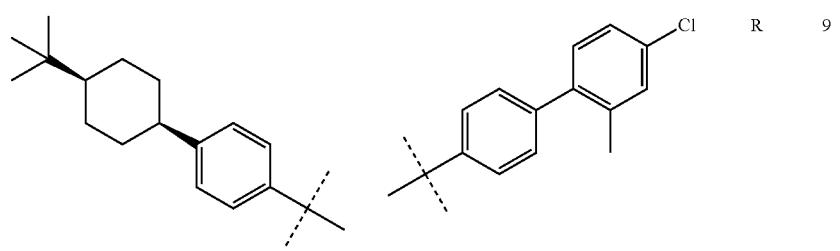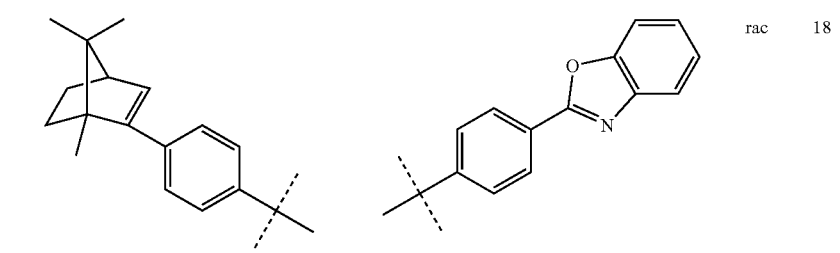

-continued
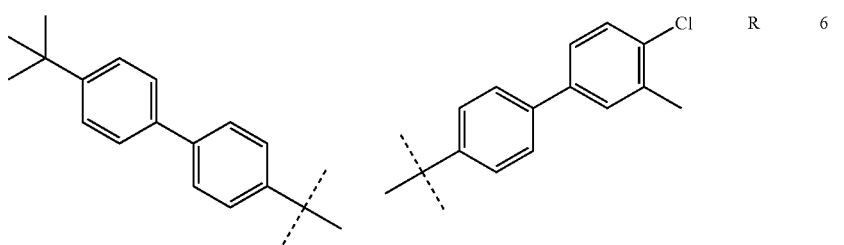
R  6
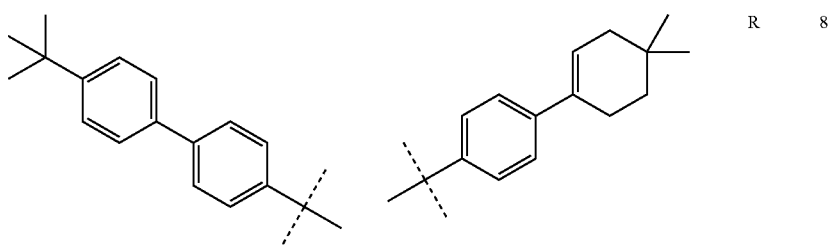
R  8
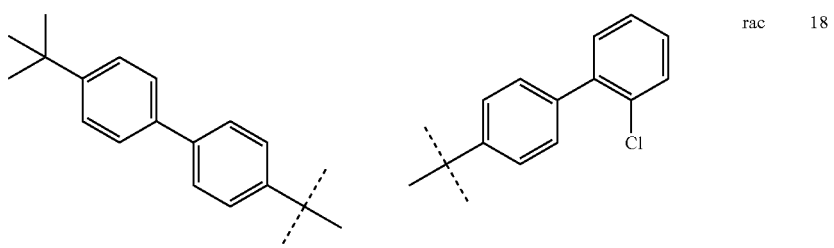
rac  18
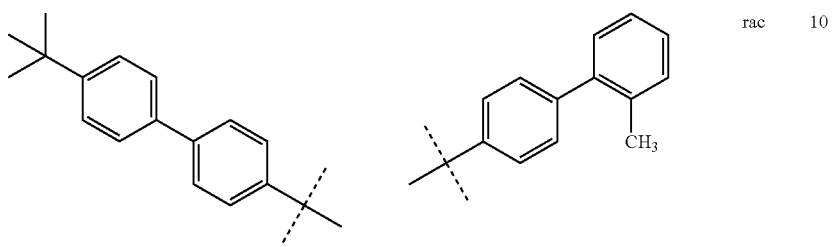
rac  10
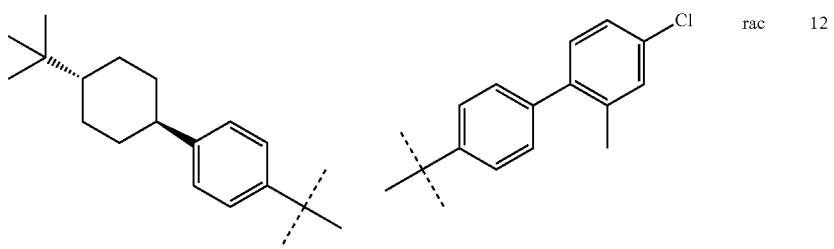
rac  12
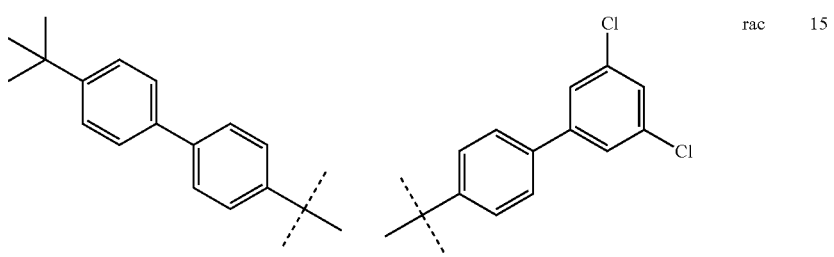
rac  15

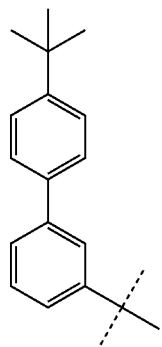 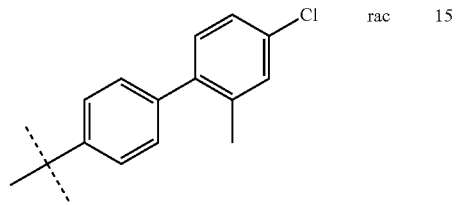 rac 15
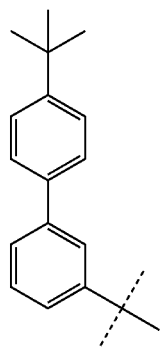 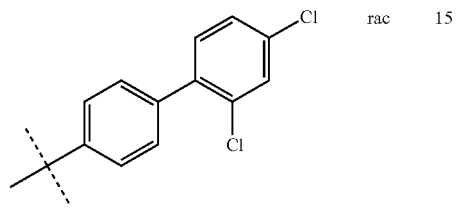 rac 11
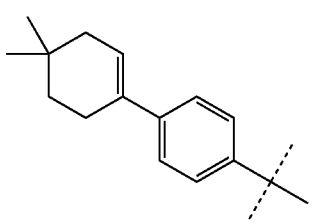 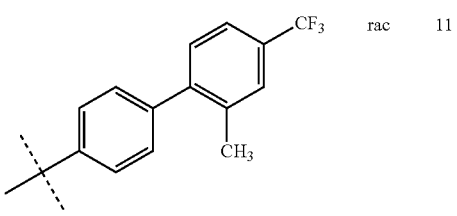 rac 15
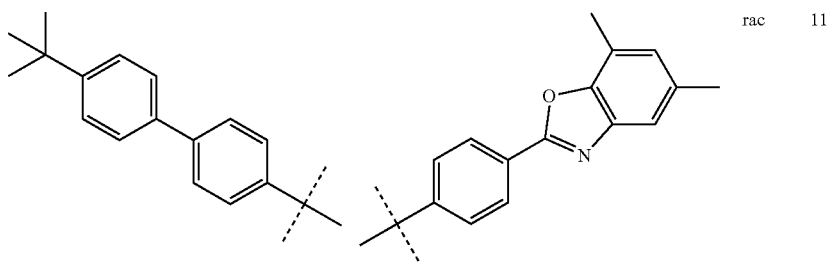 rac 11
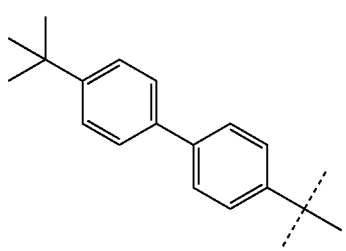 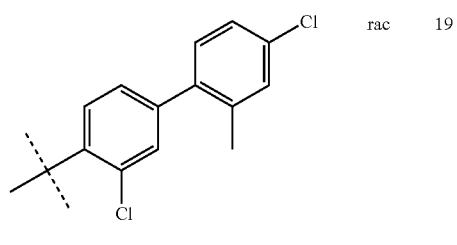 rac 19

-continued
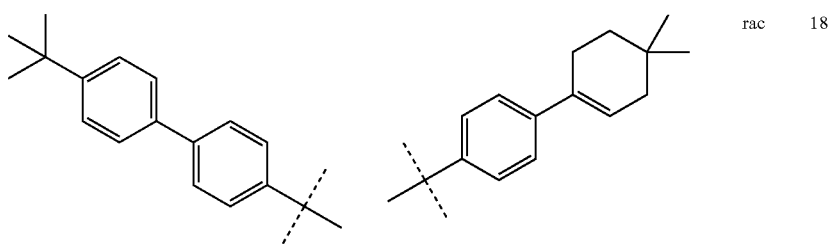 rac 18
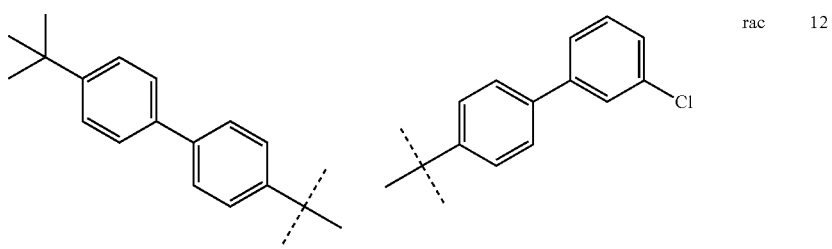 rac 12
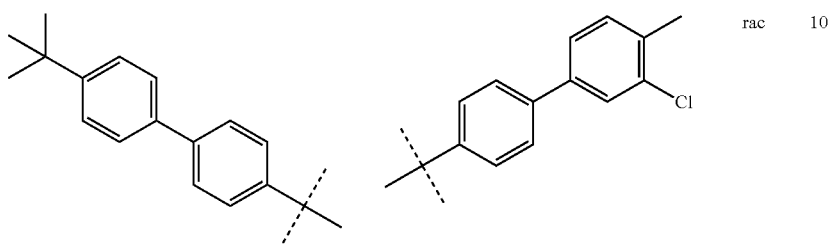 rac 10
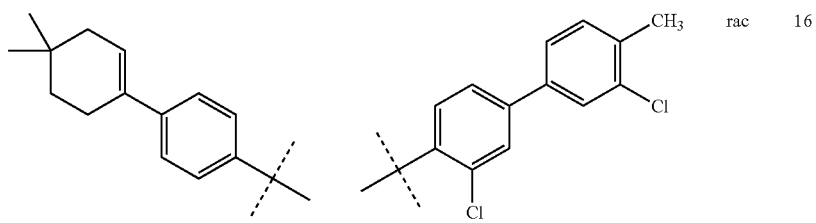 rac 16
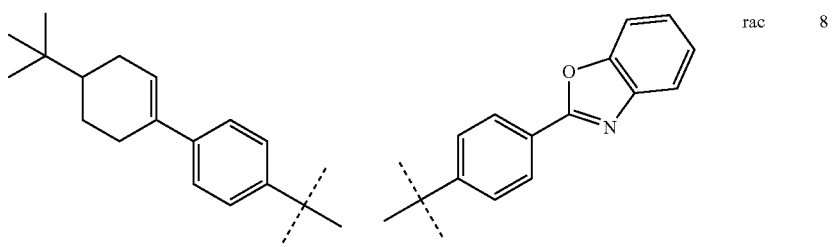 rac 8
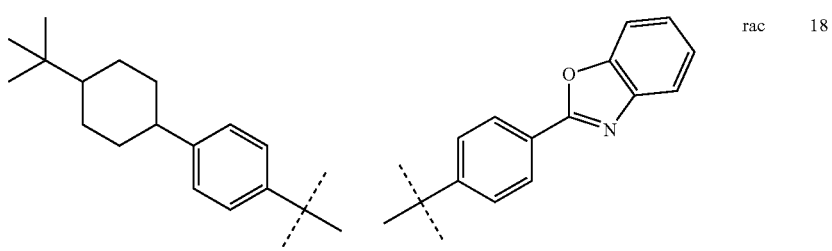 rac 18

-continued
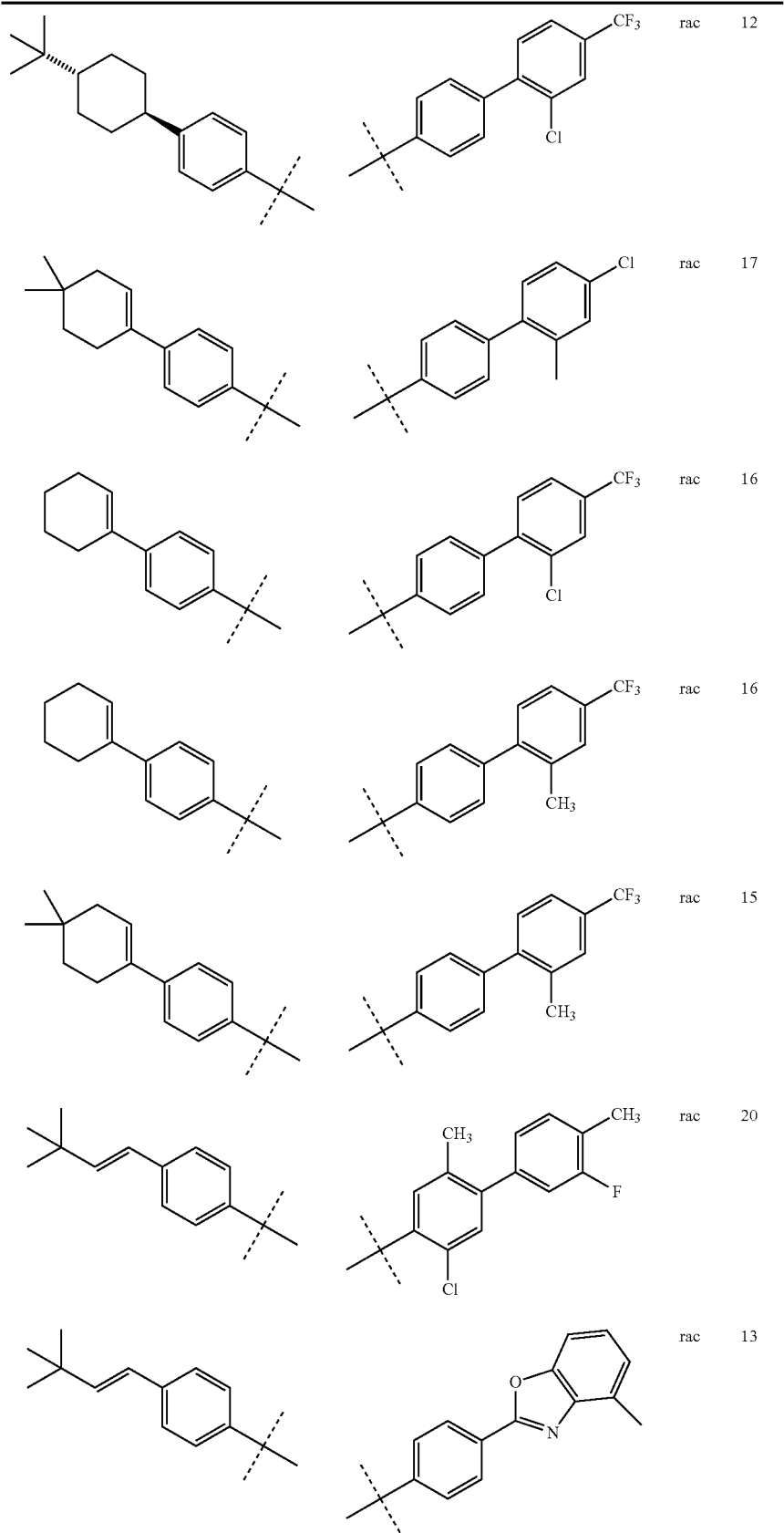

-continued
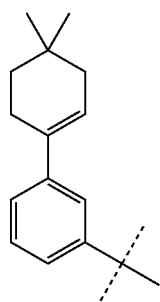 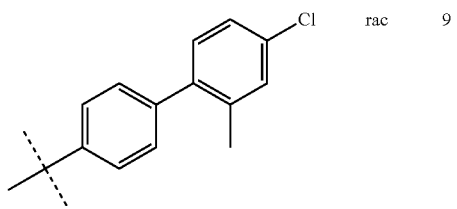 rac 9
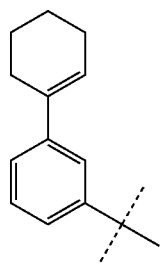 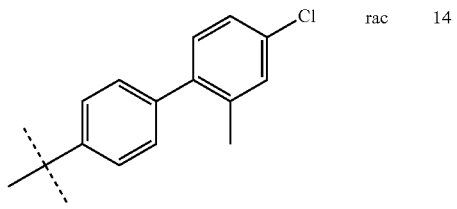 rac 14
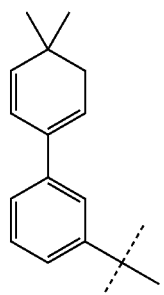 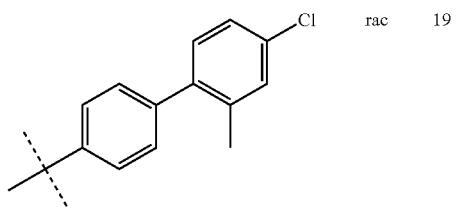 rac 19
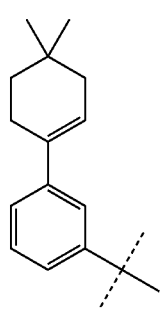 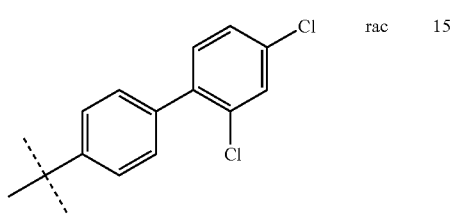 rac 15
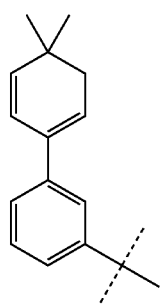 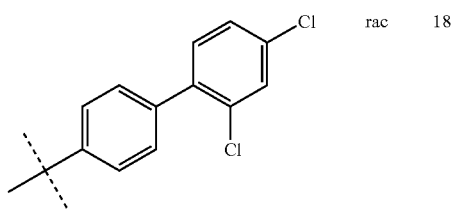 rac 18

-continued
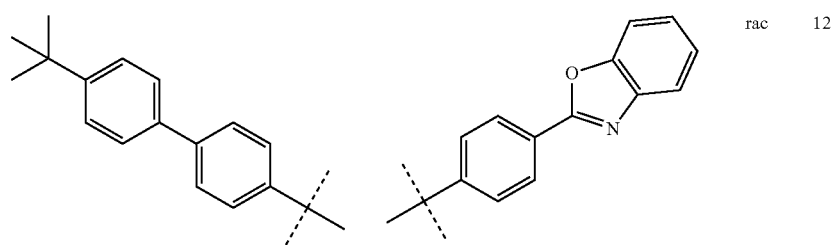 rac 12
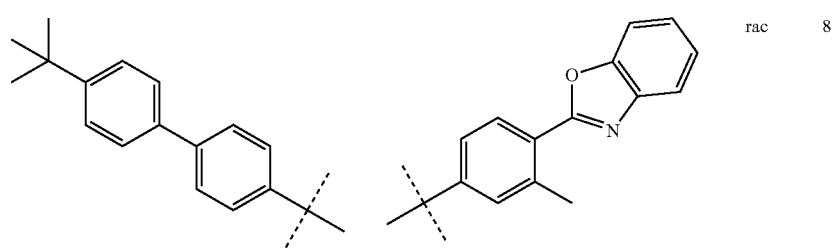 rac 8
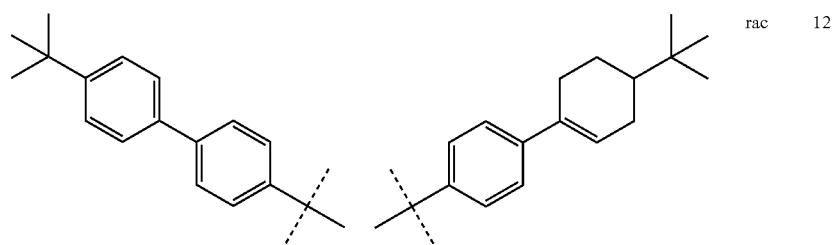 rac 12
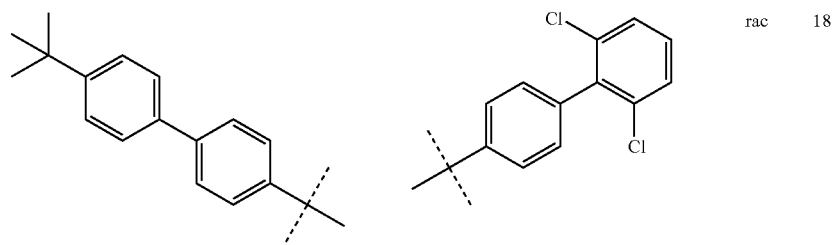 rac 18
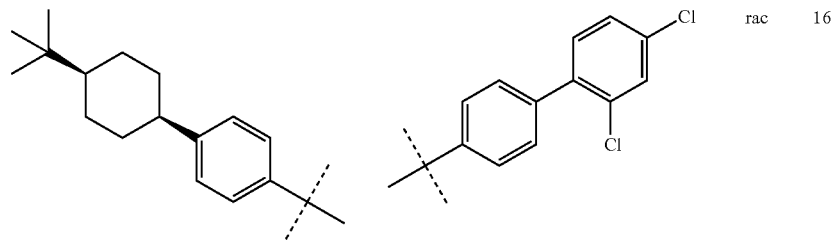 rac 16
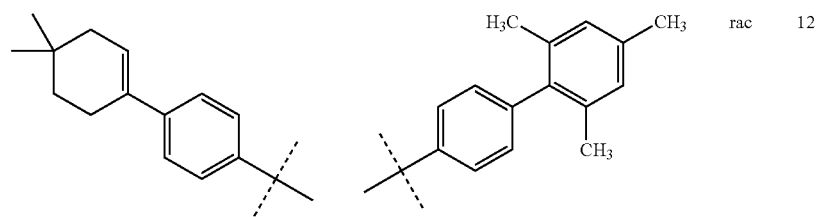 rac 12

-continued
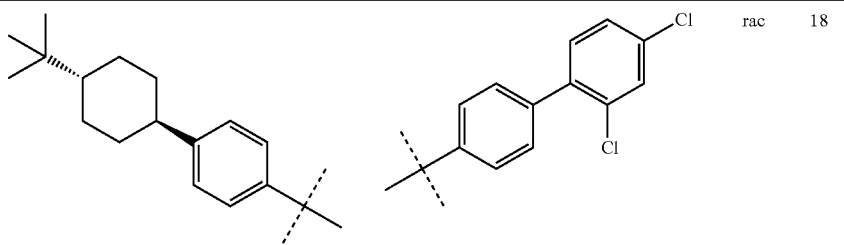
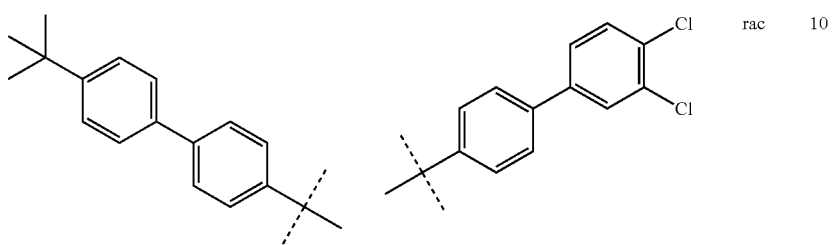
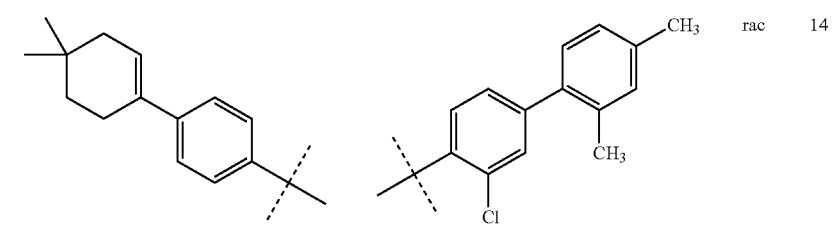
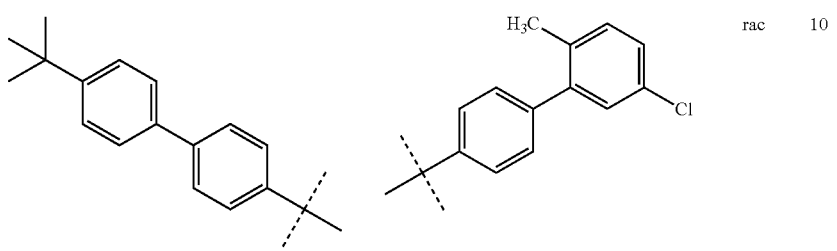
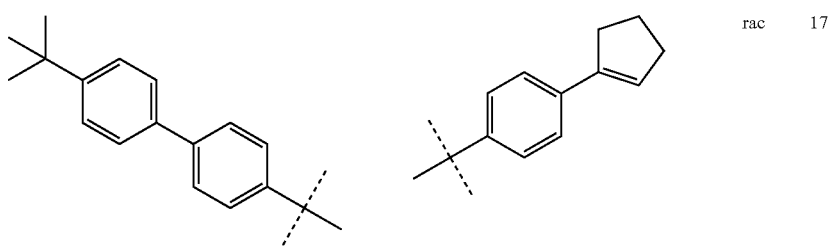
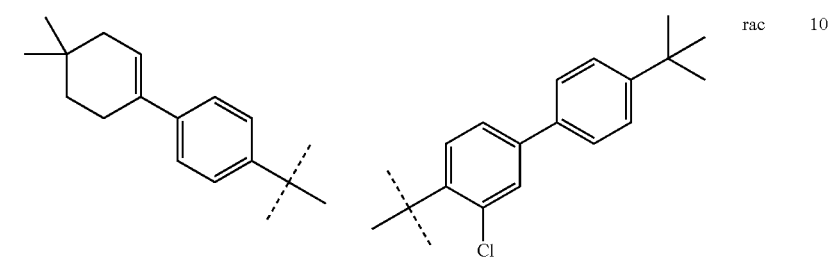

The R-enantiomer compounds of Formula I provided herein which have been tested displace radiolabeled glucagon from the human glucagon receptor with an $IC_{50}$ of <15 nM.

The S-enantiomer compounds of Formula II provided herein which have been tested displace radiolabeled glucagon from the human glucagon receptor with an $IC_{50}$ of <65 nM.

For certain compounds, the R-enantiomer displays up to 5-fold higher affinity for the human glucagon receptor than the S-enantiomer.

The Table below shows sample comparative data from some R-enantiomers. The Table displays the relative potency in the human glucagon receptor binding assay of the R- vs. S-isomers of the compounds shown. (The stereocenter being changed is marked with an asterisk; the R-isomer is shown in the drawing.)

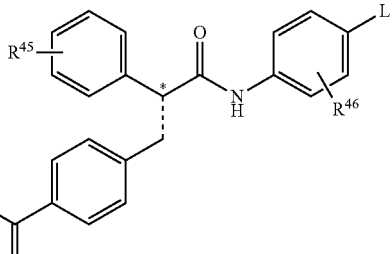

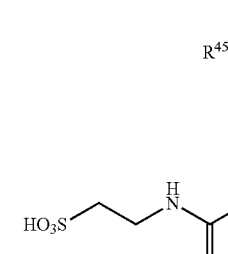

| | | Hu IC50 (nM) | |
|---|---|---|---|
| | | R | S |
| 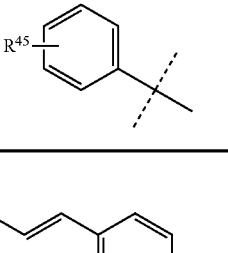 | 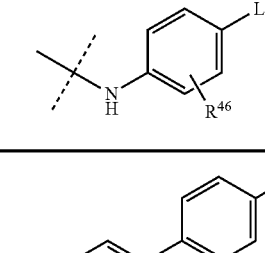 | 14 | 61 |
| 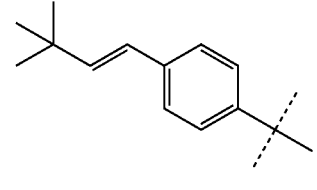 | 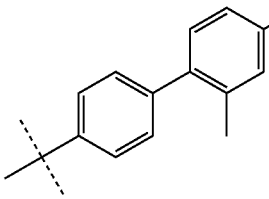 | 6 | 20 |
| 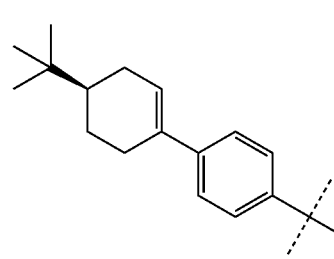 | 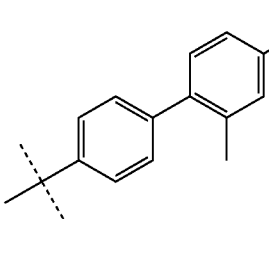 | 7 | 19 |

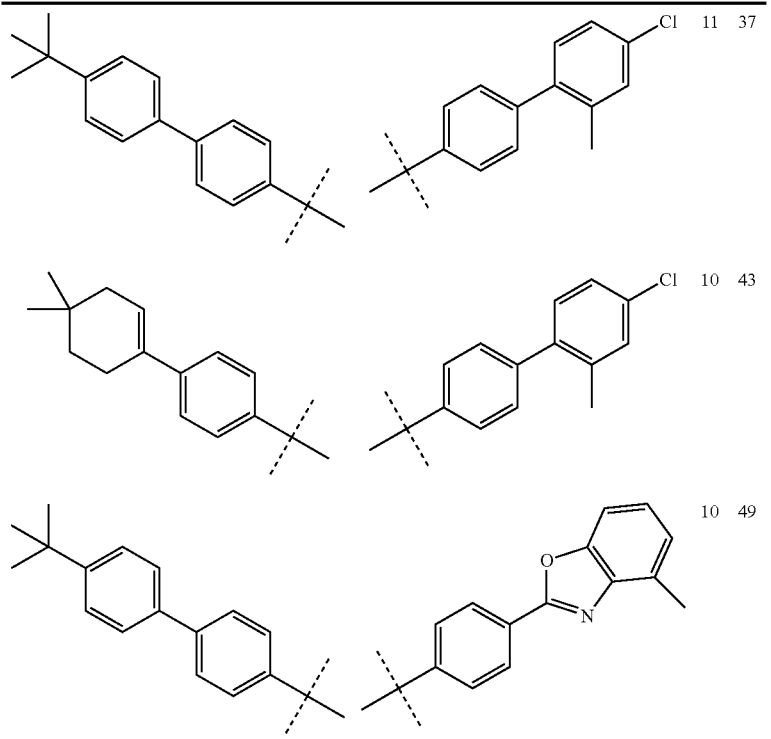

Conclusion:

The compounds disclosed herein display nanomolar affinity for the human glucagon receptor. For certain compounds, the R-enantiomer displays up to 5-fold higher affinity for the human glucagon receptor than the S-enantiomer.

Example B—Functional Antagonism in Hepatocytes from Various Species

Primary human, monkey, dog, rat, or mouse hepatocytes are seeded onto collagen-coated 24-well plates in Williams E medium (supplemented with 10% fetal bovine serum) and incubated at 37° C. overnight in M199 medium (supplemented with 15 mM glucose and 10 nM human insulin). The following day cells are washed twice with a glucose-free Kreb-bicarbonate buffer, pH 7.4, containing 0.1% BSA. Cells are then incubated at 37° C. with the aforementioned buffer containing 1 nM glucagon and varying concentrations of a glucagon antagonist (0-100 microM). Control wells without glucagon or antagonist are also included. After 1 hour, an aliquot of the medium is removed and analyzed for glucose content by means of the glucose oxidase method. The background glucose levels observed in the control wells are subtracted from the glucagon and antagonist containing wells. A graph of % glucose concentration vs drug concentration is plotted and an EC50 value for inhibition of glucose production generated using Sigmaplot software (SAS, Cary, N.C.). Alternatively, intracellular cAMP levels are measured using standard kits and EC50 values determined by plotting these levels against drug concentration. Antagonists of the glucagon receptor inhibit glucagon-induced cAMP production.

The R-enantiomer compounds of Formula I provided herein which have been tested show functional antagonism of glucose production in human hepatocytes with an $EC_{50}$ of <40 nM.

The S-enantiomer compounds of Formula II provided herein which have been tested show functional antagonism of glucose production in human hepatocytes with an $EC_{50}$ of <1200 nM.

For certain compounds, the R-enantiomer displays up to 50-fold greater functional antagonism in human hepatocytes than the S-enantiomer.

Conclusion:

The compounds disclosed herein display significant functional antagonism of glucose production in human hepatocytes. For certain compounds, the R-enantiomer displays up to 50-fold greater functional antagonism in human hepatocytes than the S-enantiomer.

Example C—Glucose Lowering in Diabetic Animals

The effects of compounds provided herein on blood glucose levels are assessed in animal models of type 1 or 2 diabetes such as, but not limited to, the db/db mouse, the Zucker fatty (ZF) rat, the Zucker diabetic (ZDF) rat, the glucagon-challenged dog, the alloxan- or streptozotocin-treated mouse or rat, the NOD mouse or the BB rat.

Compounds are dissolved in an appropriate vehicle such as polyethylene glycol-400 or cyclodextrin and administered to animals at doses of 0.1 to 100 mg/kg either by intraperitoneal injection, intravenous injection, or oral gavage. Animal models used in this evaluation [e.g., the db/db mouse, the ZF rat, the ZDF rat, the glucagon-challenged (0.3-5 µg/kg) dog, the alloxan- or streptozotocin-treated mouse or rat, the NOD mouse, or BB rat] are either freely-feeding or fasted from 3 to 24 hours prior to compound administration. In some instances, animals may be subjected to a glucose tolerance test following compound administration by intravenous or oral administration of up to 2 g/kg of glucose.

Blood glucose levels are assessed in blood samples obtained by tail bleed or by sampling an appropriate blood vessel by means of a syringe or catheter. Glucose is measured using a portable glucometer such as the OneTouch or HemoCue meters at regular time intervals for up to 24 hours. The extent of blood glucose lowering elicited by the compounds of Formula I, II or III is determined by comparison to those in control animals administered only the vehicle. The percentage of blood glucose lowering attained is calculated relative to blood glucose levels in vehicle-treated nondiabetic or non-glucagon-challenged control animals.

Example D—Glucose Lowering in db/db Mice

To assess the effects of compounds provided herein on blood glucose levels in the db/db mouse, an animal model of type 2 diabetes, compounds are dissolved in polyethylene glycol-400 and administered by oral gavage to db/db mice in the freely-feeding state at doses of 30 and/or 100 mg/kg. Blood glucose levels are assessed in blood samples obtained by tail bleed at baseline (prior to drug administration) and at regular time intervals over 24 hrs using a portable glucometer such as the OneTouch or HemoCue meters. The magnitude of blood glucose lowering elicited by the compounds provided herein is determined by comparison to those in db/db mice administered only the vehicle. The percentage glucose lowering is calculated by factoring in the blood glucose levels of vehicle-treated lean db/+(heterozygote) mice, with 100% representing the normalization of blood glucose levels from the hyperglycemic state (vehicle-treated db/db mice) to the normoglycemic state (vehicle-treated db/+mice).

The compounds disclosed herein which have been tested lowered blood glucose of db/db mice in the freely-feeding state. In particular, the percentage blood glucose lowering achieved ranged from 36 to 57% relative to lean control animals.

Conclusion:

The compounds disclosed herein have pronounced antihyperglycemic activity in animal models of type 2 diabetes and may therefore have utility for the treatment of type 2 diabetes.

EXAMPLES—CHEMICAL SYNTHESIS
EXAMPLES

Example 1: Sodium; 2-{4-[2-[4-(4-tert-butyl-cyclohex-1-enyl)-phenyl]-2-(4'-chloro-2'-methyl-biphenyl-ylcarbamoyl)-ethyl]-benzoylamino}-ethanesulfonate Step 1: 4-[2-(4-Bromophenyl)-2-carboxy-ethyl]-benzoic acid methyl ester

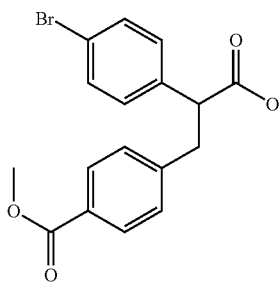 [SMILES: COC(=O)c1ccc(CC(C(=O)O)c2ccc(Br)cc2)cc1]

In a 3-neck flask, a solution of 4-bromophenyl acetic acid (26.91 g) in THF (485 mL) was cooled to <10° C. under a nitrogen atmosphere. A solution of LiHMDS in THF (263 mL, 1.0 M) was added dropwise, ensuring that the internal temperature remained at <10° C. After the addition was complete, the mixture was stirred at 0° C. for about 15 min. The cooling bath was the removed and the reaction mixture was allowed to warm up to 20° C.

The reaction mixture was then cooled to <−60° C. From an addition funnel, a solution of 4-bromomethyl methylbenzoate (29.53 g) in THF (270 mL) was added dropwise, ensuring that the temperature did not rise above −60° C. After the addition was complete, the mixture was stirred at −60° C. for about 15 min, and poured over 300 mL of cold 1M aqueous HCl (saturated with sodium chloride). The organic layer was washed with 1M aqueous HCl (saturated with sodium chloride). The combined aqueous layers were extracted with toluene (50 mL). The combined organic phases were then dried over magnesium sulfate and concentrated under reduced pressure. The crude residue was recrystallized from toluene to yield the carboxylic acid as a white solid.

HNMR (300 MHz, DMSO-$d_6$): 12.54 (1H, broad s), 7.82 (2H, d, J=6.4 Hz), 7.49 (2H, d, J=6.7 Hz), 7.32 (2H, d, J=8.2 Hz), 7.26 (2H, d, J=8.5 Hz), 3.95 (1H, t, J=7.9 Hz), 3.81 (3H, s), 3.3 (1H, m, overlaps with residual HOD), 3.03 (1H, m)

Step 2: 4-{2-(4-Bromo-phenylcarbamoyl)-2-[4-(4-tert-butyl-cyclohex-1-enyl)-phenyl]-ethyl}-benzoic acid methyl ester

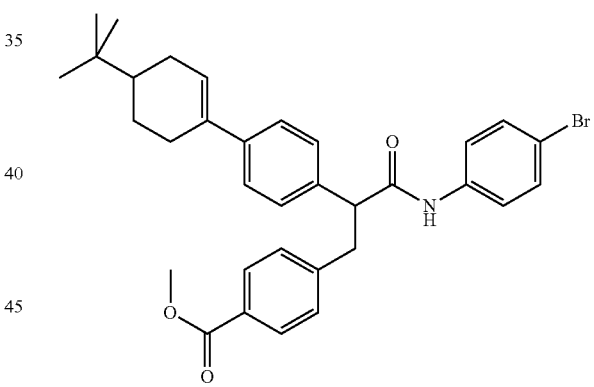

To a solution of 4-[2-(4-Bromophenyl)-2-carboxy-ethyl] benzoic acid methyl ester (step 1 above, 0.6 g) in THF: ethanol:water (6 mL:3 mL:1.5 mL) added 4-t-butyl-1-cyclohexenyl-boronic acid (0.5 g), $PdCl_2(P(o-tolyl)_3)_2$, and sodium carbonate (0.7 g). The resulting mixture was heated at 125° C. for a 1 h period. The reaction was then cooled to room temperature, treated with an excess of aqueous HCl (1M) and the resulting heterogeneous mixture was filtered through a celite pad. The organic phase was dried over sodium sulfate and concentrated under reduced pressure. The crude residue was dissolved in toluene (25 mL), treated with thionyl chloride (0.26 mL) and heated at 100° C. for a 1h period. The toluene was removed under reduced pressure. The resulting acid chloride was redissolved in toluene (15 mL), treated with 4-bromoaniline (0.3 g) and diisopropyl ethyl amine (0.3 mL), and heated at 100° C. for a 1 h period. After cooling to room temperature, the mixture was partitioned between ethyl acetate and 1M aqueous HCl. The organic layer was washed (water, saturated sodium chloride), dried over magnesium sulfate and concentrated under reduced pressure. The product obtained was carried to the next step without further purification.

Step 3: Sodium; 2-(4-{2-(4-bromo-phenylcarbamoyl)-2-[4-(4-tert-butyl-cyclohex-1-enyl)-phenyl]-ethyl}-benzoylamino)-ethanesulfonate

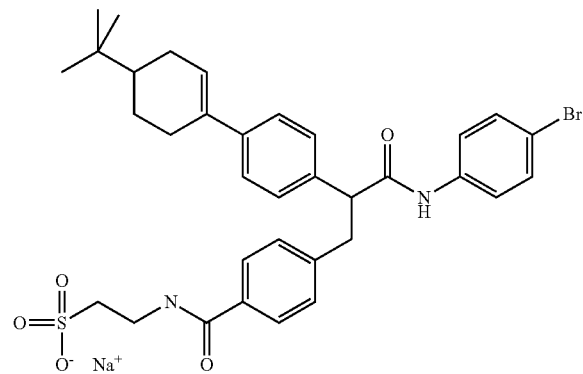 [SMILES: CC(C)(C)C1CC=C(c2ccc(C(Cc3ccc(C(=O)NCCS(=O)(=O)[O-])cc3)C(=O)Nc3ccc(Br)cc3)cc2)CC1 ; [Na+]]

A solution of 4-{2-(4-Bromo-phenylcarbamoyl)-2-[4-(4-tert-butyl-cyclohex-1-enyl)-phenyl]-ethyl}-benzoic acid methyl ester (Step 2, 0.8 g) in THF:methanol:water (8 mL:6 mL:2 mL) was treated with lithium hydroxide (0.4 g) and stirred at room temperature for 16 h. Added an excess of aqueous HCl (1M) and extracted with ethyl acetate. The organic phase was washed with saturated sodium chloride in water and dried over sodium sulfate. The solvents were then removed under reduced pressure. The residue obtained was dissolved in DMF (10 mL), and treated with EDCI (0.4 g), HOBt-$H_2O$ (0.32 g), taurine (0.26 g) and diisopropyl ethyl amine (0.71 mL). The reaction mixture was then stirred at room temperature for a 16 h period. The solvent was removed under reduced pressure. The residue was partitioned between ethyl acetate and 1M aqueous HCl. The organic phase was washed with saturated sodium chloride, and concentrated. The residue in methanol was treated with an excess of sodium hydroxide and loaded on top of a C-18 reverse phase flash chromatography column. The column was eluted with an acetonitrile-water gradient to afford the sodium salt of the sulfonate as a white solid LCMS m/z: 665.6 $[C_{34}H_{38}N_2O_5BrS]^-$ Step 4

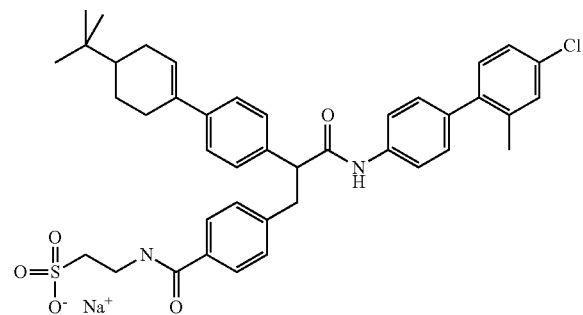 [SMILES: Cc1cc(Cl)ccc1-c1ccc(NC(=O)C(Cc2ccc(C(=O)NCCS(=O)(=O)[O-])cc2)c2ccc(C3=CCC(C(C)(C)C)CC3)cc2)cc1 ; [Na+]]

To a solution sodium; 2-(4-{2-(4-bromo-phenylcarbamoyl)-2-[4-(4-tert-butyl-cyclohex-1-enyl)-phenyl]-ethyl}-benzoylamino)-ethanesulfonate (Step 3 above, 96 mg) in DME:ethanol:water (2 mL:1 mL:0.5 mL) added 4-t-butyl-1-cyclohexenyl-boronic acid (0.5 g), $PdCl_2(P(o-tolyl)_3))_2$, and sodium carbonate (0.7 g). The resulting mixture was heated at 125° C. for a 1 h period. The reaction was then cooled to room temperature, treated with an excess of aqueous HCl (1M) and the resulting heterogeneous mixture was filtered through a celite pad. The mixture was partitioned (ethyl acetate/water). The organic phase was washed with saturated sodium chloride, and concentrated. The residue in methanol was treated with an excess of sodium hydroxide and loaded on top of a C-18 reverse phase flash chromatography column. The column was eluted with an acetonitrile-water gradient to afford the sodium salt of the sulfonate as a white solid LC-MS m/z=711.6 $[C_{44}H_{44}N_2O_5ClS]^-$ Example 2: Sodium-2-(4-{2-(4'-chloro-2'-methyl biphenyl-4-ylcarbamoyl)-2-[3-(4,4-dimethyl-cyclohexyl)-phenyl]-ethyl}-benzoylamino-ethane sulfonic acid Step 1: 4-Benzyl-3-[2-(3-bromo-phenyl)-acetyl]-oxozolidin-2-one

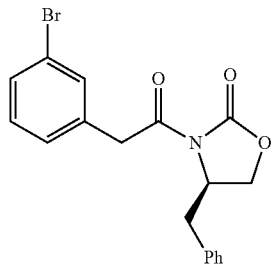 [SMILES: O=C(Cc1cccc(Br)c1)N1C(=O)OC[C@H]1Cc1ccccc1]

To a solution of (3-bromo-phenyl)-acetic acid (5.0 g, 23.2 mmol) in $CH_2Cl_2$ (50 mL) at room temperature was added oxalyl chloride (5.86 g, 46.5 mmol). The reaction mixture was stirred at room temperature for overnight and the solvent was removed under reduced pressure. The residue was dried under vacuum for 3-4 h and used without further purification. In a separate flask, to a stirred solution of R-(+)-4-benzyl-oxazolidinone (4.34 g, 24.5 mmol) in THF (30 mL) at −78° C. was added n-BuLi (26.7 mL, 26.7 mmol, 1.0 M solution in hexane). The reaction mixture was stirred for 1 h, at −78° C., then the crude acid chloride (5.2 g, 22.3 mmol) in THF was added dropwise. The mixture was stirred for 2 h at −78° C. and allowed to warm to rt and stirred for another hour (monitored by TLC). The reaction was quenched with saturated $NH_4Cl$ solution (100 mL) and stirred for 10 min. The reaction mixture was extracted with ethyl acetate (2×250 mL) and the combined organic layers were washed with brine, dried over $MgSO_4$ and concentrated under reduced pressure. The crude product was purified by column chromatography on silica gel, eluting with EtOAc-hexanes (5-25%) to afford 4-benzyl-3-[2-(3-bromo-phenyl)-acetyl]-oxozolidin-2-one.

$^1$H NMR (300 MHz, $CDCl_3$): 7.51 (d, J=2.1 Hz, 1H), 744 (dd, J=3.9, 4.8 Hz, 1H), 7.32-7.20 (m, 6H), 7.15 (d, J=3.9 Hz, 1H), 4.60 (m, 1H), 4.30 (m, 2H), 4.26-4.19 (m, 3H), 3.27 (dd, J=1.8, 8.1 Hz, 1H), 2.78 (dd, J=5.4, 7.8 Hz, 1H); TLC

Step 2: 4-{3-(4-Benzyl-2-oxo-oxazolidin-3-yl)-2-[4-(3-bromophenyl)-3-oxo-propyl]-benzoic acid tert-butyl ester

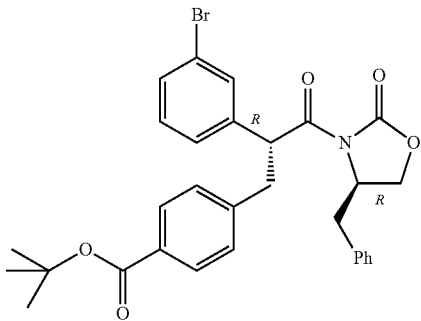

To a stirred solution of 4-benzyl-3-[2-(3-bromo-phenyl)-acetyl]-oxozolidin-2-one (4.02 g, 10.7 mmol) in anhydrous THF (50 mL) was added LiHMDS (16.5 mL, 16.5 mmol. 1.0 M solution in THF) at −78° C. The reaction mixture was stirred for 1.5 h at −78° C., and then tert-butyl-4-bromo methyl benzoate (3.75 g, 11.8 mmol, in THF 10 mL) was added dropwise, stirred for 2 h at −78° C. and then allowed to warm to rt for 1 h. After completion of the reaction quenched with saturated NH$_4$Cl solution (100 mL) and stirred for 10 min. The reaction mixture was extracted with ethyl acetate (2×250 mL) and the organic layer was washed with brine, dried over Na$_2$SO$_4$ and concentrated under reduced pressure. The crude product was precipitated from minimum amount of EtOAc and hexane at room temperature to afford 4-{3-(4-Benzyl-2-oxo-oxazolidin-3-yl)-2-[4-(3-bromophenyl)-3-oxo-propyl}-benzoic acid tert-butyl ester as a yellow solid $^1$H NMR (300 MHz, CDCl$_3$): δ 7.75 (d, J=6.3 Hz, 2H), 7.44 (d, J=2.1 Hz, 2H), 7.26-7.04 (m, 9H), 6.79 (dd, J=1.8, 5.7 Hz, 2H), 5.29 (dd, J=2.1, 6.3 Hz, 1H), 3.89 (s, 3H), 3.83 (d, J=7.5 Hz, 1H), 3.41 (dd, J=8.4, 13.8 Hz, 1H), 3.05 (dd, J=7.2, 13.5 Hz, 1H); TLC conditions: Uniplate silica gel, 250 microns; mobile phase=ethyl acetate-hexanes (1:4); R$_f$=0.45.

Step 3: 4-[2-carboxy-2-(3-bromo-phenyl)-ethyl]-benzoic acid tert-butyl ester (5)

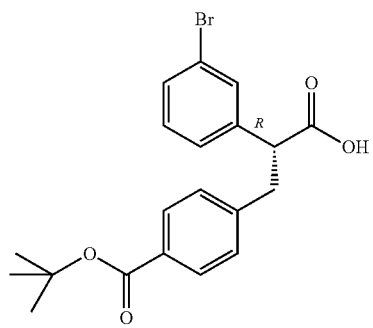

To a stirred solution of 4-{3-(4-benzyl-2-oxo-oxazolidin-3-yl)-2-[4-(3-bromophenyl)-3-oxo-propyl}-benzoic acid tert-butyl ester (2.3 g, 3.7 mmol) in THF/H$_2$O (20 mL) (3:1) at room temperature were added H$_2$O$_2$ (1.25 g, 37.0 mmol 35% in H$_2$O) followed by LiOH (0.62 g, 14.8 mmol). The reaction mixture was stirred for 3 h, at room temperature and quenched with 0.1 N HCl. The reaction mixture was extracted with ethyl acetate (100 mL) and dried over MgSO$_4$, filtered and concentrated under reduced pressure to afford the crude acid. This crude product was purified by column chromatography on silica gel, eluting with CH$_2$Cl$_2$/MeOH 2%-15% to afford 4-[2-carboxy-2-(3-bromo-phenyl)-ethyl]-benzoic acid tert-butyl ester (1.5 g, 75%)

$^1$H NMR (300 MHz, DMSO-d$_6$): δ 12.52 (s, 1H), 7.77 (d, J=8.4 Hz, 2H), 7.48 (d, J=8.7 Hz, 2H), 7.28 (d, J=8.4 Hz, 2H), 7.22 (d, J=8.4 Hz, 2H), 3.93 (t, J=7.8 Hz, 1H), 3.30 (dd, J=8, 4, 13.8 Hz, 1H), 3.0 (dd, J=8.1, 13.8 Hz, 1H), 1.49 (s, 9H), TLC conditions: Uniplate silica gel, 250 microns; mobile phase=CH$_2$Cl$_2$/MeOH (10%); R$_f$=0.4. Chiral HPLC conditions: Kromasil 100-5-TBB chiral column 250×4.6 cm, (5% hexane/2-propanol to 30%), 35 min, flow rate 1 mL/min, RT=12.41 min (enantiomeric excess: >96%)

Step 4: 4'-Chloro-2'-methyl-biphenyl-4-amine

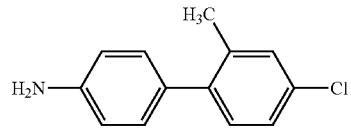

A mixture of 4-iodo-aniline (25.0 g, 114.1 mmol), 2-methyl-4-chlorophenyl-boronic acid (29.17 g, 171.1 mmol), PdCl$_2$P(o-tolyl)$_3$)$_2$(11.66 g, 14.8 mmol), and Na$_2$CO$_3$ (60.49 g, 570.7 mmol) in DME/EtOH/H$_2$O (100/50/25 mL) was heated 125° C. for 2 h. The reaction mixture was cooled to room temperature, filtered and washed with EtOAc (200 mL). The solvent was removed under reduced pressure. The crude mixture was extracted with ethyl acetate (500 mL) and the organic layer was washed with brine, dried over Na$_2$SO$_4$ and concentrated under reduced pressure. The resulting crude was purified by column chromatography on silica gel, eluting with 5-30% Hexane/EtOAc to afford 4'-Chloro-2'-methyl biphenyl-4-ylamine $^1$H NMR (300 MHz, CDCl$_3$): δ 7.24-7.08 (m, 5H), 6.72 (d, J=7.2 Hz, 2H), 3.70 (bs, 2H), 2.27 (s, 3H):

Step 5: 4-[2-(3-Bromo-phenyl)-2-(4'-chloro-2'-methyl-biphenyl-4-ylcarbamoyl)-ethyl]-benzoic acid tert-butyl ester

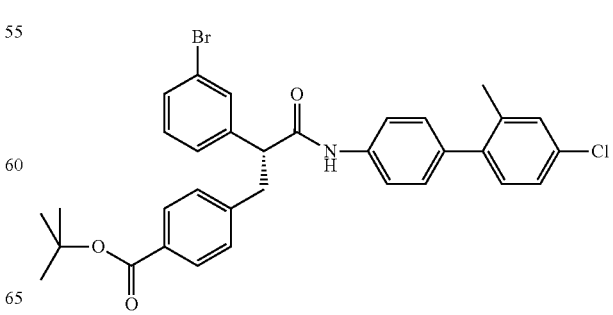

To a stirred suspension of 4-[2-carboxy-2-(3-bromo-phenyl)-ethyl]-benzoic acid tert-butyl ester (2.41 g, 5.94 mmol) in anhydrous CH$_2$Cl$_2$ (20 mL), was added oxalylchloride (1.0 mL, 11.8 mmol) at room temperature The reaction mixture was stirred for 14 h, concentrated under reduced pressure and azeotroped with CH$_2$Cl$_2$ (2×10 mL). The crude acid chloride (2.2 g, 1.61 mmol) was treated with 4-chloro-2-methyl biphenyl-4-ylamine (1.24 g, 5.71 mmol) and N,N-diisopropylethylamine (2.53 mL, 15.5 mmol) in CH$_2$Cl$_2$ (25 mL) at 0° C. The reaction mixture was stirred for 14 h at room temperature and concentrated under reduced pressure, The crude product was purified by column chromatography on silica gel, eluting with CH$_2$Cl$_2$-hexanes (30%-100%) to give 4-[2-(3-bromo-phenyl)-2-(4'-chloro-2'-methyl-biphenyl-4-ylcarbamoyl)-ethyl]-benzoic acid tert-butyl ester as a brownish solid (2.4 g, 88%)

$^1$H NMR (500 MHz, CDCl$_3$): δ 7.74 (d, J=14.0 Hz, 2H), 7.58-7.49 (m, 4H), 7.39-7.22 (m, 4H), 7.24-7.19 (m, 3H), 7.14 (d, J=14.0 Hz, 2H), 4.03 (t, J=11.0 Hz, 1H), 3.42 (dd, J=15.5, 22.5 Hz, 1H), 3.03 (dd, J=11.0, 22.5 Hz, 1H), 2.17 (s, 3H), 1.49 (s, 9H); Chiral HPLC conditions: Chiralcel OD-H T=23° C.; mobile phase=5-25% hexane/IPA; flow rate=1.0 mL/min; detection=254, 280, 220 nm retention time in min: 16.66 min (enantiomeric excess: 97.3%)

Step 6: 4-{2'-chloro-2'-methy l-biphenyl-4-ylcarbamoyl)-2-[(3-(4,4-dimethyl-cyclohex-1-enyl)-phenyl]-ethyl}-benzoic acid tert-butyl ester

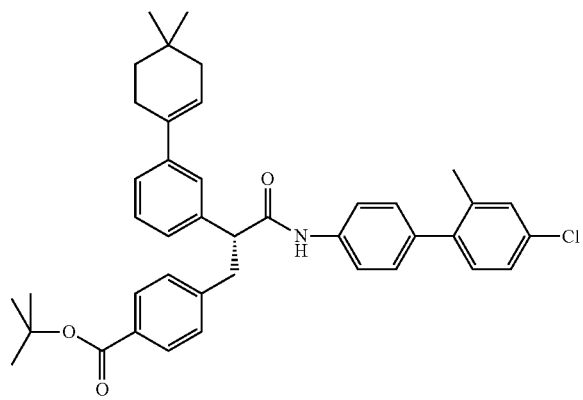 [SMILES: Cc1cc(Cl)ccc1-c1ccc(NC(=O)[C@H](Cc2ccc(C(=O)OC(C)(C)C)cc2)c2cccc(C3=CCC(C)(C)CC3)c2)cc1]

To 4-[2-(3-bromo-phenyl)-2-(4'-chloro-2'-methyl-biphenyl-4-ylcarbamoyl)-ethyl]-benzoic acid tert-butyl ester (1.2 g, 1.98 mmol) in DME (30 mL), was added 4,4-dimethyl-cyclo-hex-1-enyl-boronic acid (0.76 g, 4.96 mmol), PdCl$_2$(P(o-tolyl)$_3$)$_2$ (202 mg, 0.25 mmol), and diisopropylethylamine(1.0 mL, 5.94 mmol). The resulting mixture was heated at 85° C. for 2 h, allowed to cool to room temperature and filtered. Partitioned the filtrate between EtOAc (20 mL) and water. The organic phase was washed with brine, dried over sodium sulfate and concentrated under reduced pressure. The resulting crude was purified by column chromatography on silica gel, eluting with CH$_2$Cl$_2$:hexanes (20%-100%) to afford 4-{4'-chloro-2'-methyl-biphenyl-4-ylcarbamoyl)-2-[(3-(4,4-dimethyl-cyclohex-1-enyl)-phenyl]-ethyl}-benzoic acid tert-butyl ester as a yellow solid.

$^1$H NMR (500 MHz, CDCl$_3$): δ 10.14 (s, 1H), 7.76 (d, J=8.5 Hz, 2H), 7.57 (d, J=8.4 Hz, 2H), 7.48 (s, 1H), 7.35-7.20 (m, 9H), 7.13 (d, J=8.5 Hz, 1H), 6.06 (bt, 1H), 4.03 (t, J=6.5 Hz, 1H), 3.48 (dd, J=4.5, 13.5 Hz, 1H), 3.04 (dd, J=6.5, 14.0 Hz, 1H), 2.37-2.34 (m, 2H), 2.23 (t, J=7.0 Hz, 1H), 2.18 (s, 3H), 1.57 (t, J=6.5 Hz, 2H), 1.50 (s, 9H), 1.47 (t, J=6.5 Hz, 1H), 0.93 (s, 6H).

Step 7: 4-{2'-chloro-2'-methyl-biphenyl-4-ylcarbamoyl)-2-[(3-(4,4-dimethyl-cyclohex-1-enyl)-phenyl]-ethyl}-benzoic acid

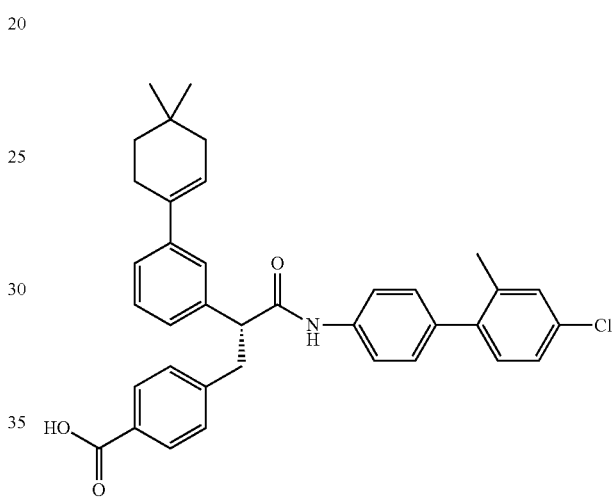

To a stirred solution of 4-{4'-chloro-2'-methyl-biphenyl-4-ylcarbamoyl)-2-[(3-(4,4-dimethyl-cyclohex-1-enyl)-phenyl]-ethyl}-benzoic acid tert-butyl ester (0.82 g, 1.29 mmol) in CH$_2$Cl$_2$ (30 mL) at room temperature, added trifluoroacetic acid (2.5 ml), and cont HCl (1.0 mL) The reaction mixture was stirred overnight. The organic solvents were removed under reduced pressure. The residue was extracted with ethyl acetate (2×100 mL), dried over MgSO$_4$ and concentrated o afford 4-{2'-chloro-2'-methyl-biphenyl-4-ylcarbamoyl)-2-[(3-(4,4-dimethyl-cyclohex-1-enyl)-phenyl]-ethyl}-benzoic acid as a solid.

$^1$H NMR (500 MHz, DMSO-d$_6$): 10.05 (s, 1H), 7.73 (d, J=8.0 Hz, 2H), 7.48 (d, J=8.5 Hz, 2H), 7.40 (s, 1H), 7.29-7.05 (m, 10H), 5.99 (s, 1H), 3.96 (t, J=10.5 Hz, 1H), 2.95 (dd, J=5.0, 14.0 Hz, 1H), 2.20-2.18 (m, 1H), 2.14 (t, J=7.5 Hz, 1H), 2.09 (s, 3H), 1.89 (bs, 2H), 1.49 (t, J=7.5 Hz, 1H), 1.39 (t, J=6.0 Hz, 2H), 0.84 (s, 6H).

Chiral HPLC conditions: Chiralcel OD-H T=23° C.; mobile phase=10-30% hexane/IPA; flow rate=1.0 mL/min; detection=254, 280, 220 nm retention time in min: 19.81 min (enantiomeric excess: 70.8%)

Step 8: 4-{2'-chloro-2'-methyl-biphenyl-4-ylcarbamoyl)-2-[(3-(4,4-dimethyl-cyclohexyl)-phenyl]-ethyl}-benzoic acid

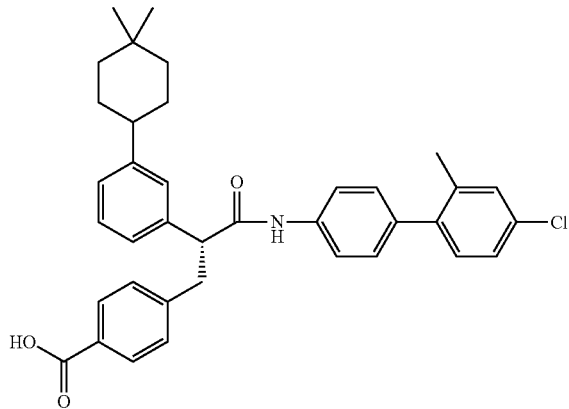 [SMILES: Cc1cc(Cl)ccc1-c1ccc(NC(=O)[C@H](Cc2ccc(C(=O)O)cc2)c2cccc(C3CCC(C)(C)CC3)c2)cc1]

A stirred solution of 4-{4'-chloro-2'-methyl-biphenyl-4-ylcarbamoyl)-2-[(3-(4,4-dimethyl-cyclohex-1-enyl)-phenyl]-ethyl}-benzoic acid (0.62 g, 1.07 mmol) in ethyl acetate (30 mL) at room temperature, was added Pd/C (100 mg). The mixture was stirred under 1 atm of $H_2$ (gas) at room temperature for 4 h. The catalyst was removed by filtration through a Celite plug and washed with ethyl acetate (2×50 mL). Concentration of the filtrate afforded 4-{2'-chloro-2'-methyl-biphenyl-4-ylcarbamoyl)-2-[(3-(4,4-dimethyl-cyclohex-1-enyl)-phenyl]-ethyl}-benzoic acid as a solid.

$^1$H NMR (300 MHz, DMSO-$d_6$): 12.69 (s, 1H), 10.06 (s, 1H), 7.72 (d, J=7.0 Hz, 2H), 7.49 (d, J=7.0 Hz, 2H), 7.27-7.03 (m, 11H), 3.94 (t, J=5.5 Hz, 1H), 3.39 (t, J=11.5 Hz, 1H), 2.93 (dd, J=5.5, 13.0 Hz, 1H), 2.16 (t, J=7.0 Hz, 1H), 2.09 (s, 3H), 1.48-1.43 (m, 4H), 1.24-1.19 (m, 2H), 0.87 (s, 3H), 0.84 (s, 3H).

Step 9: Sodium-2-(4-{2-(4'-chloro-2'-methyl biphenyl-4-ylcarbamoyl)-2-[3-(4,4-dimethyl-cyclohexyl)-phenyl]-ethyl}-benzoylamino-ethane sulfonic acid

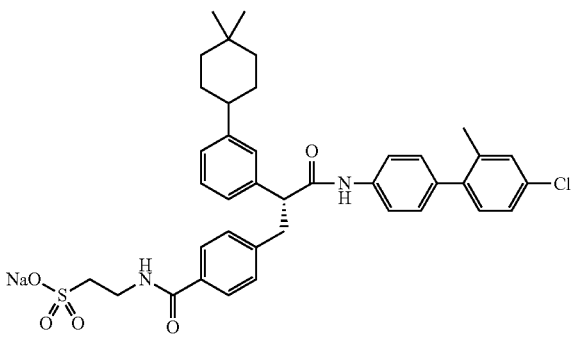

To a mixture of 4-{2'-chloro-2'-methyl-biphenyl-4-ylcarbamoyl)-2-[(3-(4,4-dimethyl-cyclohex-1-enyl)-phenyl]-ethyl}-benzoic acid (0.6 g, 1.03 mmol) and EDCI (290 mg, 1.55 mmol) in DMF (7 mL), added HOBt (230 mg, 1.55 mmol), N,N-diisopropylethylamine (0.4 g, 2.06 mmol), and taurine (250 mg, 0.5 mmol). The resulting mixture was stirred for 14 h. The reaction solvent was removed under reduced pressure. The residue mixture was dissolved in 0.1 N NaHCO$_3$ and acetonitrile, purified by column chromatography on a C-18 silica gel flash chromatography column, eluting with an acetonitrile-water gradient. Sodium-2-(4-{2-(4'-chloro-2'-methyl-biphenyl-4-ylcarbamoyl)-2-[3-(4,4-dimethylcyclohex-1-enyl)-phenyl]-ethyl}-benzoylamino-ethane sulfonic acid was obtained as a white solid.

$^1$H NMR (500 MHz, DMSO-$d_6$): 9.98 (s, 1H), 8.25 (bs, 1H), 7.50 (d, J=3.0 Hz, 2H), 7.43 (d, J=5.5 Hz, 2H), 7.19-6.98 (m, 11H), 3.85 (bs, 1H), 3.32-3.18 (m, 3H), 2.83 (d, J=14.0 Hz, 2H), 2.47 (bs, 2H), 2.23 (bs, 1H), 2.03 (s, 3H), 1.42-1.15 (m, 6H), 0.81 (s, 3H), 0.78 (s, 3H); LC-MS m/z=685 [C$_{39}$H$_{42}$N$_2$O$_5$S]$^+$; Anal Calcd: (MF: C$_{398}$H$_{42}$N$_2$O$_5$SNa+3.3H$_2$O) Calcd: C:60.94, H:6.37, N:3.64 Found: C:60.82, H:6.08, N:3.57.

Chiral HPLC conditions: Regis-Whelk-01-786615, (S, S) 10/100 250×10 mm T=23° C.; mobile phase=100% ACN/ (5% NH$_4$CO$_3$, +H$_2$O) flow rate=1.0 mL/min; detection=254 nm retention time in min: 12.39 min (enantiomeric excess: 95.1%)

Example 3: Ammonium, 2-(S)-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate Step 1: [4-(4-tert-Butyl-cyclohex-1-enyl)-phenyl]-acetic acid ethyl ester

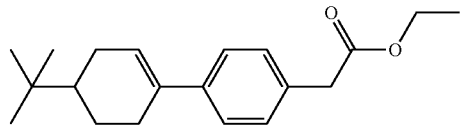 [SMILES: CCOC(=O)Cc1ccc(C2=CCC(C(C)(C)C)CC2)cc1]

To a mixture of 4-bromophenyl ethyl acetate (780 mg), 4-t-butyl-cyclohexen-1-yl boronic acid (897 mg), PdCl$_2$(P(o-tolyl)$_3$)$_2$(254 mg) in THF: ethanol: water (8 mL: 4 mL: 2 mL), added sodium carbonate (1.377 g). The sealed flask was heated at 140° C. for a 5 min period. The heterogeneous mixture was treated with an excess of 1M aqueous hydrochloric acid and filtered through a celite pad. The organic solvents were removed under reduced pressure and the residue partitioned between ethyl acetate and water. The organic phase was washed with water and saturated aqueous sodium chloride, dried over magnesium sulfate and chromatographed on silica gel using an ethyl acetate/hexanes gradient. The product was obtained as a yellow oil.

$^1$H NMR (500 MHz, CDCl$_3$): 7.32 (d. J=8 Hz, 2H), 7.20 (d, J=8 Hz, 2H), 6.10 (m, 1H), 4.12 (q, J=7 Hz, 2H), 3.57 (s, 2H), 2.52-2.32 (m, 2H), 2.26-2.18 (m, 1H), 2-1.9 (m, 2H), 1.38-1.2 (m, 5H), 0.91 (s, 9H).

Step 2: [4-((1R,2R,4S)-4-tert-Butyl-1,2-dihydroxycyclohexyl)-phenyl]-acetic acid ethyl ester and [4-((1R,2R,4R)-4-tert-Butyl-1,2-dihydroxy-cyclohexyl)-phenyl]-acetic acid ethyl ester

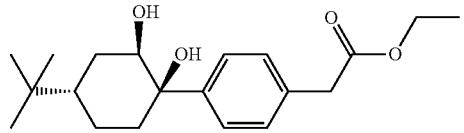

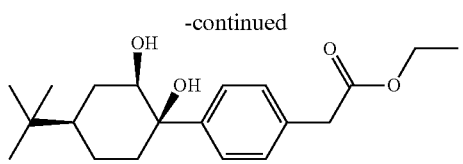

A mixture of AD-mix-beta (6.512 g, J. Org. Chem 57, 2768 (1992)) and methanesulfonamide (443 mg, 4.66 mmol) in tert-butanol (23 mL) and water (28 mL) was cooled to 2-4° C. To this mixture, [4-(4-tert-Butyl-cyclohex-1-enyl)-phenyl]-acetic acid ethyl ester (1.4 g, 4.66 mmol) in tert-Butanol (5 mL) was added slowly while making sure that the temperature remained in the 2-4° C. range. The mixture was stirred at the same temperature for a period of 4 days then quenched by adding sodium sulfite (1.5 g/mmol starting material) in water (20 mL). After allowing to warm to room temperature, the reaction mixture was stirred an additional 1 h before being partitioned between ethyl acetate and water. The organic phase was washed with brine then concentrated under reduced pressure to afford crude material which was purified by chromatography on silica gel, eluting with an ethyl acetate/hexanes gradient. Two products were obtained. In agreement with the report from Hamon et al (Tetrahedron 57, 9499 (2001)) they were assigned as follows:

First eluting product: [4-((1R,2R,4R)-4-tert-Butyl-1,2-dihydroxy-cyclohexyl)-phenyl]-acetic acid ethyl ester $^1$H NMR (500 MHz, CDCl$_3$): 7.46 (m, 2H), 7.28 (m, 2H), 4.16 (q, J=7 Hz, 2H), 3.99 (m, 1H), 3.61 (s, 2H), 2.59 (m, 1H), 1.92 (m, 2H), 1.64-1.46 (m, 5H), 1.27 (t, J=7 Hz, 3H), 0.93 (s, 9H).

Second eluting product: [4-((1R,2R,4S)-4-tert-Butyl-1,2-dihydroxy-cyclohexyl)-phenyl]-acetic acid ethyl ester $^1$H NMR (500 MHz, CDCl$_3$): 7.51 (m, 2H), 7.30 (m, 2H), 4.36 (m, 1H), 4.16 (q, J=7 Hz, 2H), 3.62 (s, 2H), 2.74 (m, 1H), 2.26 (m, 1H), 2.20 (m, 1H), 2.07 (m, 1H), 1.92 (m, 1H), 1.75 (m, 1H), 1.27 (t, J=7 Hz, 3H), 1.17 (m, 2H), 0.80 (s, 9H).

Step 3: [4-(3R,6R,7R)-6-tert-Butyl-2-thioxo-tetrahydro-benzo[1,3]dioxol-3-yl)-phenyl]-acetic acid ethyl ester

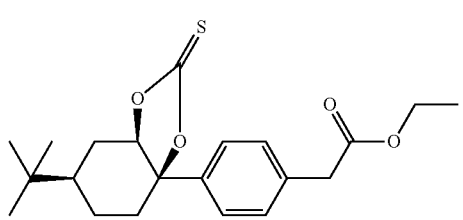 [SMILES: CCOC(=O)Cc1ccc([C@]23CC[C@@H](C(C)(C)C)C[C@H]2OC(=S)O3)cc1]

A solution of [4-((R,2R,4R)-4-tert-Butyl-1,2-dihydroxy-cyclohexyl)-phenyl]-acetic acid ethyl ester (319 mg, 0.95 mmol) and thiocarbonyl diimidazole (309 mg, 1.91 mmol) in THF (15 mL) was refluxed under N$_2$ overnight. The reaction mixture was partitioned between ethyl acetate and brine, dried over Na$_2$SO$_4$ and concentrated under reduced pressure. Purification of the residue by chromatography on silica gel using an ethyl acetate/hexanes gradient afforded 297 mg of product.

$^1$H NMR (500 MHz, CDCl$_3$) 7.31 (m, 4H), 4.97 (dd, J=9 Hz, J=7 Hz, 1H), 4.13 (q, J=7 Hz, 2H), 3.59 (s, 2H), 2.53-2.48 (m, 1H), 2.40-2.31 (m, 1H), 1.90-1.72 (m, 2H), 1.40-1.15 (m, 6H), 0.91 (s, 9H).

Step 4: [4-((R)-4-tert-Butyl-cyclohex-1-enyl)-phenyl]-acetic acid ethyl ester

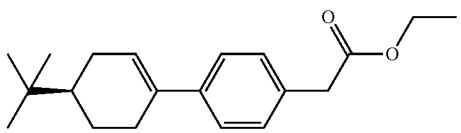 [SMILES: CCOC(=O)Cc1ccc(C2=CC[C@H](C(C)(C)C)CC2)cc1]

A solution of [4-((3aR,6S,7aR)-6-tert-Butyl-2-thioxo-tetrahydro-benzo[1,3]dioxol-3a-yl)-phenyl]-acetic acid ethyl ester (297 mg, 0.80 mmol) in triethylphosphite (3 mL) was slowly added to a solution of triethylphosphite (10 mL) heated to reflux-rate of addition was such that the reaction temperature exceeded 150° C. After refluxing overnight, the solvent was removed under vacuum and the crude reaction mixture was loaded on top of a silica column and eluted with an ethyl acetate/hexanes gradient to afford 145 mg of the title compound.

$^1$H NMR (500 MHz, CDCl$_3$): 7.32 (d, J=8 Hz, 2H), 7.20 (d, J=8 Hz, 2H), 6.10 (m, 1H), 4.12 (q, J=7 Hz, 2H), 3.57 (s, 2H), 2.52-2.32 (m, 2H), 2.26-2.18 (m, 1H), 2-1.9 (m, 2H), 1.38-1.2 (m, 5H), 0.91 (s, 9H).

Determination of the enantiomeric excess: A sample of the product was treated with an excess of aqueous 1M NaOH:ethanol:water (1:2:3 ratio by volume) and heated at 125° C. for a 5 min period. The organic solvents were removed under reduced pressure and the residue was partitioned between ethyl acetate and 1M aqueous HCl. The organic phase was washed with water and a saturated sodium chloride solution and then dried over magnesium sulfate. The enantiomeric excess of the product was determined to be >99% by chiral HPLC utilizing a Chiral Technologies ChiralPak AD-H 250 mm×4.6 mm column, eluting at a 1.0 mL/min flow rate using a mixture of hexanes:isopropanol, methane sulfonic acid in a 95:5:0.1 ratio. The sample was dissolved at 1 mg/mL in ethanol prior to injection. The retention time observed was 6.2 min.

Step 5: 4-{2-[4-(4-(R)-tert-Butylcyclohex-1-enyl)-phenyl]-2-ethoxylcarbonyl-ethyl}-benzoic acid tert-butyl ester

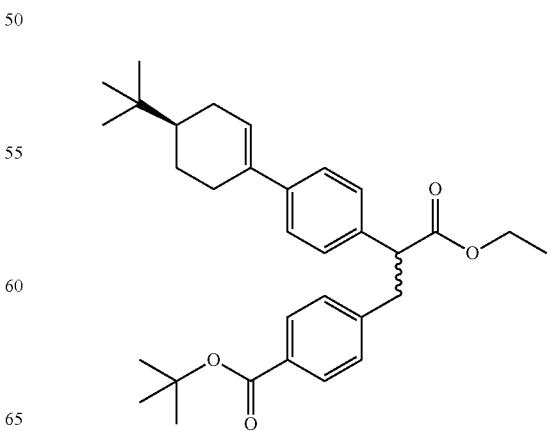

To [4-((R)-4-tert-Butyl-cyclohex-1-enyl)-phenyl]-acetic acid ethyl ester (95 mg, 0.32 mmol) in anhydrous THF (5 mL), chilled to −78° C., was added 380 uL (0.38 mmol) of 1M lithium hexamethyldisilazane in THF. The resulting solution was stirred for 1 hr before 4-Bromomethylbenzoic acid tert-butyl ester (94 mg, 0.35 mmol) was added. The reaction mixture was allowed to warm to rt overnight then quenched with saturated NH₄Cl solution. After partitioning between ethyl acetate and brine the organic portion was dried over Na₂SO₄ and concentrated under reduced pressure. Purification of the crude by prep TLC (Analtech, 2 mm silica plates) using an hexane/ethyl acetate (10:1) gave 63 mg of product.

$^1$H NMR (500 MHz, CDCl₃): 7.83 (d, J=8.5 Hz, 2H), 7.31 (d, J=8.5 Hz, 2H), 7.20 (d, J=8 Hz, 2H), 7.14 (d, J=8 Hz, 2H), 6.12 (m, 1H), 4.03 (q, J=7 Hz 2H), 3.80 (t, J=8.5 Hz, 1H), 3.41 (dd, J=14, 8.5 Hz 1H). 3.03 (dd, J=14, 7 Hz, 1H), 2.56-2.4 (m, 2H) 2.35-2.2 (m, 1H), 2.05-1.9 (m, 2H), 1.56 (s, 9H), 1.36-1.2 (m, 2H), 1.11 (t, J=7 Hz, 3H), 0.89 (s, 9H).

Step 6: 4-{2-[4-(4-(R)-tert-Butylcyclohex-1-enyl)-phenyl]-2-carboxy-ethyl}-benzoic acid tert-butyl ester

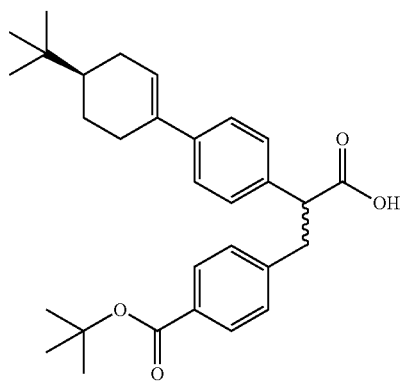 [SMILES: CC(C)(C)OC(=O)c1ccc(CC(C(=O)O)c2ccc(C3=CC[C@H](C(C)(C)C)CC3)cc2)cc1]

To 4-{2-[4-(4-(R)-tert-Butylcyclohex-1-enyl)-phenyl]-2-ethoxylcarbonyl-ethyl}-benzoic acid tert-butyl ester (63 mg, 0.13 mmol) dissolved in a solution of THF (3 mL), MeOH (1 mL) and water (1 mL) was added lithium hydroxide (27 mg, 0.64 mmol). The solution was stirred at rt for 5 hrs then neutralized with 3M KH₂PO₄ and extracted with ethyl acetate. The organic portion was washed with brine, dried over Na₂SO₄ and concentrated under vacuum to afford crude material which was used without further purification.

Step 7: 4-{2-[4-(4-(R)-tert-Butylcyclohex-1-enyl)-phenyl]-2-(4'-chloro-2'-methylbiphenyl-4-ylcarbamoyl)-ethyl]-benzoic acid tert-butyl ester

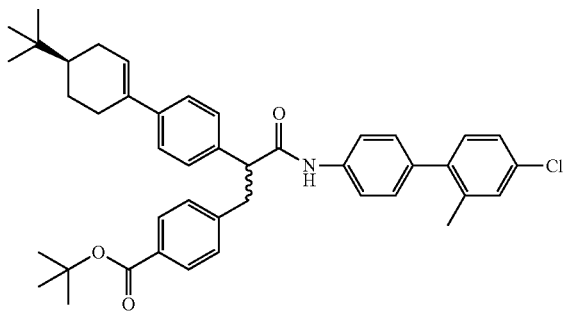 [SMILES: Cc1cc(Cl)ccc1-c1ccc(NC(=O)C(Cc2ccc(C(=O)OC(C)(C)C)cc2)c2ccc(C3=CC[C@H](C(C)(C)C)CC3)cc2)cc1]

To 4-{2-[4-(4-(R)-tert-Butylcyclohex-1-enyl)-phenyl]-2-carboxy-ethyl}-benzoic acid tert-butyl ester (697 mg, 1.51 mmol) in anhydrous dichloromethane (30 mL) was added oxalyl chloride (650 uL, 7.53 mmol) and 3 drops of DMF. The resulting solution was stirred at rt for 1 hr before being concentrated under vacuum. The residue was co-evaporated with toluene (1×5 mL) then dissolved in toluene again (20 mL). To the mixture was added 4-chloro-2-methylbiphenyl-4-ylamine (361 mg, 1.66 mmol) and DIPEA (1.3 mL, 7.53 mmol). The resulting mixture was refluxed for 90 min, diluted with ethyl acetate and washed with saturated NaHCO₃. The organic portion was dried over Na₂SO₄ and concentrated under vacuum to afford crude material which was crystallized from MeOH to afford a white solid (590 mg). Removing the solvent and purification of the residue by chromatography on silica gel using an ethyl acetate/hexanes gradient afforded an additional 137 mg of product.

$^1$H NMR (500 MHz, DMSO-d₆): 10.16 (s, 1H), 7.78 (d, J=8 Hz, 2H), 7.59 (d, J=8.5 Hz, 2H), 7.4-7.32 (m, 7H), 7.21 (d, J=8 Hz, 2H), 7.15 (d, J=8 Hz, 2H), 6.14 (m, 1H), 4.03 (dd, J=9, 7 Hz, 1H), 3.48 (dd, J=13.5, 9.5 Hz, 1H), 3.41 (dd, J=13.5, 6.5 Hz, 1H), 2.4-2.3 (m, 1H), 2.2-2.15 (m, 4H), 1.96-1.9 (m, 2H), 1.52 (s, 9H), 1.32-1.2 (m, 2H), 0.89 (s, 9H).

Step 8: 4-{2-[4-(4-(R)-tert-Butylcyclohex-1-enyl)-phenyl]-2-(4'-chloro-2'-methylbiphenyl-4-ylcarbamoyl)-ethyl}-benzoic acid

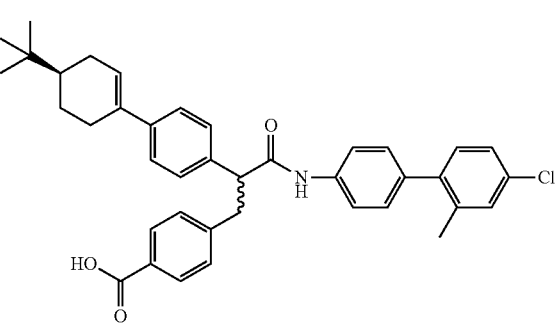 [SMILES: Cc1cc(Cl)ccc1-c1ccc(NC(=O)C(Cc2ccc(C(=O)O)cc2)c2ccc(C3=CC[C@H](C(C)(C)C)CC3)cc2)cc1]

To 4-{2-[4-(4-(R)-tert-Butylcyclohex-1-enyl)-phenyl]-2-(4'-chloro-2'-methylbiphenyl-4-ylcarbamoyl)-ethyl]-benzoic acid tert-butyl ester (727 mg, 1.1 mmol) was added 4N HCl/dioxane (30 mL), water (5 mL) and conc. HCl (1 mL).

The resulting solution was stirred at rt overnight. The excess solvent was removed under vacuum and the residue co-evaporated with toluene to afford the desired crude product as a gummy oil. The crude material was used the next step without further purification.

Step 9: Sodium, 2-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate

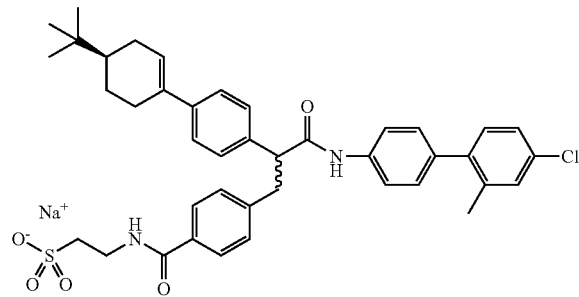 [SMILES: Cc1cc(Cl)ccc1-c1ccc(NC(=O)C(Cc2ccc(C(=O)NCCS(=O)(=O)[O-])cc2)c2ccc(C3=CC[C@H](C(C)(C)C)CC3)cc2)cc1 ; [Na+]]

To crude 4-{2-[4-(4-(R)-tert-Butylcyclohex-1-enyl)-phenyl]-2-(4'-chloro-2'-methyl biphenyl-4-ylcarbamoyl)-ethyl]-benzoic acid (assumed 1.1 mmol) in DMF (25 mL) was added EDC (316 mg, 1.65 mmol), HOBt (252 mg, 1.65 mmol), taurine (206 mg, 1.65 mmol) and DIPEA (550 uL, 3.29 mmol). The resulting mixture was stirred at rt overnight. The excess solvent was removed under vacuum and to the oily residue was added excess 1N HCl. After decanting off the excess 1N HCl, the residue was dissolved in acetonitrile/MeOH, made basic with saturated NaHCO$_3$ and purified using reverse phase flash chromatography and eluting with an acetonitrile/water gradient. The sodium salt was obtained as a white solid LCMS: 711.6 [M-H]$^-$ Step 10: Ammonium, 2-(S)-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate

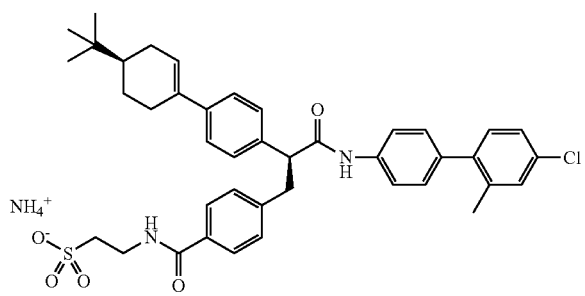 [SMILES: [NH4+] ; Cc1cc(Cl)ccc1-c1ccc(NC(=O)[C@@H](Cc2ccc(C(=O)NCCS(=O)(=O)[O-])cc2)c2ccc(C3=CC[C@H](C(C)(C)C)CC3)cc2)cc1]

Sodium, 2-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate (obtained on Step 8 above), was dissolved in DMF, The product was subjected to preparative HPLC on a Pirkle Covalent (S,S)-Whelk-01 column (250 mm×10 mm), eluting at 10 mL/min with a gradient of acetonitrile and 5 mM ammonium bicarbonate. The title compound was the first of the two diastereopmers to elute.

Conditions for the determination of the enantiomeric excess by HPLC: Regis-Whelk-01-786615, (S, S) 10/100 250×10 mm T=23° C.; mobile phase=100% ACN/(5% Phosphate pH=7.0, ACN) flow rate=1.0 mL/min; detection=254 nm. Retention time in min: 18.22 min (enantiomeric excess: 99.1%)

$^1$H NMR (500 MHz, CD$_3$OD): 7.71 (d, J=8.5 Hz, 2H), 7.51 (d, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H),

Example 4: Ammonium, 2-(R)-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate

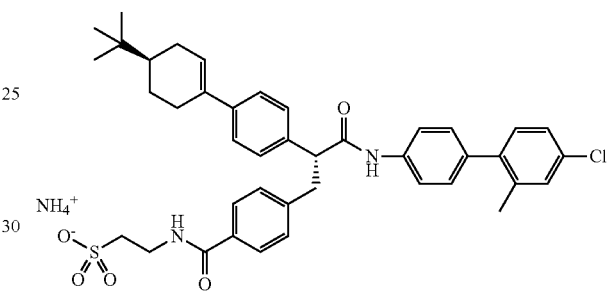

The title compound was the second compound eluting from the chiral chromatography reported in Example 3, Step 9.

Conditions for the determination of the enantiomeric excess by HPLC: Regis-Whelk-01-786615, (S, S) 10/100 250×10 mm T=23° C.; mobile phase=100% ACN/(5% Phosphate pH=7.0, ACN) flow rate=1.0 mL/min; detection=254 nm. Retention time in min: 23.55 min (enantiomeric excess: 99.5%)

$^1$H NMR (500 MHz, CD$_3$OD): 7.71 (d, J=8.5 Hz, 2H), 7.51 (d, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H).

Example 5: Ammonium, 2-(S)-{4-[2-[4-(4-(S)-tert-butylcyclohex-1-enyl)-phenyl]-2-(4'-chloro-2'-methylbiphenyl-4-ylcarbamoyl)-ethyl]-benzoylamino}-ethanesulfonate Step 1: [4-((S)-4-tert-Butyl-cyclohex-1-enyl)-phenyl]-acetic acid ethyl ester

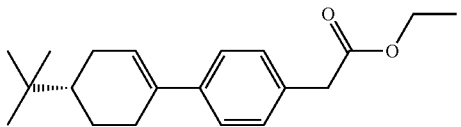

Utilizing the second eluting diol in Example 3, Step 2, the chiral alkene shown above was obtained after utilizing the methods described in Example 3, Steps 3 and 4

$^1$H NMR (500 MHz, CDCl$_3$): 7.32 (d, J=8 Hz, 2H), 7.20 (d, J=8 Hz, 2H), 6.10 (m, 1H), 4.12 (q, J=7 Hz, 2H), 3.57 (s, 2H), 2.52-2.32 (m, 2H), 2.26-2.18 (m, 1H), 2-1.9 (m, 2H), 1.38-1.2 (m, 5H). 0.91 (s, 9H).

Determination of the enantiomeric excess: A sample of the product was treated with an excess of aqueous 1M NaOH:ethanol water (1:2:3 ratio by volume) and heated at 125° C. for a 5 min period. The organic solvents were removed under reduced pressure and the residue was partitioned between ethyl acetate and 1M aqueous HCl. The organic phase was washed with water and a saturated sodium chloride solution and then dried over magnesium sulfate. The enantiomeric excess of the product was determined to be >99% by chiral HPLC utilizing a Chiral Technologies ChiralPak AD-H 250 mm×4.6 mm column, eluting at a 1.0 mL/min flow rate using a mixture of hexanes:isopropanol:methane sulfonic acid in a 95:5:0.1 ratio. The sample was dissolved at 1 mg/mL in ethanol prior to injection. The retention time observed was 5.6 min.

Step 2: Ammonium, 2-(S)-{4-[2-[4-(4-(S)-tert-butylcyclohex-1-enyl)-phenyl]-2-(4'-chloro-2'-methyl-biphenyl-4-ylcarbamoyl)-ethyl]-benzoylamino}-ethanesulfonate

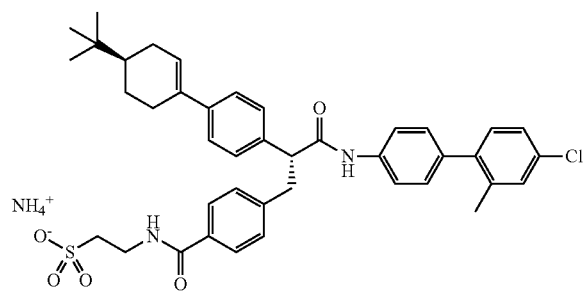 [SMILES: [NH4+] ; Cc1cc(Cl)ccc1-c1ccc(NC(=O)[C@H](Cc2ccc(C(=O)NCCS(=O)(=O)[O-])cc2)c2ccc(C3=CC[C@H](C(C)(C)C)CC3)cc2)cc1]

[4-((S)-4-tert-Butyl-cyclohex-1-enyl)-phenyl]-acetic acid ethyl ester (Step 1, above), was utilized to yield the title compound through the sequence illustrated in Example 3, Steps 5-10. The title compound eluted first among the two possible diastereomers after preparative HPLC on a Pirkle Covalent (S, S)-Whelk-01 column (250×10 mm), eluting at 10 mL/min with a gradient of acetonitrile and 5 mM ammonium bicarbonate.

Conditions for the Determination of the Enantiomeric Excess by HPLC:

The sample was diluted in ethanol at a 1 mg/mL concentration. It was injected into an HPLC system equipped with a Regis-Whelk-01-786615, (S, S) 10/100 250×10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in milt 18.23 min (enantiomeric excess: >99.5%)

$^1$H NMR (500 MHz, CD$_3$OD): 7.71 (d, J=8.5 Hz, 2H), 7.51 (d, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H).

Example 6: Ammonium, 2-(R)-{4-[2-[4-(4-(R)-tert-butylcyclohex-1-enyl)-phenyl]-2-(4'-chloro-2-methylbiphenyl-4-ylcarbamoyl)-ethyl]-benzoylamino}-ethanesulfonate

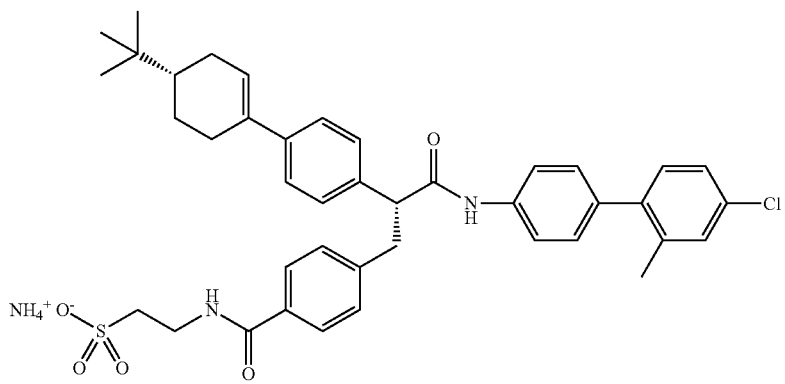

The title compound was the second compound eluting from the chiral chromatography reported in Example 5, Step 2.

The sample was diluted in ethanol at a 1 mg/mL concentration. It was injected into an HPLC system equipped with a Regis-Whelk-01-786615, (S, S)10/100 250×10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in min:23.41 min (enantiomeric excess: >99.5%)

$^1$H NMR (500 MHz, CDOD): 7.71 (d, J=8.5 Hz, 2H), 7.51 (d, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H).

Using the methods described in Examples 1-6, the following compounds were synthesized.

Example 7: Sodium-2-(R)-4-[2-(4'-chloro-2'-methyl-biphenyl-4-ylcarbamoyl)-2-[(4-(3,3-dimethyl-but-1-enyl)-phenyl]-ethyl}-benzoyl amino ethane sulfonic acid

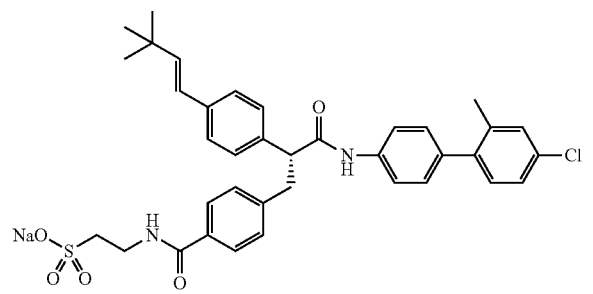

$^1$H NMR (500 MHz, DMSO-d$_6$): 10.14 (s, 1H), 8.39 (t, J=9.8 Hz, 1H), 7.61 (d, J=8.7 Hz, 2H), 7.55 (d, J=8.7 Hz, 2H), 7.33-7.12 (m, 11H), 6.25 (dd, J=16.2, 3.6 Hz, 2H), 3.98 (t. J=8.4 Hz, 1H), 3.49-3.38 (m, 3H), 3.0 (dd, J=6.3, 7.8 Hz, 1H), 2.61 (t, J=7.8 Hz, 2H), 2.17 (s, 3H) 1.06 (s, 3H) LC-MS m/z=657 [C$_{37}$H$_{38}$N$_2$O$_5$SClNa+H]$^+$; HPLC conditions: Waters Atlantis C-18 OBD 4.6×150 mm; mobile phase=ACN/(H$_2$O:0.1 TFA) flow rate=1.0 mL/min; detection=UV@254, 220 nm retention time in min: 12.33; Anal Calcd: (MF: C$_{37}$H$_{38}$N$_2$O$_5$SClNa+1.2H$_2$O) Calcd: C: 63.23, H: 5.79, N: 3.99 Found: C: 63.02, H: 5.89, N: 4.15. Chiral HPLC Conditions:

The sample was diluted in ethanol at a 1 mg/mL concentration. It was injected into an HPLC system equipped with a Regis-Whelk-01-786615, (S, S) 10/100 250×10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in min: 14.08 min (enantiomeric excess: >97.06%)

Example 8: Sodium-2-(S)-4-[2-(4'-chloro-2'-methyl-biphenyl-4-ylcarbamoyl)-2-[(4-(3,3-dimethyl-but-1-enyl)-phenyl]-ethyl}-benzoyl amino ethane sulfonic acid

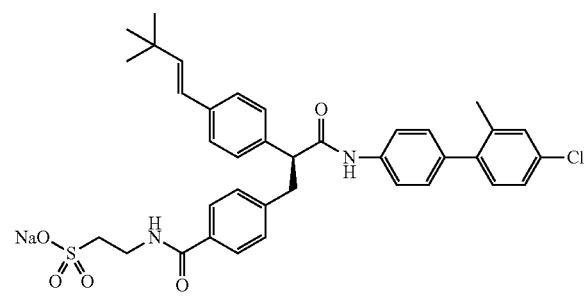

$^1$H NMR (500 MHz, DMSO-d$_6$): 10.14 (s, 1H), 8.39 (t, J=9.8 Hz, 1H), 7.61 (d, J=8.7 Hz, 2H), 7.56 (d, J=6.6 Hz, 2H), 7.33-7.12 (m, 11H), 6.26 (dd, J=16.2, 3.6 Hz, 2H), 3.98 (t, J=9.9 Hz, 1H), 3.49-3.39 (m, 3H), 3.0 (dd, J=6.3, 7.8 Hz, 1H), 2.61 (t, J=7.2 Hz, 2H.), 2.17 (s, 3H), 1.05 (s, 3H); LC-MS m/z=657 [C$_{37}$H$_{38}$N$_2$O$_5$SClNa+H]$^+$; HPLC conditions: Waters Atlantis C-18 OBD 4.6×150 mm; mobile phase=ACN/(H$_2$O: 0.1 TFA) flow rate=1.0 mL/min; detection=UV@254, 220 nm retention time in min: 12.33; Anal Calcd: (MF: C$_{37}$H$_{38}$N$_2$O$_5$SClNa+1.5H$_2$O) Calcd: C: 62.75, H: 5.83, N:3.916 Found: C: 62.65, H:5.81, N:4,13. Chiral HPLC Conditions:

The sample was diluted in ethanol at a 1 mg/mL concentration. It was injected into an HPLC system equipped with a Regis-Whelk-01-786615, (S, S) 10/100 250×10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in min; 17.69 min (enantiomeric excess: >97.4%)

Example 9: 2-(4-{(R)-2-(4'-Chloro-2'-methyl-biphenyl-4-ylcarbamoyl)-2-[4-(4,4-dimethyl-cyclohex-1-enyl)-phenyl]-ethyl}-benzoylamino)-ethanesulfonic acid

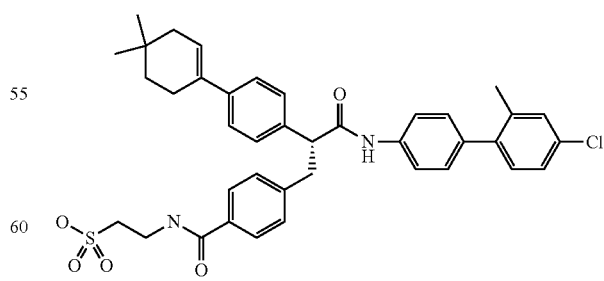

$^1$H NMR (500 MHz, DMSO-d$_6$): δ 10.14 (s, 1H), 8.40 (t, J=2.8 Hz, 1H), 7.64 (d, J=8.4 Hz, 2H), 7.57 (d, J=8.9 Hz, 2H), 7.37-7.14 (m, 11H), 6.07 (bs, 1H), 4.0 (t, J=5.5 Hz, 1H), 3.47-3.45 (m, 3H), 3.0-2.85 (m, 1H), 2.62 (t, J=4.2 Hz,

2H), 2.35 (t, J=1.2 Hz, 2H), 2.18 (s, 3H), 1.95 (t, J=2.8 Hz, 2H), 1.46 (t, J=2.8 Hz, 2H), 0.91 (s, 6H). LC-MS m/z=685 $[C_{39}H_{40}N_2O_4SCl+H]^+$;

Chiral HPLC Conditions:

The sample was diluted in ethanol at a 1 mL concentration. It was injected into an HPLC system equipped with a Regis-Whelk-01-786615, (S, S) 10/100 250×10 mm column kept at 23° C.

The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 17.92 min (enantiomeric excess: 99.5%)

Example 10: 2-(4-{((S)-2-(4'-Chloro-2'-methyl-biphenyl-4-ylcarbamoyl)-2-[4-(4,4-dimethyl-cyclohex-1-enyl)-phenyl]-ethyl}-benzoylamino)-ethanesulfonic acid

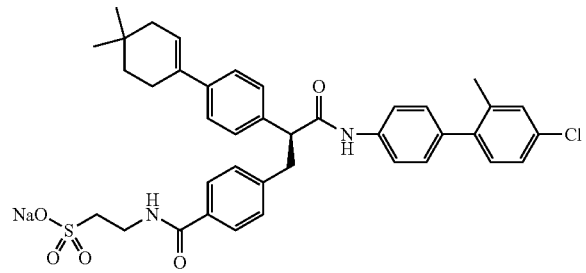

$^1$H NMR (500 MHz, DMSO-$d_6$): δ 10.15 (s, 1H), 8.40 (t, J=2.8 Hz, 1H), 7.64 (d, J=8.4 Hz, 2H), 7.57 (d, J=8.9 Hz, 2H), 7.37-7.11 (m, 11H), 6.07 (bs, 1H), 4.0 (t, J=5.5 Hz, 1H), 3.47-3.45 (m, 3), 3.0-2.85 (m, 1H). 2.62 (t, J=8.4 Hz, 2), 2.35 (t, J=1.2 Hz, 2H), 2.18 (s, 3H), 1.95 (t, J=2.8 Hz, 2H), 1.46 (t, J=2.8 Hz, 2H), 0.91 (s, 6H). LC-MS m/z=684 $[C_{39}H_{40}N_2O_4SCl]^+$

Chiral HPLC conditions: The sample was diluted in ethanol at a 1 mg/mL concentration. It was injected into an HPLC system equipped with a Regis Whelk 01-786615, (S, S) 10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 13.87 min (enantiomeric excess: 97.6%)

Example 11: Sodium-2-[4-(S)-2-(4'-tert-butyl-biphenyl-4-yl)-2-(4'-chloromethyl-phenyl-carbamoyl)-ethyl}-benzoylamino-ethane sulfonic acid

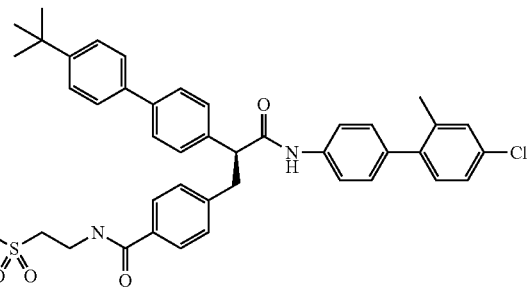

$^1$H NMR (500 MHz, DMSO-$d_6$): δ 7.70 (d, J=6.0 Hz, 2H), 7.57-7.47 (m, 11H), 7.33 (d, J=8.4 Hz, 2H), 7.21-7.13 (m, 4H), 4.0 (t, J=6.0 Hz, 1H), 3.74 (t, J=13.5 Hz, 2H), 3.53 (dd, J=6.3, 3.0 Hz, 1H), 3.15 (dd, J=6.6, 2.8 Hz, 1H), 3.06 (t, J=6.9 Hz, 2H), 2.20 (s, 3H), 1.34 (s, 9H). LC-MS m/z=709 $[C_{35}H_{36}N_2O_5SClNa]^+$;

Chiral HPLC conditions: The sample was diluted in ethanol at a 1 mg/mL concentration. It was injected into an HPLC system equipped with a Regis-Whelk-01-786615, (S, S) 10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 23.87 min (enantiomeric excess: 99.5%)

Example 12: Sodium-2-[4-(R)-2-(4'-tert-butyl-biphenyl-4-yl)-2-(4'-chloro-2'-methyl-phenyl-carbamoyl)-ethyl}-benzoylamino-ethane sulfonic acid

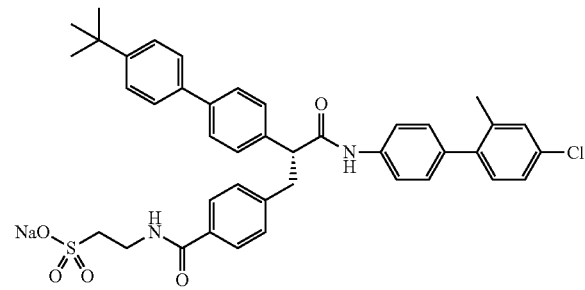

$^1$H NMR (500 MHz, DMSO-$d_6$) δ 7.70 (d, J=6.0 Hz, 2H), 7.57-7.47 (m, 11H), 7.33 (d, J=8.4 Hz, 2H), 7.21-7.13 (m, 4H), 4.0 (t, J=6.0 Hz, 1H), 3.74 (t, J=13.5 Hz, 2H), 3.53 (cid, J=6.3, 3.0 Hz, 1H), 3.15 (dd, J=6.6, 2.8 Hz, 1H), 3.06 (t, J=6.9 Hz, 2H), 2.20 (s, 3H), 1.34 (s, 9H). LC-MS m/z=707 $[C_{35}H_{36}N_2O_5SClNa-2]^+$;

Chiral HPLC conditions: The sample was diluted in ethanol at a 1 mg/mL concentration. It was injected into an HPLC system equipped with a Regis-Whelk-01-786615, (S, S) 10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 23.86 min (enantiomeric excess: >96.9%).

Example 13: Sodium-2-[4-(R)-2-(4'-tert-butyl-biphenyl-4-yl)-2-(2',4',6'-trimethyl-biphenyl-4-ylcarbamoyl)-ethyl}-benzoylamino-ethane sulfonic acid

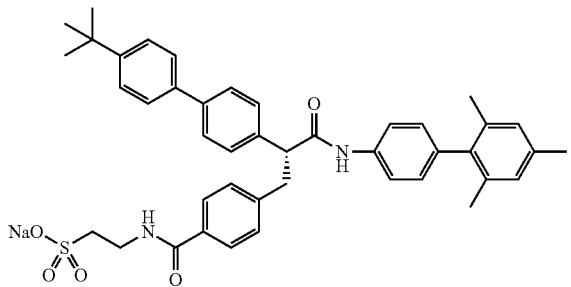

$^1$H NMR (500 MHz, DMSO-$d_6$): δ 7.65 (d, J=7.5 Hz, 2H), 7.51 (d, J=8.0 Hz, 2H), 7.48-7.43 (m, 11H), 7.38 (d, J=8.4 Hz, 2H), 7.28 (d, J=8.4 Hz, 2H), 6.92 (d, J=8.5 Hz, 2H), 6.80 (s, 1H), 3.97 (t, J=6.5 Hz, 1H), 3.71 (t, J=7.0 Hz, 2H), 3.50 (dd, J=9.0, 13.5 Hz, 1H), 3.08 (dd, J=6.6, 13.5 Hz, 1H), 2.99 (t, J=6.5 Hz, 2H), 2.19 (s, 3H), 1.86 (s, 6H), 1.28 (s, 9H). LC-MS m/z=702 $[C_{43}H_{45}N_2O_5SCl]^+$; Anal Calcd: (MF: $C_{43}H_{45}N_2O_5SClNa+1.2H_2O+0.1$ $NaHCO_3$) Calcd: C: 68.57, H: 6,34, N: 3.71 Found: C: 68.24, H: 5.98, N: 3.58.

Chiral HPLC conditions: The sample was diluted in ethanol at a 1 mg/mL concentration. It was injected into an HPLC system equipped with a Regis-Whelk-0l-786615, (S, S) 10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 28.908 min (enantiomeric excess: >98.79%).

Example 14: Ammonium-2-(R)-(4-{2-[4'-tert-butyl-biphenyl-4-yl)-2-[3-(4,4-dimethyl-cyclohex-1-enyl)-phenyl-4-ylcarbamoyl]-ethyl}-benzoylamino-ethane sulfonic acid

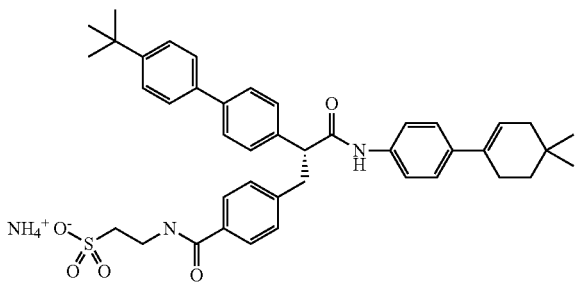

$^1$H NMR (500 MHz, DMSO-$d_6$): δ 10.07 (s, 1H), 8.39 (t, J=5.0 Hz, 1H), 7.64 (d, J=8.0 Hz, 2H), 7.57 (d, J=8.0 Hz, 2H), 7.54 (d, J=7.5 Hz, 2H), 7.50-7.44 (m, 6H), 7.32-7.29 (m, 4H), 6.0 (bs, 1H), 4.05 (dd, J=6.0, 8.5 Hz, 1H), 3.48 (dd, J=7.0, 12.5 Hz, 3H), 3.05 (dd, J=6.0, 13.5 Hz, 1H), 2.63 (t, J=7.0 Hz, 2H), 2.18 (bs, 3H), 1.94 (bs, 2H), 1.44 (t, J=12.0 Hz, 2H), 1.29 (s, 9H), 0.90 (s, 6H). LC-MS m/z=692 $[C_{42}H_{48}N_2O_5S]^+$; Anal Calcd: (MF: $C_{42}H_{43}N_2O_5S$+ $2.8H_2O+0.6$ $NH_3$) Calcd: C: 66.94, H: 7.41, N: 4.83 Found: C: 66.90, H: 7.20, N: 4.44.

Chiral HPLC conditions: The sample was diluted in ethanol at a 1 mg/mL concentration. It was injected into an HPLC system equipped with a Regis-Whelk-01-786615, (S, S) 10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 13.87 min (enantiomeric excess: >99.0%)

Example 15: 2-(4-[2-(4-Benzooxazol-2-yl-phenyl-carbamoyl)-2-4-(1R,4R)-1,7,7-trimethyl-bicyclo[2,2,1]hept-2-en-2-yl)-phenyl]-ethyl-benzoyl amino)-ethane sulfonic acid

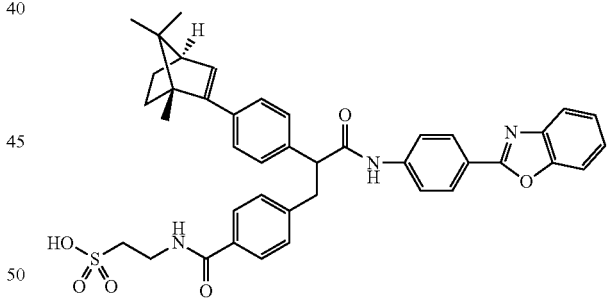

$^1$H NMR (500 MHz, DMSO-$d_6$): δ 8.13 (d, J=8.5 Hz, 2H), 7.74-7.65 (m, 4H), 7.40-7.38 (nn, 6H), 7.33 (d, J=8.0 Hz, 2H), 7.21 (d, J=8.0 Hz, 2H), 5.97 (d, J=3.5 Hz, 2H), 4.05 (t, J=6.0, Hz, 1H), 3.77 (t, J=6.5, Hz, 1H), 3.56-3.46 (m, 1H), 3.14 (dd, J=6.0, 14.0 Hz, 1H), 3.06 (t, J=6.5 Hz, 2H), 2.37 (t, J=3.5 Hz, 2H), 1.99-1.93 (m, 2H), 1.72-1.67 (m, 2H), 1.33-1.29 (m, 2H), 1.15-1.09 (m, 4H), 0.90 (s, 3H), 0.88 (s, 3H). LC-MS m/z=703 $[C_{41}H_{41}N_3O_6S]^+$ HPLC conditions: 250×10 mm T=23° C.; mobile phase=100% ACN/($H_2O$/ CAN+0.1 TFA) flow rate=1.0 mL/min; detection=254, 280, 220 nm retention time in min: 7.39 min (95.0%)

Example 16: Sodium-2-[4-(R)-2-(4'-tert-butyl-biphenyl-4-yl)-2-(4'-chloro-3'-methyl-phenyl-carbamoyl)-ethyl}-benzoylamino-ethane sulfonic acid

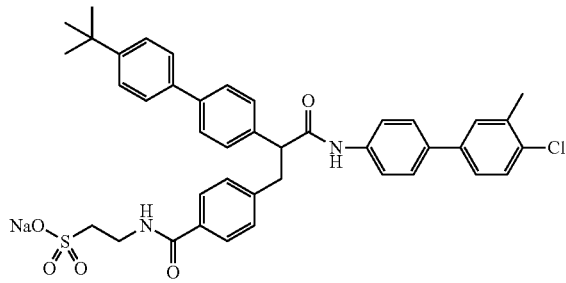

$^1$H NMR (500 MHz, DMSO-d$_6$): δ 7.71 (d, J=8.0 Hz, 2H), 7.59-7.44 (m, 13H), 7.36-7.33 (m, 4H), 4.0 (dd, J=6.0, 9.0 Hz, 1H), 3.77 (t, J=7.0 Hz, 2H), 3.56 (dd, J=9.0, 13.0 Hz, 1H), 3.14 (dd, J=6.0, 13.0 Hz, 1H), 3.06 (t, J=6.5 Hz, 2H), 2.41 (s, 3H), 1.34 (s, 9H), LC-MS m/z=731 [C$_{35}$H$_{36}$N$_2$O$_5$SClNa]$^+$

Example 17: Ammonium-2-(R)-(4-{2-[4'-tert-butyl-biphenyl-4-yl)-2-(4-methyl-benzooxazol-2-yl)phenylcarbamoyl]-ethyl}-benzoylamino)-ethane sulfonic acid Step 1: 4-(4-Methyl-benzooxazol-2-yl)-phenylamine

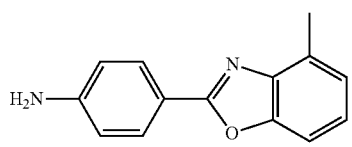 [SMILES: Cc1cccc2oc(-c3ccc(N)cc3)nc12]

To a suspension of 4-amino-benzoic acid (2.0 g, 14.5 mmol) in PPA (85 g) was added 2-amino-m-cresol (1.8 g, 15.3 mmol). The reaction was heated to 160° C. for 14 h, then carefully quenched in aqueous sodium carbonate (50% saturated) at room temperature, Ethyl acetate was added, and the organic layer was washed with water and brine, and dried over sodium sulfate. The crude product was obtained was subsequently purified by flash column chromatography on silica gel eluting with ethyl acetate in hexanes to afford the desired product, 4-(4-methyl-benzooxazol-2-yl)-phenylamine as a light pink solid, 1.8 g (56%). LC-MS m/z=225 [C$_{14}$H$_{12}$N$_2$O+H]$^+$.

Step 2: The Methods Described in Examples 1-6 were Used to Generate the Title Compound from 4-(4-Methyl-benzooxazol-2-yl)-phenylamine

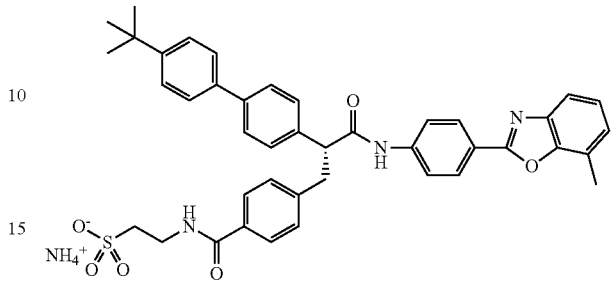

$^1$H NMR (500 MHz, DMSO-d$_6$): δ 10.48 (s, 1H), 8.41 (t, J=3.0 Hz, 1H), 8.12 (d, J=5.4 Hz, 2H), 7.77 (d, J=5.1 Hz, 2H), 7.67-7.46 (m, 11H), 7.34 (d, J=5.1 Hz, 1H), 7.25 (dd, J=4.5 Hz, 1H), 7.17 (d, J=4.8 Hz, 1H), 4.13 (t, J=6.0 Hz, 1H), 3.53-3.41 (m, 3H), 3.11 (dd, J=3.0, 6.5 Hz, 1H), 2.62 (t, J=3.9 Hz, 2H), 2.55 (s, 3H), 1.29 (s, 9H); LC-MS m/z=717[C$_{42}$H$_{41}$N$_3$O$_6$S]$^+$

Chiral HPLC Conditions:

The sample was diluted in ethanol at a 1 mg/mL concentration. It was injected into an HPLC system equipped with a Regis-Whelk-01-786615, (S, S) 10/100 250×10 mm column kept at 23° C. The column was eluted with a gradient of two solvents A and B for a 30 min period. The composition of the gradient ranged from 40% A to 70% A over this period (with the balance of the solvent being B) Solvent A was acetonitrile, solvent B was a mixture of 5% acetonitrile and 95% water containing 5 mM ammonium bicarbonate (pH adjusted to 6.5 with CO$_2$). The product was detected by UV at 254 nm. Retention time in min: 26.69 min (enantiomeric excess: >99.5%)

Example 18: Ammonium-2-(S)-(4-{2-[4'-tert-butyl-biphenyl-4-yl)-2-(4-methyl-benzooxazol-2-yl)phenylcarbamoyl]-ethyl}-benzoylamino)-ethanesulfonate This compound was generated using the methods described in Example 19

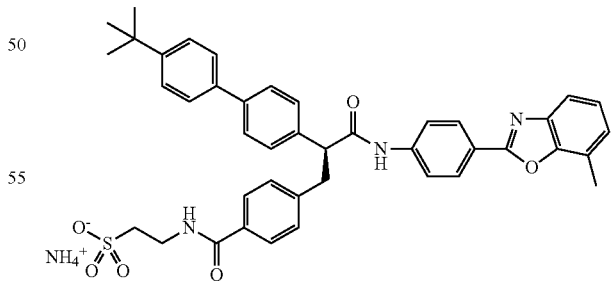

$^1$H NMR (500 MHz, DMSO-d$_6$): δ 10.48 (s, 1H), 8.41 (t, J=3.3 Hz, 1H), 8.11 (d, J=5.1 Hz, 2H), 7.78 (d, J=2.1 Hz, 2H), 7.67-7.46 (m, 11H), 7.34 (d, J=5.1 Hz, 1H), 7.25 (dd, J=4.8 Hz, 1H), 7.19 (d, J=4.8 Hz, 1H), 4.13 (t, J=6.0 Hz, 1H), 3.51-3.37 (m, 3H), 3.09 (dd, J=3.9, 4.5 Hz, 1H), 2.62 (t, J=1.2 Hz, 2H), 2.60 (s, 3H), 1.29 (s, 9H); LC-MS m/z=717[C$_{42}$H$_{41}$N$_3$O$_6$S]$^+$

Chiral HPLC Conditions:

The sample was diluted in ethanol at a 1 mg/mL concentration. It was injected into an HPLC system equipped with a Regis-Whelk-01-786615, (S, S) 10/100 250×10 mm column kept at 23° C., The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 26.48 min (enantiomeric excess: >99.8%)

Example 19: 2-{4-[(R)-2-[4-(4 (cis) tert-Butylcyclohexyl) phenyl]-2-(4'-chloro-2'-methyl-biphenyl-4-ylcarbamoyl)-ethyl]-benzoyl amino}-ethanesulfonic acid

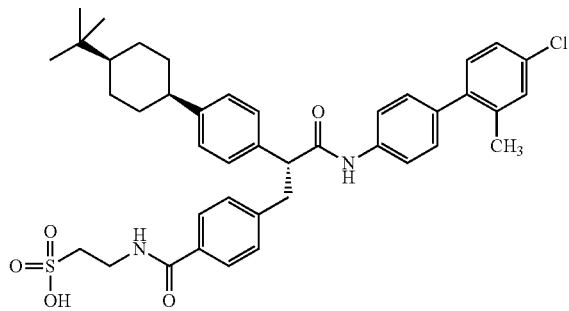 [SMILES: Cc1cc(Cl)ccc1-c1ccc(NC(=O)[C@H](Cc2ccc(C(=O)NCCS(=O)(=O)O)cc2)c2ccc([C@H]3CC[C@@H](C(C)(C)C)CC3)cc2)cc1]

Step 1: 4-Chloromethyl benzoic acid tert-butyl ester

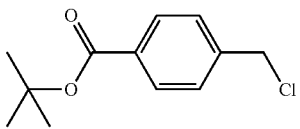

Oxalyl chloride (101 mL) was added dropwise over a 30 min period to a slurry of 4-chloromethyl benzoic acid (181.8 g) in dichloromethane (1.2 L) containing 5 mL of DMF. After the addition was complete the reaction mixture was stirred at room temperature for 24 h, concentrated under reduced pressure and then co-evaporated with toluene, To the residue was added 908 mL of MTBE and the mixture was cooled to −5° C. A solution of potassium tert-butoxide in THF (1.0 M, 1172 mL) was added dropwise ensuring that the internal temperature remained below 10° C. After the addition was complete, the reaction mixture was stiffed for an additional 1 hour then treated with 500 mL of saturated sodium bicarbonate solution. After stirring 5 minutes, then settling, the organic phase was separated, washed with saturated sodium chloride solution and dried over magnesium sulfate. Concentration yielded 241.7 g (86% yield) as a dark oil.

HNMR: $CDCl_3$, 1.59 ppm (s, 9H), 4.61 (s, 2H), 7.45 (d, 2H), 7.99 (d, 2H)

Step 2: 4-Iodomethyl benzoic acid tert-butyl ester

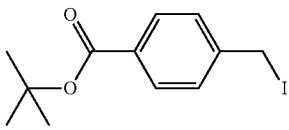

Sodium iodide (229.2 g) was added to a solution of 4-chloromethyl benzoic acid tert-butyl ester (315.2 g) in acetone (1.5 L). The reaction mixture was heated to reflux for about 2 h and then allowed to cool to room temperature. The precipitate was removed by filtration and the filtrate concentrated under reduced pressure. The residue was partitioned between water (500 mL) and MTBE (1500 mL). The organic phase was washed with saturated sodium bicarbonate and dried over magnesium sulfate. Concentration under reduced pressure afforded 442.2 g (97% yield) dark oil.

HNMR: $CDCl_3$, 1.59 ppm (s, 9H), 4.47 (s, 2H), 7.42 (d, 2H), 7.91 (d, 2H)

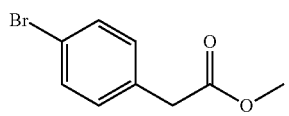

Step 3: 4-Bromophenyl Acetic Acid Methyl Ester

Sulfuric acid (56.5 mL) was very slowly added to a solution of 206.6 g of 4-bromophenyl acetic acid in methanol (800 mL). After completion of the addition, the mixture was heated to reflux for 2 h. The reflux condenser was replaced by a distillation head and 400 mL of methanol was atmospherically distilled. The temperature was the reduced to 50° C. and the reaction stirred for additional 16 h, when the mixture was then cooled to room temperature and partitioned between dichloromethane (1 L) and water (600 mL). The organic phase was washed with saturated sodium bicarbonate and dried over magnesium sulfate. Concentration under reduced pressure provided 220.1 g (98% yield) colorless oil.

HNMR: $CDCl_3$, 3.59 (s, 2H), 3.70 (s, 3H), 7.16 (d, 2H), 7.45 (d, 2H)

Step 4: 4-[2-(4-Bromo-phenyl)-2-methoxycarbonyl-ethyl]-benzoic acid tert-butyl ester

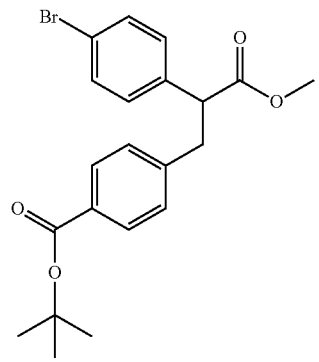 [SMILES: COC(=O)C(Cc1ccc(C(=O)OC(C)(C)C)cc1)c1ccc(Br)cc1]

A solution of 246.63 g of methyl-4-bromophenyl acetate and 342.54 g of 4-Iodomethyl benzoic acid tert-butyl ester in THF (1233 mL) was cooled to −8 A solution of lithium hexamethyl disilazide in THF (1185 mL, 1.0 M) was added dropwise ensuring that the temperature remain below −2° C. After the addition was complete, the reaction was allowed to proceed for ~45 min at the same temperature and then poured over a stirring mixture of ethyl acetate (2.46 L) and water (1.23 L) The organic phase was washed with saturated ammonium chloride and then with water. Dried over magnesium sulfate and concentrated under reduced pressure to obtain 450.5 g (100% yield) thick oil.

HNMR: CDCl$_3$, 1.41 (s, 9H), 2.88-2.90 (m, 1H). 3.24-3.28 (m, 1H), 3.45 (s, 3H), 3.63 (t, 1H). 6.96-6.99 (m, 4H), 7.25 (d, 2H), 7.68 (d, 2H)

Step 5: (R)-2-(4-Bromo-phenyl)-3-(4-tert-butoxy-carbonyl-phenyl)-propionate (S)-2-hydroxymethyl pyrrolidinium

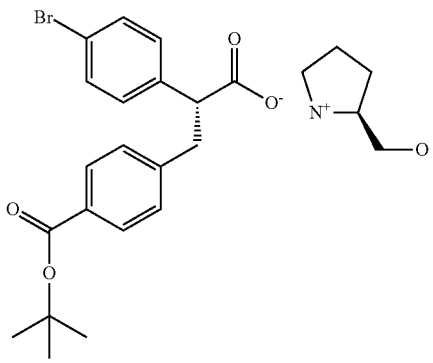 [SMILES: CC(C)(C)OC(=O)c1ccc(C[C@@H](C(=O)[O-])c2ccc(Br)cc2)cc1 ; OC[C@@H]1CCC[NH2+]1]

4-[2-(4-Bromo-phenyl)-2-methoxycarbonyl-ethyl]-benzoic acid tert-butyl ester (769 g) was dissolved in THF (5.38 L) and water (3.85 L) and treated with lithium hydroxide monohydrate (153.9 g). The reaction mixture was heated to 45° C. for approximately 1 hour. After allowing the reaction to cool to 32° C., the reaction was poured into a stirring mixture of 11.6 L of ethyl acetate and 3.9 L of 1M aqueous hydrochloric acid. The separated organic layer was washed with water, dried over magnesium sulfate and concentrated under reduced pressure. Added ethyl acetate (2.045 L) to the residue and warmed to 78° C. for ~5 min for dissolution. The mixture was allowed to cool to 68° C. and treated with (S)-(+)-prolinol (90.5 mL). The solid that precipitated after cooling to room temperature was filtered and rinsed with a cold mixture (7° C.) of 1:1 ethyl acetate: heptane (740 mL). The solid isolated (232.4 g, 35% yield) was shown to have 94% enantiomeric excess (R isomer) by chiral HPLC analysis.

HNMR: CDCl$_3$, 1.57 (s, 9H), 1.67-1.74, (m, 2H), 2.64-2.69 (m, 1H), 2.76-2.81 (m, 1H), 2.94-2.99 (m, 1H), 3.14-3.19 (m, 1H), 3.32-3.39 (m, 2H), 3.60-3.67 (m, 2H), 7.14-7.19 (m, 4H), 7.35 (d, 2H), 7.80 (d, 2H).

Conditions for chiral HPLC analysis: Kromasil 100-5-TBB column, 250×4.6 mm, 1 mL/min, 15% (1% AcOH/MTBE)/85% hexanes, 230/240/250 nm.

To 228 g of the product above were added 684 mL of ethyl acetate. The mixture was warmed to reflux (additional 228 mL of ethyl acetate were added when the temperature reached 69° C. for mobility) where it was held for about 10 min. The suspension was then allowed to cool to room temperature and filtered. Vacuum dried at 50° C. Product is a white solid (224.6 g, 98% yield) "R' enantiomer with enantiomeric excess of 96.9% by HPLC analysis as described above.

Step 6: 4-[(R)-2-(4-Bromo-phenyl)-2-carboxy-ethyl-]-benzoic acid tert-butyl ester

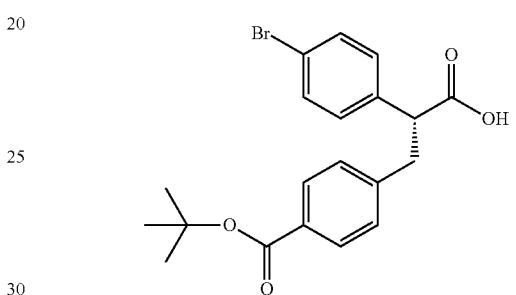

A stirring slurry of 216.8 g of (R)-2-(4-Bromo-phenyl)-3-(4-tert-butoxycarbonyl-phenyl)-propionate (S)-2-hydroxymethyl pyrrolidinium in 2168 mL of ethyl acetate at 21° C. was treated 1084 mL of 10% aqueous formic acid. After 20 minutes, the separated organic phase was washed with water and dried over magnesium sulfate. The ethyl acetate solution was atmospherically displaced into heptanes to yield the product as a granular solid, 166.3 g (96% yield) of white solid, enantiomeric excess ("R" enantiomer) of 96.9% by chiral HPLC analysis as described above.

HNMR: CDCl$_3$, 1.50 (s, 9H), 2.96-3.00 (m, 1H), 3.32-3.37 (m, 1H), 3.73 (t, 1H), 7.03-7.08 (m, 4H), 7.35 (d, 2H), 7.76 (d, 2H)

Step 7: 4-{(R)-2-[4-(4-tert-Butyl-cyclohex-1-enyl)-phenyl]-2-carboxy-ethyl}-benzoic acid tert-butyl ester

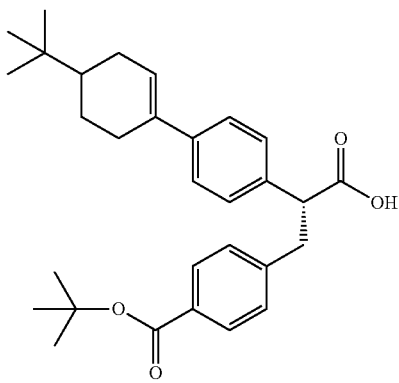 [SMILES: CC(C)(C)OC(=O)c1ccc(C[C@@H](C(=O)O)c2ccc(C3=CCC(C(C)(C)C)CC3)cc2)cc1]

A mixture of 3.1 g of 4-[(R)-2-(4-Bromo-phenyl)-2-carboxy-ethyl-]-benzoic acid tert-butyl ester (3. Step 2, above), 1.5 g of 4-t-butyl-cyclohex-1-enyl boronic acid, 644 mg of PdCl$_2$(P(o-tolyl)$_3$)$_2$, and 2.21 g of sodium carbonate in 12 mL of DME and 6 mL of ethanol and 3 mL of water was heated to reflux for a 16 h period. The reaction mixture was quenched with an excess of aqueous ammonium chloride, added ethyl acetate and the heterogeneous mixture was filtered through a celite pad. The organic phase was washed (water, saturated sodium chloride), dried over magnesium sulfate and concentrated. The residue was chromatographed on silica gel using a methanol-dichloromethane gradient to yield the carboxylic acid.

HNMR (300 MHz, CDCl3, partial): 6.14 (1H, m), 1.58 (9H, s), 0.92 (9H, s)

LCMS m/z=407.9 [(C$_{30}$H$_{38}$O$_4$+H)—C$_4$H$_9$]$^+$

Step 8: 4-{(R)-2-[4-(4-(cis)-tert-Butyl-cyclohexyl)-phenyl]-2-carboxy-ethyl}-benzoic acid tert-butyl ester

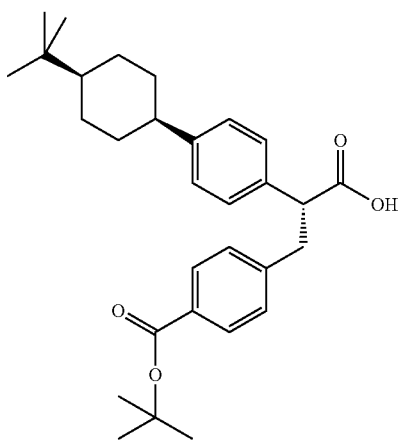 [SMILES: CC(C)(C)OC(=O)c1ccc(C[C@@H](C(=O)O)c2ccc([C@H]3CC[C@@H](C(C)(C)C)CC3)cc2)cc1]

To a solution of 4-{(R)-2-[4-(4-tert-Butyl-cyclohex-1-enyl)-phenyl]-2-carboxy-ethyl}-benzoic acid tert-butyl ester (3.0 g) in ethyl acetate (100 mL) added 10% palladium on carbon (300 mg). The mixture was stirred under a balloon filled with hydrogen, until proton NMR indicated the disappearance of the olefinic signal. The reaction was filtered through a plug of celite, and the filtrate was concentrated under reduced pressure to give a mixture of cis/trans isomers (in a ratio of 1:1, based on $^1$H NMR). The cis$^1$ and trans isomers were separated by reverse phase chromatography with the latter being cis (1.34 g, 2.9 mmol, 35%). $^1$H NMR (CDCl$_3$): δ 0.95 (9H, s), 1.23-1.38 (4H, m), 1.58 (9H, s), 1.88-1.98. (4H, m), 2.39-2.56 (1H, m), 3.05-3.12 (1H, m), 3.19-3.50 (1H, m), 3.82-3.90 (1H, m), 7.19-7.22 (6H, m), 8.81 (2H, d).

1. Based on the following reference and references within the article, the cis was assigned as described above. Garbisch, E. W.; Patterson, D. B., *J. Am. Chem. Soc.,* 1963, 85, 3228.

Step 9: 4-[(R)-2-[4-(4-(cis)-tert-Butyl-cyclohexyl)-phenyl]-2-(4'-chlor-2'-methyl-biphenyl-4-ylcarbamoyl)-ethyl]-benzoic acid tert-butyl ester

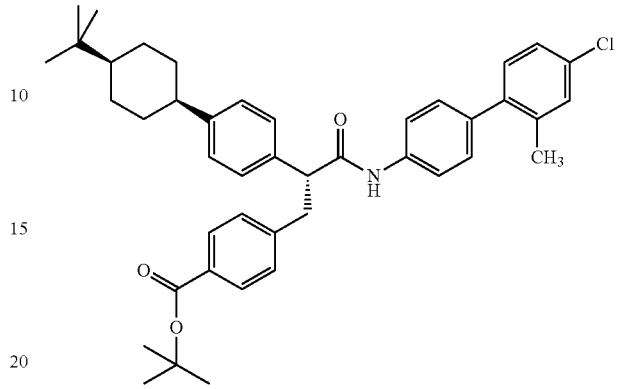

To 4-{(R)-2-[4-(4-(cis)-tert-Butyl-cyclohexyl)-phenyl]-2-carboxy-ethyl}-benzoic acid tert-butyl ester (300 mg) in dichloromethane (10 mL) was added a solution of oxalyl chloride in dichloromethane (2.0M, 0.54 mL) followed by 2 drops of DMF. The reaction mixture was stirred at room temperature for 2 h and concentrated under reduced pressure. The residue was dissolved in dichloromethane (20 mL), and treated with 4'-Chloro-2'-methyl-biphenyl-4-amine (142 mg) and diisopropyl ethyl amine (0.120 mL). After stirring for 1h at room temperature, the solvent was removed under reduced pressure and the residue treated with methanol. The white precipitated formed was washed with methanol, dried under vacuum and used without further purification in the following step.

Step 10: 4-[(R)-2-[4-(4-(cis)-tert-Butyl-cyclohexyl)-phenyl]-2-4'-chlor-2'-methyl-biphenyl-4-ylcarbamoyl)-ethyl]-benzoic acid

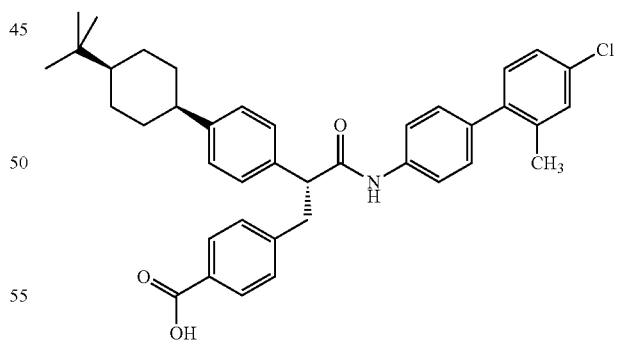

A solution of 431 mg of 4-[(R)-2-[4-(4-(cis)-tert-Butyl-cyclohexyl)-phenyl]-2-(4'-chlor-2'-methyl-biphenyl-4-yl-carbamoyl)-ethyl]-benzoic acid tert-butyl ester in dichloromethane (10 mL) was treated with trifluoroacetic acid (2 mL) and concentrated aqueous hydrochloric acid (1 mL), The resulting mixture was stirred for 16 h at room temperature. The organic phase was separated, washed with water and dried over magnesium sulfate. Concentration left a residue that was used without further purification.

Step 11: 2-{4-[(R)-2-[4-(4-(cis)-tert-Butyl-cyclohexyl)-phenyl]-2-(4'-chloro-2'-methyl-biphenyl-4-ylcarbamoyl)-ethyl]-benzoylamino}-ethanesulfonic acid

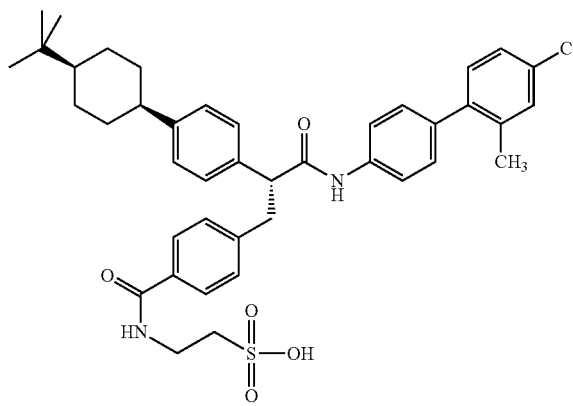 [SMILES: Cc1cc(Cl)ccc1-c1ccc(NC(=O)[C@H](Cc2ccc(C(=O)NCCS(=O)(=O)O)cc2)c2ccc([C@H]3CC[C@@H](C(C)(C)C)CC3)cc2)cc1]

(R)-4-[2-[4-(4-(cis)-tert-Butyl-cyclohexyl)-phenyl]-2-(4'-chloro-2'-methyl-biphenyl-4-ylcarbamoyl)-ethyl]-benzoic acid (350 mg, 0.6 mmol), was taken up in 3 mL of DMF, followed by addition of HOBt (133 mg, 0.9 mmol), EDCI (132 mg, 0.7 mmol), taurine (86 mg, 0.7 mmol) and Hunig's base (374 mg, 2.9 mmol). The resulting reaction mixture was then stirred for 16 h at room temperature. The reaction solution was diluted with EtOAc (25 mL) and 10 mL of water, acidified with 2.4 N HCl. The layers were separated and the aqueous layer was extracted with EtOAc (2×20 mL). The organic extracts were combined, dried with $Na_2SO_4$, filtered through a frit and concentrated under reduced pressure to give a foam. The material was subjected to reverse phase HPLC purification to give the desired product as a white solid (150 mg, 36%), $^1$H NMR (CD$_3$OD): δ 0.89 (9H, s), 1.10-1.60 (6H, m), 1.80-1.90 (4H, m), 2.38 (3H, s), 2.32-2.53 (1H, m), 3.05-3.10 (4H, m), 3.47-3.55 (1 h, dd), 3.77 (2H, t), 3.93-3.98 (1H, m), 7.09-7.47 (11H, m), 7.50 (2H, d), 7.70 (2H, d). Anal. Calcd. For $C_{42}H_{47}ClN_2O_5S+NH_3+1.2H_2O$; C=65.22; H=7.13; N=5.57. Found C=65.31; H=7.00; N=5.57.

Step 12. (R)-2-{4-[2-[4-(4-(trans)-tert-Butyl-cyclohexyl)-phenyl]-2-(4'-chloro-2'-methyl-biphenyl-4-ylcarbamoyl)-ethyl]-benzoylamino}-ethanesulfonic acid The trans isomer isolated from step 8, (R)-4-{2-[4-(4-(trans)-tert-Butyl-cyclohexyl)-phenyl]-2-carboxy-ethyl}-benzoic acid tert-butyl ester, was subjected to the procedures of steps 9-11 to give (R)-2-{4-[2-[4-(4-(trans)-tert-butyl-cyclohexyl)-phenyl]-2-(4'-chloro-2'-methyl-biphenyl-4-ylcarbamoyl)-ethyl]-benzoylamino}-ethanesulfonic acid.

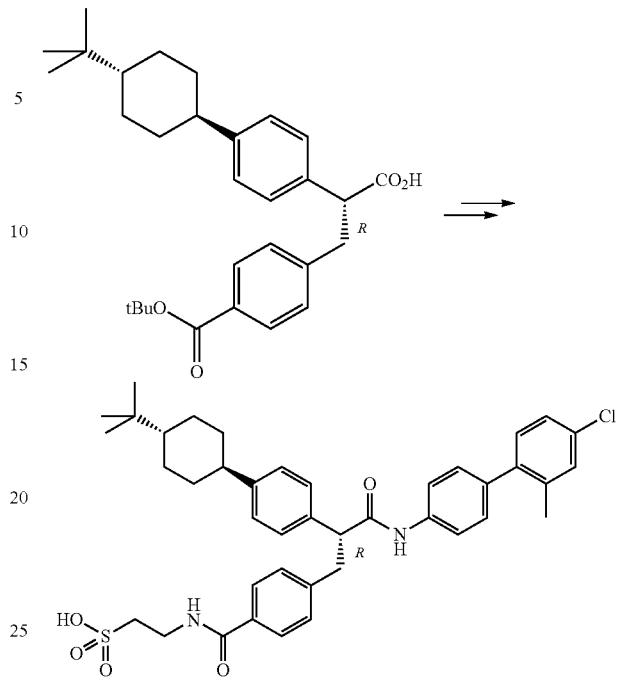

Example 20

The compound of Formula IIIa (below) was incubated for 60 minutes at 37 C with mouse, rat, dog, monkey, and human liver microsomes.

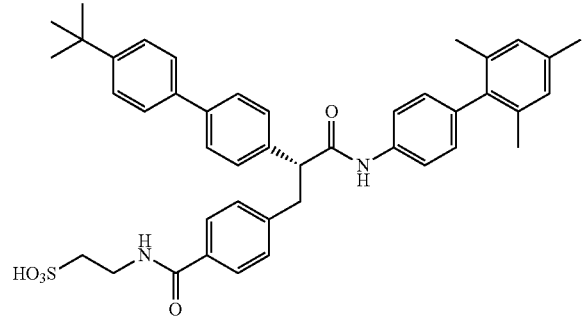

IIIa

Concentrations of IIIa were measured at multiple time points by LC-MS/MS. IIIa was stable with predicted clearance well below hepatic blood flow in all species. Results are shown below.

| | Species | | | | |
|---|---|---|---|---|---|
| Parameter | Human | Mouse | Rat | Monkey | Dog |
| $1^{st}$-order kinetic rate constant (1/min) | 0.0021 | 0.0017 | 0.0058 | 0.0057 | 0.0016 |
| Predicted systemic clearance (mL/min/kg body weight) | 3.18 | 7.05 | 13.8 | 11.9 | 4.01 |

Example 21

Pharmacokinetics of IIIa were evaluated after both oral and IV administration in mice, rats, dogs, and monkeys. In addition to plasma PK studies, experiments in rats revealed that IIIa was primarily excreted in the bile with negligible levels detected in the urine (see below)

| Species | IV Dose (mg/kg) | PO Dose (mg/kg) | $C_{max}$ (µg/mL) | $T_{max}$ (hr) | $AUC_{0-last}$ (µg*hr/mL) | $t_{1/2}$ (hr) | Cl (L/hr/kg) | $V_{SS}$ (L/kg) | F (%) |
|---|---|---|---|---|---|---|---|---|---|
| Mouse | 1 | 3 | 1.71 | 6.0 | 16.3 | 5.9 | 1.33 | 0.62 | 47 |
| Rat | 1 | 3 | 1.33 | 2.0 | 7.6 | 10.9 | 0.14 | 0.30 | 36 |
| Dog | 1 | 3 | 10.9 | 4.0 | 225 | 46.0 | 0.0042 | 0.24 | 54 |
| Monkey | 1 | 3 | 1.25 | 4.0 | 9.85 | 16.2 | 0.068 | 0.16 | 21 |

Example 22

Oral doses of IIIa were administered to normal healthy volunteers (NHV) and subjects with type 2 diabetes mellitus (T2DM). A single center, randomized, double-blind, placebo-controlled single ascending dose study was done in both NHV (n=48) and T2DM subjects (n=8). Dose escalation only occurred after review of safety and tolerability data from previous dose levels (n=8/cohort; 2-placebo & 6-IIIa).

Dosing of the T2DM cohort was initiated only after the equivalent dose had been administered to NHV and safety data had been reviewed. All subjects were administered IIIa in the morning after an overnight fast with the exception of the NHV in the 40 mg cohort. NHV subjects in the 40 mg cohort initially received IIIa in a fasted state. Following a 3 week washout period, IIIa was readministered after breakfast at 40 mg to determine the effects of food consumption on pharmacokinetics.

| Normal Healthy Volunteers | | 6972 Dose Level | | | | | | |
|---|---|---|---|---|---|---|---|---|
| | | Placebo | 2 mg | 10 mg | 40 mg | 120 mg | 240 mg | 480 mg |
| Number of subjects | | 12 | 6 | 6 | 6 | 6 | 6 | 6 |
| Age (yrs) | | 40.6 (11.3) | 41.0 (12.0) | 38.2 (7.6) | 37.2 (12.7) | 42.8 (10.5) | 45.5 (13.2) | 37.0 (15.1) |
| Gender (n) | Female | 2 | 2 | 1 | 1 | 1 | 4 | 1 |
| | Male | 10 | 4 | 5 | 5 | 5 | 2 | 5 |
| Race (n) | White | 4 | 3 | 1 | 1 | 2 | 4 | 1 |
| | African American | 8 | 3 | 5 | 5 | 3 | 2 | 5 |
| | American Indian/Alaskan Native | 0 | 0 | 0 | 0 | 1 | 0 | 0 |
| BMI (kg/m$^2$) | | 25.5 (3.6) | 25.8 (2.2) | 26.9 (3.5) | 26.9 (2.4) | 26.8 (2.8) | 25.1 (2.7) | 26.9 (1.2) |

| T2DM Subjects | | 6972 Dose Level | |
|---|---|---|---|
| | | Placebo | 40 mg |
| Number of subjects | | 2 | 6 |
| Age (yrs) | | 53.5 (7.8) | 54.3 (9.5) |
| Gender (n) | Female | 0 | 2 |
| | Male | 2 | 4 |
| Race (n) | White | 2 | 3 |
| | African American | 0 | 3 |
| BMI (kg/m$^2$) | | 25.5 (3.6) | 25.8 (2.2) |

As shown above, IIIa was well tolerated with no clinically significant or dose dependent changes in hematology, clinical chemistry, EKG, or vital signs. There were no cases of hypoglycemia (glucose <60 mg/dL) and there were no serious adverse events. Study drug related treatment emergent adverse events (TEAE) were observed in the NHV but not the T2DM subjects and are listed below.

| Normal Healthy Volunteers | | 6972 Dose Level | | | | | | |
|---|---|---|---|---|---|---|---|---|
| | | Placebo | 2 mg | 10 mg | 40 mg | 120 mg | 240 mg | 480 mg |
| Number of subjects | | 12 | 6 | 6 | 6 | 6 | 6 | 6 |
| Any study drug related TEAE | | 1 (8.3) | 0 (0.0) | 1 (16.7) | 0 (0.0) | 2 (33.3) | 2 (33.3) | 2 (33.3) |
| Nervous systems disorders | Headache | 1 (8.3) | 0 (0.0) | 1 (16.7) | 0 (0.0) | 2 (33.3) | 1 (16.7) | 0 (0.0) |

-continued

| Normal Healthy Volunteers | | Placebo | 2 mg | 10 mg | 40 mg | 120 mg | 240 mg | 480 mg |
|---|---|---|---|---|---|---|---|---|
| | | | | 6972 Dose Level | | | | |
| Gastrointestinal disorders | Nausea | 0 (0.0) | 0 (0.0) | 0 (0.0) | 0 (0.0) | 0 (0.0) | 1 (16.7) | 1 (16.7) |
| | Diarrhoea | 0 (0.0) | 0 (0.0) | 0 (0.0) | 0 (0.0) | 0 (0.0) | 0 (0.0) | 1 (16.7) |
| | Vomiting | 0 (0.0) | 0 (0.0) | 0 (0.0) | 0 (0.0) | 0 (0.0) | 0 (0.0) | 1 (16.7) |

IIIa was well absorbed after oral administration with peak plasma concentrations reached approximately 5-8 hours post dose. Consistent with preclinical predictions, clearance was slow and IIIa was not detected in the urine. Dose dependent increases in plasma exposure were observed.

Pharmacokinetics of a 40 mg dose of IIIa were examined twice in healthy volunteers. IIIa was initially administered after an overnight fast. Following a 3-week washout period, IIIa was readministered after breakfast to determine the effects of food consumption. Pharmacokinetics were comparable with fasted or fed administration.

Pharmacokinetics of a 40 mg dose of IIIa were examined in subjects with type 2 diabetes mellitus. Pharmacokinetics were comparable in the healthy volunteers and the diabetic subjects.

on solution stability was determined by HPLC. Plasma levels of Formula IIIa were measured by LCMS/MS.

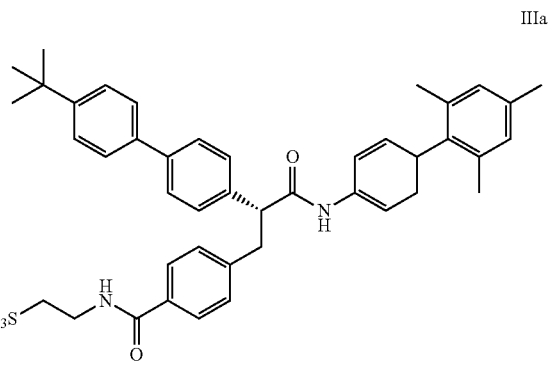

IIIa

| Pharmacokinetic parameters for 40 mg dose in healthy volunteers and diabetic subjects | | | | | | | |
|---|---|---|---|---|---|---|---|
| Subjects | Dose (mg) | Nutrition | $C_{max}$ (µg/mL) | $T_{max}$ (hr) | $AUC_{0\text{-}inf}$ (ng*hr/mL) | $t_{1/2}$ (hr) | CL/F (L/hr) | $V_d$ (L/hr) |
| Normal healthy volunteer | 40 | Fasted | 893 | 8.4 | 32,715 | 51.6 | 1.33 | 96 |
| Normal healthy volunteer | 40 | Fed | 779 | 7.2 | 25,229 | 53.8 | 1.67 | 125 |
| Diabetic | 40 | Fasted | 1422 | 7.5 | 33,721 | 58.5 | 1.32 | 101 |

IIIa lowered fasting plasma glucose in normal healthy volunteers in a dose dependent manner. Glucose suppression continued through 48 hours. See below:

IIIa also lowered fasting plasma glucose in T2DM subjects by 50 mg/dL (placebo adjusted=57 mg/dL) after a single dose. Glucose suppression continued through 48 hours.

| Treatment | Baseline Glucose (mg/dL) |
|---|---|
| Placebo | 130 |
| 40 mg | 160 |

As shown above, IIIa is a potent and selective glucagon receptor antagonist and is well tolerated in a single ascending dose study. In addition, the pharmacokinetics support once daily dosing in humans. IIIa also reduces fasting plasma glucose in normal healthy volunteers and diabetic subjects after a single dose and is effective for the treatment of T2DM.

Example 23

Solubility of a sodium salt of Formula IIIa (below) was determined in water and at various pH values and simulated intestinal fluids using HPLC and UV analysis with and without modified beta-cyclodextrin (Captisol®). Phase solubility was used to estimate the Captisol®: Formula IIIa binding constant. The influence of Captisol® on oral absorption was modelled as shown below. The effect of Captisol®

This was a single center, randomized, double-blind, placebo-controlled single ascending dose study in both normal healthy volunteers (NHV) (n=48) and subjects with type 2 diabetes mellitus (T2DM) (n=8). All subjects were administered Formula IIIa as a solution formulated with Captisol® after an overnight fast with the exception of the NHV in the 40 mg cohort. The NHV 40 mg cohort initially received Formula IIIa in a fasted state. Following a washout period, subjects received 40 mg Formula IIIa after breakfast to explore the effects of food consumption on pharmacokinetics.

| Solubility of Formula IIIa sodium salt at 25° C. | |
|---|---|
| Media | Solubility (mg/mL)[a] |
| Water | 0.21 ± 0.01 |
| pH 4.0, 6.8, 7.4 & 10 buffers | 0.04 – 0.06 ± 0.01 |
| 0.1N HCL | 0.06 ± 0.00 |
| 0.01N HCL | 0.07 ± 0.00 |
| Simulated gastric fluid (SGF) | 0.04 ± 0.01 |
| Fasted state simulated intestinal fluid (FaSSIF) | 0.21 ± 0.00 |
| Fed state simulated intestinal fluid (FeSSIF) | 6.54 ± 0.19 |
| 15% w/v Captisol ® | 11.53 ± 0.04[b] |
| 35% w/v Captisol ® | 32.86 ± 0.44[b] |

[a] = Solubility measured by high-performance liquid chromatography (HPLC) after 24-hour equilibration except where noted.
[b] = Solubility measured at ambient conditions by UV spectroscopy (UV) after 2-3day equilibration.

The Powder-in-Bottle has 2 Fills that are selected to enable different and yet to be finally selected wide range of doses (combination of multiple vials allowed). There is very little or essentially no development with minimal DS requirements. Use DS methods and supported by DS stability with little adaptation. The present embodiments allow for rapid transition to first in man (FIM). Some embodiments relate to the use of Captisol® as constitution vehicle. Some embodiments do not require solubilizing all doses in small volume but assures all are in solution and removes solubilization/dissolution limited absorption. Some embodiments ensure maximum drug exposure over a broad ascending dose FIM. Two concentrations of Captisol® selected across 2 series of concentrations minimizes the number of placebos to collect safety comparisons with fewer subjects.

Formula IIIa sodium salt administered in this clinical trial as a solution in Captisol® was well tolerated. Consistent with modeling predictions, absorption was facilitated using Captisol® and dose dependent increases in plasma exposure were observed. Mechanistic modeling predicts the impact of dosing with different CD levels on PK (Cmax, Tmax) from solution and also can be extended to solid dosage forms. This approach may enable rational guidance for dosing to achieve specific PK profiles and/or maximum bioavailability using a CD such as Captisol®. This study demonstrated that Captisol® provided the means to assure solubility was not limiting absorption and permitted administration of a wide range of doses to achieve the intensity of exposures sought from using drug substance alone without need for lengthy dosage form design and substantial analytical development. The extemporaneous prepared solutions permitted accept- Formula IIIa Dosing Solution Composition Matrix

| | Protocol Dose Level | | | | | |
|---|---|---|---|---|---|---|
| | 1 | 2 | 3 | 4 | 5 | 6 |
| Formula IIIa Sodium salt | 2 mg | 10 mg | 40 mg | 120 mg | 240 mg | 480 mg |
| Captisol | 600 mg | 600 mg | 600 mg | 7.0 g | 7.0 g | 7.0 g |
| Dose Volume | | 4.0 mL | | | 20.0 mL | |
| Placebo | 4.0 mL aqueous solution containing 600 mg Captisol | | | 20.0 mL aqueous solution containing 7 g Captisol | | |
| Captisol concentration | 15% w/v | | | 35% w/v | | |
| Formula IIIa concentration | 0.5 mg/mL | 2.5 mg/mL | 10 mg/mL | 6 mg/mL | 12 mg/mL | 24 mg/mL |
| Approx. API/Captisol Mole ratio | 1/100 | 1/20 | 1/5 | 1/20 | 1/10 | 1/5 |

Powder-in-Bottle Dose Preparation Kits

| Protocol Dose Level | Dose | Configuration of Kit |
|---|---|---|
| 1 | 2 mg | 1 × 10 mg bottle |
| 2 | 10 mg | 5 × 10 mg bottles |
| 3 | 40 mg | 2 × 10 mg + 3 × 60 mg bottles |
| 4 | 120 mg | 3 × 10 mg + 2 × 60 mg bottles |
| 5 | 240 mg | 5 × 60 mg bottles |
| 6 | 480 mg | 10 × 60 mg bottles |

Plasma levels of Formula IIIa were measured by validated LC-MS/MS method. Formula IIIa was well absorbed after oral administration with peak plasma concentrations reached approximately 5-8 hours post dose. Consistent with preclinical predictions, clearance was slow and Formula IIIa was not detected in the urine. Dose dependent increases in plasma exposure were observed.

able blinding and dosing volumes that were palatable to subjects and an acceptable, rapid path to the clinic.

Example 24

In type 2 diabetes mellitus (T2DM), inappropriately elevated levels of glucagon exacerbate hyperglycemia and its associated complications. Not wishing to be bound to a particular theory, it has been observed that antagonism of glucagon action reduces blood glucose levels and hemoglobin A1c in patients with T2DM. The novel, selective, orally bioavailable glucagon receptor antagonist, Formula IIIa (below), was investigated regarding its pharmacokinetics (PK), safety, and pharmacodynamics (PD) in a first-in-human, ascending, single-dose, double blind, placebo-controlled study in normal healthy (NH) and T2DM subjects (NCT01919684).

Pharmacokinetic parameters for 40 mg dose in healthy volunteers and diabetic subjects

| Subjects | Dose (mg) | Nutrition | $C_{max}$ (µg/mL) | $T_{max}$ (hr) | $AUC_{0\text{-}inf}$ (ng*hr/mL) | $t_{1/2}$ (hr) | CL/F (L/hr) | $V_d$ (L/hr) |
|---|---|---|---|---|---|---|---|---|
| Normal healthy volunteer | 40 | Fasted | 893 | 8.4 | 32,715 | 51.6 | 1.33 | 96 |
| Normal healthy volunteer | 40 | Fed | 779 | 7.2 | 25,229 | 53.8 | 1.67 | 125 |
| Diabetic | 40 | Fasted | 1422 | 7.5 | 33,721 | 58.5 | 1.32 | 101 |

IIIa

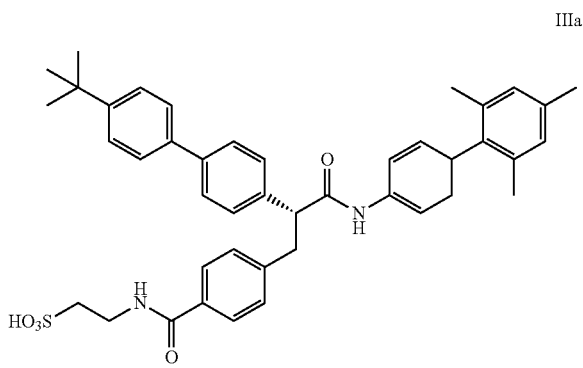 [SMILES: Cc1cc(C)c(C2C=CC(NC(=O)[C@H](Cc3ccc(C(=O)NCCS(=O)(=O)O)cc3)c3ccc(-c4ccc(C(C)(C)C)cc4)cc3)=CC2)c(C)c1]

A total of 56 participants were enrolled, 48 NH subjects and 8 T2DM subjects. The dose range was 2 to 480 mg for NH subjects. The T2DM subjects received a dose of 40 mg.

Formula IIIa was well tolerated and considered safe up to the highest dose tested in NH and T2DM subjects. Formula IIIa was well-absorbed after oral administration; peak plasma concentrations were reached approximately 5 to 8 hours post dose with a long elimination half-life of about 50 hours. Such data supports, for example, once-daily dosing of Formula III. The effects of Formula IIIa on fasting and post-prandial plasma glucose, glucagon, insulin, and glucagon-like peptide-1 (GLP-1) were evaluated in NH and T2DM subjects, and a meal tolerance test (MTT) and continuous glucose monitoring (CGM) were performed in T2DM subjects. In NH subjects, treatment with Formula IIIa resulted in small decreases in glucose levels approximating dose-dependency, and also lowered glucose levels in T2DM subjects. The decrease in glucose was most obvious in the fasting plasma glucose (FPG) levels 24 and 48 hours post-dose. The magnitude of decrease in FPG was greater in subjects with T2DM than in NH subjects.

CGM did not reveal a consistent trend in the change in daytime plasma glucose levels in subjects with T2DM compared to baseline. However, a within-group trend towards lower nighttime glucose was observed, as well as a reduction in 24-hour glucose AUC. The mean glucagon and total GLP-1 levels were increased in NH subjects in a dose-dependent manner up to 240 mg, especially apparent between 24 to 96 hours post-dose. The glucagon and total GLP-1 levels after 480 mg were slightly below the expected levels. Though not wishing to be bound to a particular theory, this may indicate that response to Formula IIIa may have reached a maximum. The mean glucagon and total GLP-1 levels were increased compared to placebo treatment in subjects with T2DM; most obvious 24 to 72 hours post-dose and greater than that in NH subjects. Formula IIIa treatment did not generate a consistent trend in the changes in the active GLP-1 or insulin levels across all dose groups after a single dose. The mean changes in glucose, glucagon, insulin, and GLP-1 levels from pre-meal did not generate marked consistent trends at 2 hours post-dose for most of the treatment groups, including subjects with T2DM. Formula IIIa is a promising agent for the treatment of T2DM, demonstrating PD effects after a single dose, and multiple-ascending dose clinical trial are being conducted.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference in their entireties as if each publication, patent or patent application were specifically and individually indicated to be incorporated herein by reference.

What is claimed is:

1. An aqueous formulation comprising sulfobutylether 7-b-cyclodextrin and about 40 mg of a compound of Formula I:

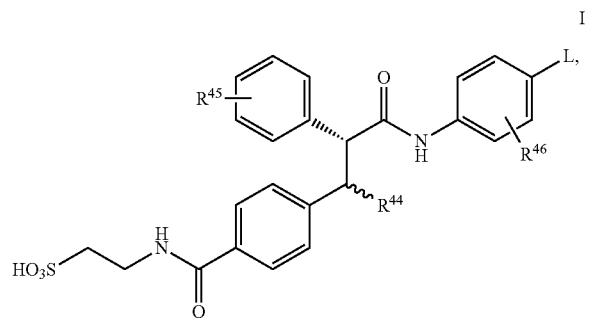

I wherein
  $R^{44}$ is H, $CH_3$ or $CH_3CH_2$;
  $R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or heteroaryl, any of which can be optionally substituted with one or more substituents selected from $C_{1-6}$-alkyl, $CF_3$, F, CN or $OCF_3$;
  L is phenyl, indenyl, benzoxazol-2-yl, $C_{3-6}$-cycloalkyl, $C_{4-8}$-cycloalkenyl or $C_{4-8}$-bicycloalkenyl, any of which can be optionally substituted with one or more substituents selected from F, Cl, $CH_3$, $CF_3$, $OCF_3$ or CN; and
  $R_{46}$ represents one or more substituents selected from H, F, Cl, $CH_3$, $CF_3$, $OCF_3$ or CN;
  or a pharmaceutically acceptable salt, solvate, or prodrug thereof.

2. The aqueous formulation of claim 1, wherein:
  $R^{44}$ is H, $CH_3$ or $CH_3CH_2$;
  $R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or heteroaryl, any of which can be optionally substituted with one or more substituents selected from $C_{1-6}$-alkyl, $CF_3$, F, CN or $OCF_3$;
  L is phenyl, indenyl, benzoxazol-2-yl or 4,4-dimethylcyclohexenyl, any of which can be optionally substituted with one or more substituents selected from F, Cl, $CH_3$, $CF_3$, $OCF_3$ or CN; and
  $R^{46}$ is H, F, Cl, $CH_3$, $CF_3$, $OCF_3$ or CN.

3. The aqueous formulation of claim 1, wherein L is phenyl, benzoxazol-2-yl or 4,4-dimethylcyclohexenyl, any of which can be optionally substituted with one or more substituents selected from F, Cl, $CH_3$, $CF_3$, $OCF_3$ or CN.

4. The aqueous formulation of claim 1, wherein L is 4-chloro-2-methylphenyl, 4-methyl-2-benzoxazolyl, 2,4,6-trimethylphenyl, 2-benzoxazolyl, 4-chloro-3-methylphenyl or 4,4-dimethylcyclohexenyl.

5. The aqueous formulation of claim 1, wherein $R^{44}$ is H or $CH_3$.

6. The aqueous formulation of claim 1, wherein $R^{45}$ is attached to the 3 (meta) or 4 (para) position.

7. The aqueous formulation of claim 1, wherein $R^{45}$ is alkenyl, $C_{3-6}$-cycloalkyl, $C_{4-8}$-cycloalkenyl, $C_{4-8}$-bicycloalkenyl or phenyl, any of which can be optionally substituted with one or more substituents selected from $C_{1-6}$-alkyl or $CF_3$.

8. The aqueous formulation of claim 1, wherein $R^{45}$ is substituted with one or more substituents independently selected from $CH_3$ and $(CH_3)_3C$—.

9. The aqueous formulation of claim 1, wherein $R^{45}$ is selected from $(CH_3)_3CCH$=$CH$—, t-butyl-cycloalkyl-, dimethyl-cycloalkyl-, t-butyl-cycloalkenyl-, dimethyl-cycloalkenyl-, bicycloalkenyl- or t-butyl-phenyl-.

10. The aqueous formulation of claim 1, wherein $R^{45}$ is trans-t-butylvinyl, cis-4-t-butylcyclohexyl, trans-4-t-butylcyclohexyl, 4,4-dimethylcyclohexyl, cyclohex-1-enyl, (S)-4-t-butylcyclohex-1-enyl, (R)-4-t-butylcyclohex-1-enyl, 4,4-dimethylcyclohex-1-enyl, 4,4-diethylcyclohex-1-enyl, 4,4-diethylcyclohexyl, 4,4-dipropylcyclohex-1-enyl, 4,4-dipropylcyclohexyl, 4,4-dimethylcyclo hexa-1,5-dienyl, (1R,4S)1,7,7-trimethylbicyclo[2.2.1]3-heptyl-2-ene, (1R,4R)-1,7,7-trimethylbicyclo[2.2.1]2-heptyl-2-ene, 2-methyl-4-chloro-phenyl, 2,4,6-trimethylphenyl or 4-t-butylphenyl.

11. The aqueous formulation of claim 1, wherein $R^{45}$ is trans-t-butylvinyl, cis-4-t-butylcyclohexyl, trans-4-t-butylcyclohexyl, 4,4-dimethylcyclohexyl (S)-4-t-butylcyclohex-1-enyl, (R)-4-t-butylcyclohex-1-enyl, 4,4-dimethylcyclohex-1-enyl, (1R,4R)-1,7,7-trimethylbicyclo[2.2.1]2-heptyl-2-ene or 4-t-butylphenyl.

12. The aqueous formulation of claim 1, wherein $R^{46}$ is 1-H or $CH_3$.

13. The aqueous formulation of claim 1, wherein the compound is selected from the group

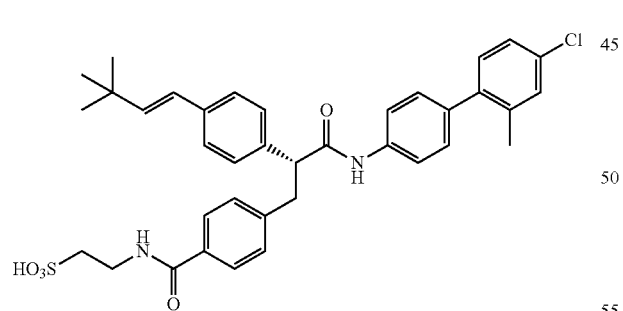

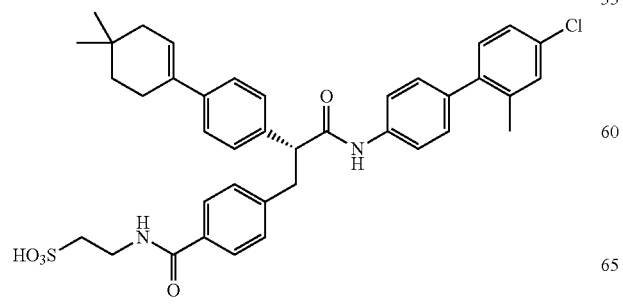

-continued

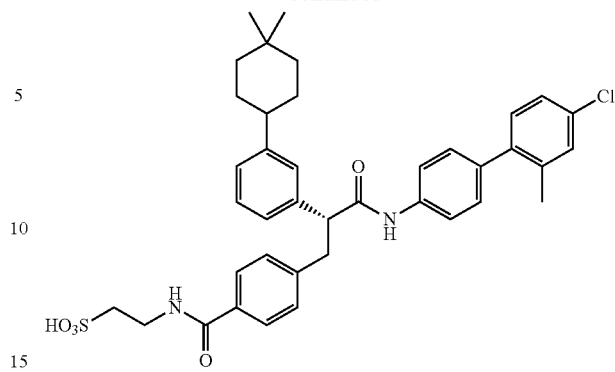

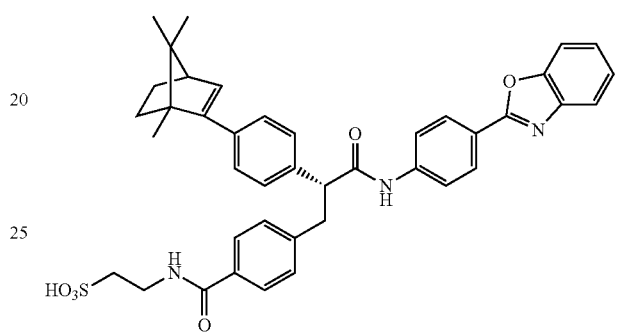

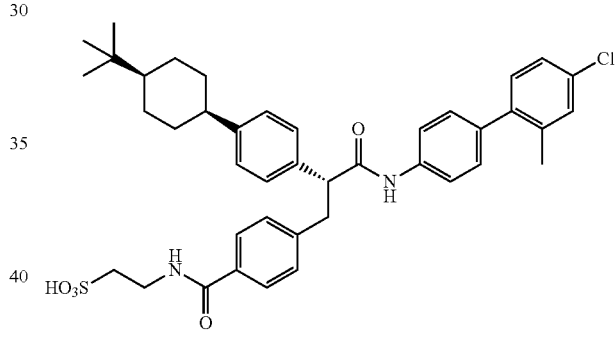

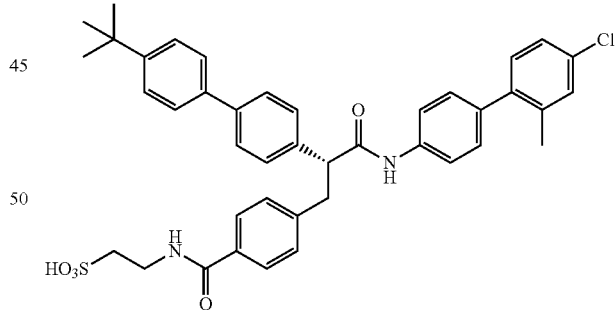

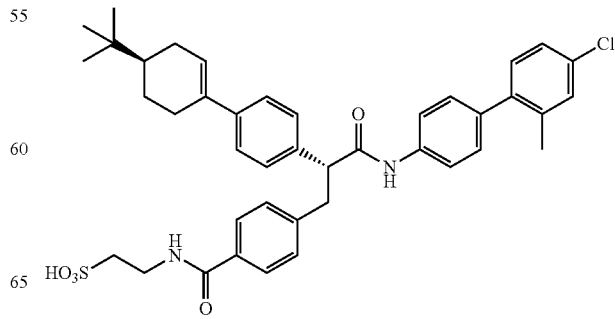

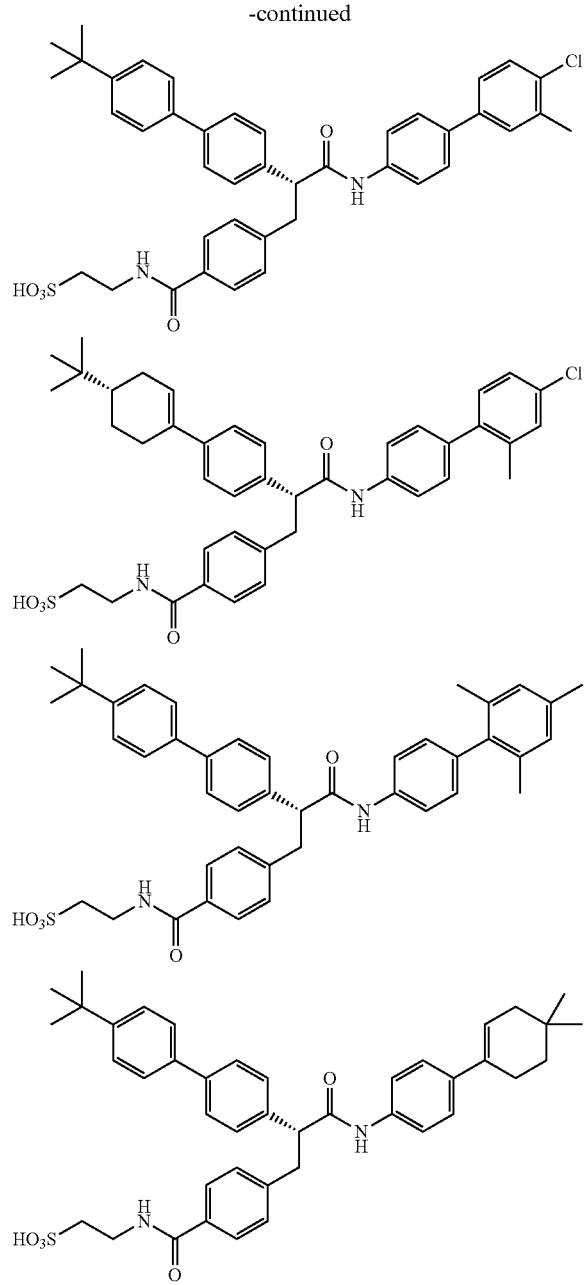
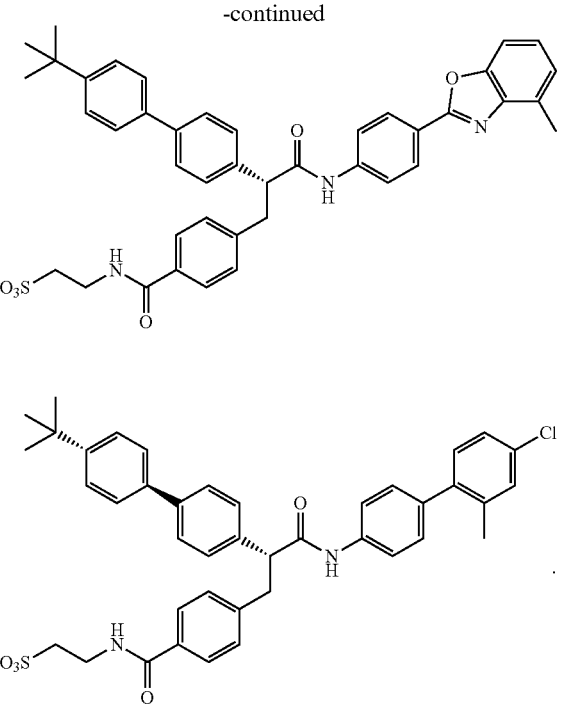
14. The aqueous formulation of claim 1, wherein the compound is
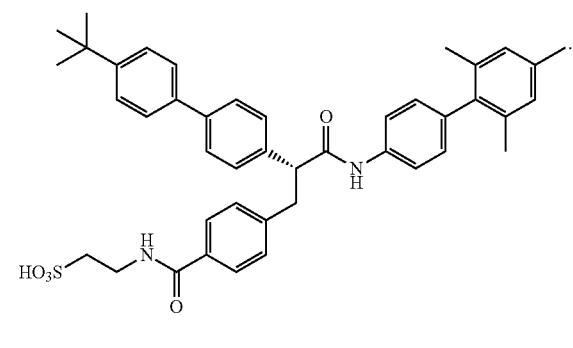 [SMILES: Cc1cc(C)c(-c2ccc(NC(=O)[C@H](Cc3ccc(C(=O)NCCS(=O)(=O)O)cc3)c3ccc(-c4ccc(C(C)(C)C)cc4)cc3)cc2)c(C)c1]
15. The aqueous formulation of claim 1, wherein the compound is in the amount of 40 mg.
* * * * *